(12) United States Patent  
Holschneider et al.

(10) Patent No.: US 8,249,697 B2  
(45) Date of Patent: Aug. 21, 2012

(54) CARDIAC OUTPUT MONITOR WITH COMPENSATION FOR TISSUE PERFUSION

(75) Inventors: Daniel P. Holschneider, Los Angeles, CA (US); Eduardo H. Rubinstein, Los Angeles, CA (US); Jean-Michel I. Maarek, Rancho Palos Verdes, CA (US); Alan J. Eskovitz, Los Angeles, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 581 days.

(21) Appl. No.: 12/574,524

(22) Filed: Oct. 6, 2009

(65) Prior Publication Data

US 2010/0099992 A1    Apr. 22, 2010

Related U.S. Application Data

(60) Provisional application No. 61/103,488, filed on Oct. 7, 2008.

(51) Int. Cl.  
   *A61B 6/00* (2006.01)
(52) U.S. Cl. ........ 600/476; 600/407; 600/473; 600/475; 600/477; 600/478
(58) Field of Classification Search .................. 600/407, 600/473–480, 508  
See application file for complete search history.

(56) References Cited

U.S. PATENT DOCUMENTS

| | | | |
|---|---|---|---|
| 4,730,622 A | 3/1988 | Cohen | |
| 5,217,456 A | 6/1993 | Narciso, Jr. | |
| 5,339,817 A * | 8/1994 | Nilsson | 600/473 |
| 5,766,125 A | 6/1998 | Aoyagi | |
| 5,999,841 A | 12/1999 | Aoyagi | |
| 6,219,566 B1 | 4/2001 | Weersink | |
| 6,230,035 B1 | 5/2001 | Aoyagi | |
| 6,299,583 B1 * | 10/2001 | Eggers et al. | 600/526 |
| 6,757,554 B2 | 6/2004 | Rubinstein | |
| 7,474,906 B2 | 1/2009 | Rubinstein | |
| 7,590,437 B2 | 9/2009 | Rubinstein | |
| 7,611,470 B2 * | 11/2009 | Rubinstein et al. | 600/504 |
| 2007/0203403 A1 | 8/2007 | Rubinstein | |
| 2008/0015434 A1 | 1/2008 | Rubinstein | |
| 2008/0027298 A1 | 1/2008 | Blanco | |

OTHER PUBLICATIONS

International Search Report for PCT Application No. PCT/US2007/015650, filed Jul. 9, 2007, mailed Aug. 20, 2008.  
Sakka, G. et al. 2002. Comparison of Cardiac Output and Circulatory Blood Volumes by Transpulmonary Thermo-dye Dilution and Transcutaneous Indocyanine Green Measurement in Critically Ill Patients. Feb. 2002. CHEST, vol. 121, No. 2, pp. 559-565.  
Darovic, G.O. 1995. Hemodynamic monitoring. Chapter 11: Monitoring cardiac output. pp. 327-332, 344-346. 2d Ed. W.B. Saunders.

(Continued)

*Primary Examiner* — James Kish  
(74) *Attorney, Agent, or Firm* — McDermott Will & Emery LLP

(57) ABSTRACT

A non-invasive system and method for determination of cardiac output and blood volume of a patient includes compensating for a change in the fluorescence of an indicator circulating in the bloodstream of a tissue or organ that is caused by a variation of the blood content at the site of the measurement.

20 Claims, 34 Drawing Sheets

OTHER PUBLICATIONS

Desmettre, T. et al. 2000. Fluorescence properties and metabolic features of indocyanine green (ICG) as related to angiography. Survey of opthalmology. Jul.-Aug. 2000. vol. 45, No. 1, pp. 15-27.

Diamond, K.R. et al. 2003. Quantification of fluorophore concentration in tissue-simulating media by fluorescence measurements with a single optical fiber. Applied Optics, May 1, 2003, vol. 42, No. 13, pp. 2436-2442.

Dorshow. R.B. et al. 1998. Noninvasive fluorescence detection of hepatic and renal function. Journal of biomedical optics. Jul. 1998. vol. 3, No. 3, pp. 340-345.

Edwards, A.D. et al. 1993. Measurement of hemoglobin flow and blood flow by near-infrared spectroscopy. J. Applied Physiology, vol. 75, pp. 1884-1889.

Fok. T.-F. et al. 2001. Oxygen consumption by lungs with acute and chronic injury in a rabbit model. Intensive care medicine. vol. 27, pp. 1532-1538.

Geddes, L.A. 1984. Cardiovascular devices and their applications. Chapter 4: The measurement of cardiac output and blood flow. pp. 101-122, 186-188. John Wiley & Sons, New York.

Hollins, B. et al. 1987. Fluorometric determination of indocyanine green in plasma. Clinical chemistry. vol. 33, No. 6, pp. 765-768.

Iijima T. et al. 1997. Cardiac output and circulating blood volume analysis by pulse dye densitometry. Journal of Clinical Monitoring, vol. 13, pp. 81-89.

Maarek, J-M. et al. 2007. Fluorescence Dilution Technique for Measurement of Cardiac Output and Circulating Blood Volume in Healthy Human Subjects. Anesthesiology, vol. 106, pp. 491-498.

Preckel, B. et al. 2000. Effect of dantrolene in an in vivo and in vitro model of myocardial reperfusion injury. Acta Anaesthesiol Scand. vol. 44, pp. 194-201.

Wang, L. et al. 1995. MCML—Monte Carlo modeling of light transport in multi-layered tissues. Computer Methods & Programs in Biomedicine, vol. 47, No. 2, pp. 131-146.

Weersink et al. 2001. Noninvasive measurement of fluorophore concentration in turbid media with a simple fluorescence/reflectance ratio technique. Applied Optics, Dec. 2001, vol. 40, No. 34, pp. 6389-6395.

* cited by examiner

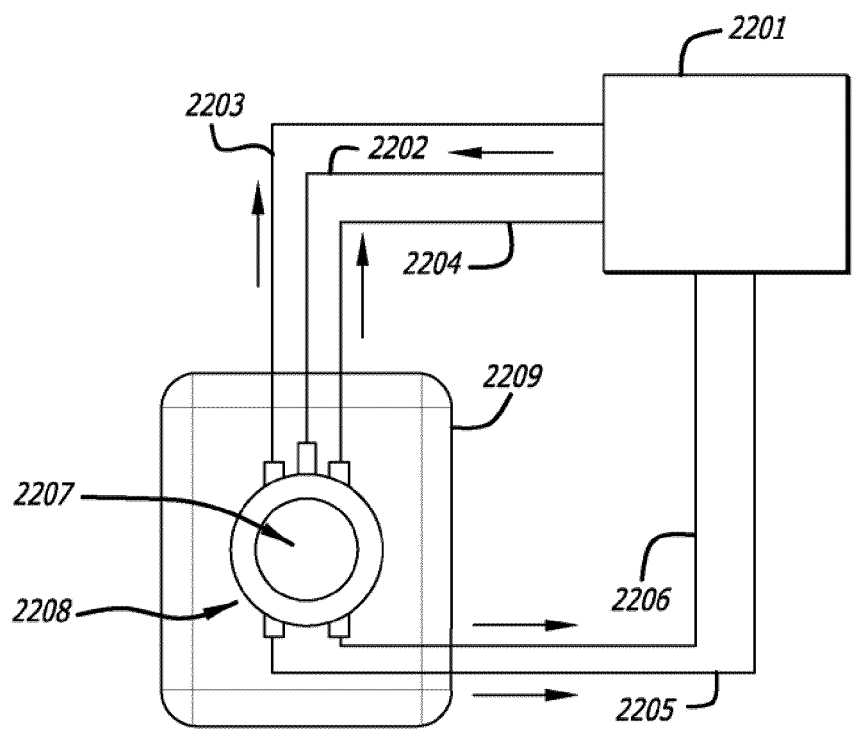
FIG. 22A
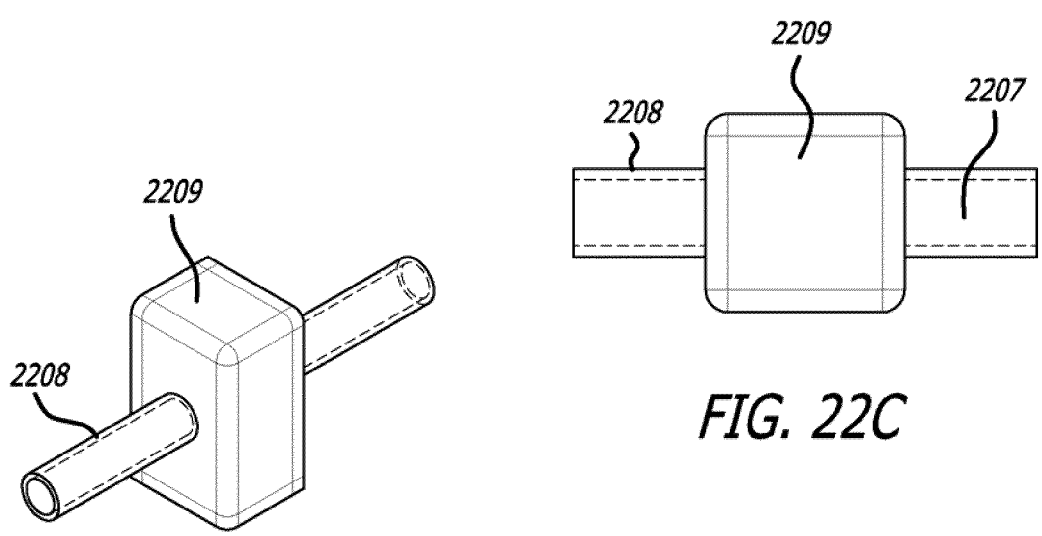
FIG. 22B
FIG. 22C

CARDIAC OUTPUT MONITOR WITH COMPENSATION FOR TISSUE PERFUSION

CROSS-REFERENCE TO RELATED APPLICATIONS

This application is based upon and claims priority to U.S. Provisional Application Ser. No. 61/103,488, filed Oct. 7, 2008, entitled "Cardiac Output Monitor with Compensation for Tissue Perfusion," the entire content of which is incorporated herein by reference. This application is also related to U.S. patent application Ser. No. 10/847,480, filed May 17, 2004 (now U.S. Pat. No. 7,590,437, issued Sep. 15, 2009), entitled "Measurement of Cardiac Output and Blood Volume by Non-Invasive Detection of Indicator Dilution"; U.S. patent application Ser. No. 10/153,387, filed May 21, 2002 (now U.S. Pat. No. 6,757,554, issued Jun. 29, 2004), entitled "Measurement of Cardiac Output and Blood Volume by Non-Invasive Detection of Indicator Dilution"; U.S. patent application Ser. No. 11/625,184, filed Jan. 19, 2007, entitled "Method and Apparatus for Measurement of Cardiac Output and Blood Volume by Non-Invasive Detection of Indicator Dilution"; U.S. patent application Ser. No. 11/744,147, filed May 3, 2007 (now U.S. Pat. No. 7,474,906, issued Jan. 6, 2009), entitled "Method for Dye Injection for the Transcutaneous Measurement of Cardiac Output"; U.S. patent application Ser. No. 11/744,157, filed May 3, 2007, entitled "Method and Apparatus for Measurement of Cardiac Output and Blood Volume by Non-Invasive Detection of Indicator Dilution For Hemodialysis"; U.S. patent application Ser. No. 11/744,229, filed Jul. 6, 2007, entitled "System for Repetitive Measurement Of Cardiac Output In a Freely Moving Body"; U.S. Provisional Application Ser. No. 60/985,799, filed Nov. 6, 2007, entitled "Measurement of Hematocrit and Cardiac Output from Optical Transmission and Reflection Changes"; and U.S. Provisional Application Ser. No. 61/014,546, filed Dec. 18, 2007, entitled "A Cardiac Output Monitoring Probe and Calibrator." The content of all of these applications is incorporated herein by reference.

BACKGROUND

Technical Field

1. Field

This application pertains to the detection of parameters of cardiovascular system of a subject.

2. Description of Related Art

General Background and State of the Art: Cardiac output is a central part of the hemodynamic assessment in patients, for example, having heart disease or acute hemodynamic compromise, or undergoing cardiac surgery. Cardiac output is a measure of the heart's effectiveness at circulating blood throughout the circulatory system. Specifically, cardiac output (measured in L/min) is the volume of blood expelled by the heart per beat (stroke volume) multiplied by the heart rate. An abnormal cardiac output is at least one indicator of cardiovascular disease.

The current standard method for measuring cardiac output is the thermodilution technique (Darovic, G. O. Hemodynamic monitoring: invasive and noninvasive clinical application. 2nd Ed. W.B. Saunders, 1995). Generally, the technique involves injecting a thermal indicator (cold or hot) into the right side of the heart and detecting a change in temperature caused as the indicator flows into the pulmonary artery.

Typically, the thermodilution technique involves inserting a flow-directed balloon catheter (such as a Swan-Ganz catheter) into a central vein (basilic, internal jugular or subclavian) and guiding it through the right atrium and ventricle to the pulmonary artery. The balloon catheter is typically equipped with a thermistor near its tip for detecting changes in blood temperature. A rapid injection of a bolus of chilled glucose solution (through a port in the catheter located in the vena cava near the right atrium) results in a temperature change in the pulmonary artery detected with the thermistor. The measured temperature change is analyzed with an external electronic device to compute the cardiac output. The algorithm implemented in this computation is typically a variant of the Stewart-Hamilton technique and is based on the theory of indicator mixing in stirred flowing media (Geddes L. A., Cardiovascular devices and measurements. John Wiley & Sons. 1984).

Thermodilution measurements of cardiac output are disadvantageous for several reasons. First, placement of the thermodilution balloon catheter is an expensive and invasive technique requiring a sterile surgical field. Second, the catheter left in place has severe risks to the patient such as local infections, septicemia, bleeding, embolization, catheter-induced damage of the carotid, subclavian and pulmonary arteries, catheter retention, pneumothorax, dysrhythmias including ventricular fibrillation, perforation of the atrium or ventricle, tamponade, damage to the tricuspid values, knotting of the catheter, catheter transection and endocarditis. Third, only specially trained physicians can insert the balloon catheter for thermodilution cardiac output technique. Last, thermodilution measurements of the cardiac output are too invasive to be performed in small children and infants.

Another method used for measuring cardiac output is the dye indicator dilution technique. In this technique, a known volume and concentration of indicator is injected into the circulatory flow. At a downstream point, a blood sample is removed and the concentration of the indicator determined. The indicator concentration typically peaks rapidly due to first pass mixing of the indicator and then decreases rapidly as mixing proceeds in the total blood volume (~10 seconds; first pass concentration curve). Further, indicator concentration slowly diminishes as the indicator is metabolized and removed from the circulatory system by the liver and/or kidneys (time depending upon the indicator used). Thus, a concentration curve can be developed reflecting the concentration of the indicator over time. The theory of indicator dilution predicts that the area under the first pass concentration curve is inversely proportional to the cardiac output.

Historically, indicator dilution techniques have involved injecting a bolus of inert dye (such as indocyanine green) into a vein and removing blood samples to detect the concentration of dye in the blood over time. For example, blood samples are withdrawn from a peripheral artery at a constant rate with a pump. The blood samples are passed into an optical sensing cell in which the concentration of dye in the blood is measured. The measurement of dye concentration is based on changes in optical absorbance of the blood sample at several wavelengths.

Dye-dilution measurements of cardiac output have been found to be disadvantageous for several reasons. First, arterial blood withdrawal is time consuming, labor intensive and depletes the patient of valuable blood. Second, the instruments used to measure dye concentrations (densitometer) must be calibrated with samples of the patient's own blood containing known concentrations of the dye. This calibration process can be very laborious and time consuming in the context of the laboratory where several samples must be run on a daily basis. Further, technical difficulties arise in extracting the dye concentration from the optical absorbance measurements of the blood samples.

A variation on the dye-dilution technique is implemented in the Nihon Kohden pulse dye densitometer. In this technique, blood absorbance changes are detected through the skin with an optical probe using a variation of pulse oximetry principles. This variation improves on the prior technique by eliminating the necessity for repeated blood withdrawal. However, as described above, this technique remains limited by the difficulty of separating absorbance changes due to the dye concentration changes from absorbance changes due to changes in blood oxygen saturation or blood content in the volume of tissue interrogated by the optical probe. This method is also expensive in requiring large amounts of dye to create noticeable changes in absorbance and a light source producing two different wavelengths of light for measuring light absorption by the dye and hemoglobin differentially. Even so, the high background levels of absorption in the circulatory system make this technique inaccurate. Finally, where repeat measurements are desired, long intervals must ensue for the high levels of the indicator to clear from the blood stream. Thus, this technique is inconvenient for patients undergoing testing and practitioners awaiting results to begin or alter treatment.

Other approaches for measuring cardiac output exist which are not based on indicator dilution principles. These include ultrasound Doppler, ultrasound imaging, the Fick principle applied to oxygen consumption or carbon dioxide production and electric impedance plethysmography (Darovic, supra). However, these techniques have specific limitations. For instance, the ultrasound techniques (Doppler and imaging) require assumptions on the three-dimensional shape of the imaged structures to produce cardiac output values from velocity or dimension measurements.

Blood volume measures the amount of blood present in the cardiovascular system. Blood volume is also a diagnostic measure that is relevant to assessing the health of a patient. In many situations, such as during or after surgery, traumatic accident or in disease states, it is desirable to restore a patient's blood volume to normal as quickly as possible. Blood volume has typically been measured indirectly by evaluating multiple parameters (such as blood pressure and hematocrit). However, these measures are not as accurate or reliable as direct methods of measuring blood volume.

Blood volume has been directly measured using indicator dilution techniques (Geddes, supra). Briefly, a known amount of an indicator is injected into the circulatory system. After injection, a period of time is allowed to pass such that the indicator is distributed throughout the blood, but without clearance of the indicator from the body. After the equilibration period, a blood sample is drawn which contains the indicator diluted within the blood. The blood volume can then be calculated by dividing the amount of indicator injected by the concentration of indicator in the blood sample (for a more detailed description see U.S. Pat. No. 6,299,583 incorporated by reference). However, to date, the dilution techniques for determining blood volume are disadvantageous because they are limited to infrequent measurement due to the use of indicators that clear slowly from the blood.

In the dye dilution method, the dye must be injected as a rapid intravenous bolus, not as a continuous infusion, as the latter does not result in the characteristic dye dilution curve needed for the calculation of cardiac output. Choice of the injection method and volume of the injection are relevant to the measured cardiac output and the variability of sequential measurements of cardiac output obtained with transcutaneous fluorescence dye dilution. The venous system targeted by the injection is characterized by branching veins and venous valves. These present inherent resistances to injection which contributes to a potential fragmentation of the bolus, as well as to a pooling and delayed release of any residual dye. These can be noted, respectively, by fluctuations in the morphology of the dye dilution curve and a prolongation of the tail of the dye bolus.

Furthermore, cardiovascular disease is highly prevalent in patients with end-stage renal disease. Patients whose kidney function is insufficient to eliminate metabolic byproducts and water undergo kidney dialysis several times every week to clear their blood from these products. Typically, large needles are inserted at the level of an arterio-venous (AV) fistula or a synthetic AV graft in the arm of the patient and connected to the dialyzer for several hours during the procedure.

Fluid accumulation between dialysis sessions is mostly in the extravascular space. Fluid removal during dialysis is from the vascular space. If the rate of fluid transfer from the extravascular space to the vascular space does not match the rate of fluid removal, the patient experiences hypovolemia, which reduces cardiac output, blood pressure and peripheral perfusion. Hypotension resulting from a rapid decrease of the circulating blood volume is the most common complication from the dialysis procedure.

Current methods of monitoring fluid status in dialysis patients rely on weighing the patient before and after the dialysis procedure to assess the total fluid volume removed and on measuring changes in hematocrit during the procedure. Since the amount of red blood cells in the circulating blood does not change, the hematocrit increase during the dialysis can be used to track the blood volume change resulting from the procedure. Patient weighing does not provide intradialysis monitoring. Tracking relative changes of the blood volume based on hematocrit measurement is affected by the initial blood volume at the patient at the beginning of the dialysis session, which varies from session to session. Furthermore, it has been suggested that central blood volume, the volume of blood in the large vessels (primarily large veins) is more important than total blood volume with respect to maintaining cardiac filling, blood pressure and peripheral perfusion.

SUMMARY

The present cardiovascular measurement devices and methods assess cardiovascular parameters within the circulatory system using indicator dilution techniques. In particular, the present cardiovascular measurement devices and methods assess cardiac output and circulating blood volume of patients undergoing kidney hemodialysis from a measurement on the body surface or at the connection of the dialyzer with the patient of the fluorescence dilution recording observed following injection of an inert fluorescent dye in the venous bloodstream.

In one aspect of the present cardiovascular measurement devices and methods, a non-invasive method for determining cardiovascular parameters is described. In particular, a non-invasive fluorescent dye indicator dilution method is used to evaluate cardiovascular parameters. The method may be minimally invasive, requiring only a single peripheral, intravenous line for indicator injection into the circulatory system of the patient. Further, a blood draw may not be required for calibration of the system. Further, cardiovascular parameters may be evaluated by measuring physiological parameters relevant to assessing the function of the heart and circulatory system. Such parameters include, but are not limited to cardiac output and blood volume.

Such minimally invasive procedures are advantageous over other methods of evaluating the cardiovascular system. First, complications and patient discomfort caused by the procedures are reduced. Second, such practical and minimally invasive procedures are within the technical ability of most doctors and nursing staff, thus, specialized training is not required. Third, these minimally invasive methods may be performed at a patient's bedside or on an outpatient basis. Finally, methods may be used on a broader patient population, including patients whose low risk factors may not justify the use of central arterial measurements of cardiovascular parameters.

In another aspect of the cardiovascular measurement devices and methods, these methods may be utilized to evaluate the cardiovascular parameters of a patient at a given moment in time, or repeatedly over a selected period of time. The dosages of indicators and other aspects of the method can be selected such that rapid, serial measurements of cardiovascular parameters may be made. These methods can be well suited to monitoring patients having cardiac insufficiency or being exposed to pharmacological intervention over time. Further, the non-invasive methods may be used to evaluate a patient's cardiovascular parameters in a basal state and when the patient is exposed to conditions which may alter some cardiovascular parameters. Such conditions may include, but are not limited to changes in physical or emotional conditions, exposure to biologically active agents or surgery. For example, embodiments of the cardiovascular measurement devices and methods can be used for cardiac output monitoring before, during, or after kidney dialysis; cardiac output monitoring under shock conditions (such as septic shock, anaphylactic shock, cardiogenic shock, neurogenic shock and hypovolemic shock); cardiac output monitoring during stress tests to better understand the heart's ability to increase blood supply to the heart and body while exercising or under other conditions requiring additional blood flow through the heart; cardiac output monitoring before, during, and after chemotherapy treatment to monitor fluid equilibrium in the body; and cardiac output measurements for athletes needing to understand how their cardiac performance to improve their athletic performance.

In another aspect of the cardiovascular measurement devices and methods, modifications of the method may be undertaken to improve the measurement of cardiovascular parameters. Such modifications may include altering the placement of a photodetector relative to the patient or increasing blood flow to the detection area of the patient's body.

In yet another aspect of the cardiovascular measurement devices and methods, the non-invasive method of assessing cardiovascular parameters utilizes detection of indicator emission, which is fluorescence, as opposed to indicator absorption. Further, indicator emission may be detected in a transmission mode and/or reflection mode such that a broader range of patient tissues may serve as detection sites for evaluating cardiovascular parameters, as compared to other methods. Measurement of indicator emission can be more accurate than measurements obtained by other methods, as indicator emission can be detected directly and independent of the absorption properties of whole blood.

In a further aspect of the cardiovascular measurement devices and methods, a system for the non-invasive or minimally invasive assessment of cardiovascular parameters is described. In particular, such a system may include an illumination source for exciting the indicator, a photodetector for sensing emission of electromagnetic radiation from the indicator and a computing system for receiving emission data, tracking data over time and calculating cardiovascular parameters using the data.

In another aspect of the cardiovascular measurement devices and methods, the methods and system described herein may be used to assess cardiovascular parameters of a variety of subjects. In some embodiments, the methodology can be modified to examine animals or animal models of cardiovascular disease, such as cardiomyopathies. The cardiovascular measurement devices and methods are advantageous for studying animals, such as transgenic rodents whose small size prohibits the use of current methods using invasive procedures. The present cardiovascular measurement devices and methods are also advantageous in not requiring anesthesia which can effect cardiac output measurements.

In yet another aspect of the cardiovascular measurement devices and methods, a noninvasive calibration system can be used to determine the concentration of circulating indicator dye. In some embodiments, the concentration of circulating indicator dye can be determined from the ratio of emergent fluorescent light to transmitted and/or reflected excitation light.

In yet another aspect of the cardiovascular measurement devices and methods, a method for injection of the dye can improve the accuracy of the cardiac measurements. In some embodiments, the injection method comprises intravenous rapid bolus injection of a minimum volume of fluorescent dye followed by a rapid bolus injection of an inert solution (vehicle) without the dye.

In yet another aspect of the cardiovascular measurement devices and methods, a method for measuring cardiac output parameters comprises determining non-invasively and transcutaneously the cardiac output and circulating blood volume of patients undergoing kidney hemodialysis from a measurement on the body surface or at the connection of the dialyzer with the patient of the fluorescence dilution recording observed following injection of an inert fluorescent dye in the venous bloodstream. The measurement site may be illuminated with a light source that causes the dye circulating with the bloodstream to fluoresce and the fluorescence signal can be recorded transcutaneously or across the connection tubes between the patient and the dialyzer.

In yet another aspect of cardiovascular measurement devices and methods, a method of calibration of a probe for a kidney dialysis system has been disclosed since, as fluid is removed from the vascular space, the circulating blood hematocrit increases and the blood becomes more concentrated in hemoglobin. The increase of the blood hematocrit changes the optical properties of the blood. To quantify these effects and find a way to calibrate the fluorescence signal, a model of the propagation of light in a blood slab containing ICG has been made allowing the ICG concentration and the hemoglobin content of the blood to vary. The model was used to develop a method of calibration that determines the concentration of the fluorescent indicator ICG as a function of the fluorescence signal independently of variations of the hemoglobin content of the blood.

In yet another aspect of the cardiovascular measurement devices and methods, a method of determining cardiac output from optical transmission and reflection changes due to hematocrit has been disclosed In yet another aspect of the cardiovascular measurement devices and methods, a method of cardiac output determination based on the amount of plasma (e.g. saline) injected and the hematocrit change trace integrated over time.

In yet another aspect of the cardiovascular measurement devices and methods, the method of cardiac output determination based on the amount of plasma (e.g. saline) injected and the hematocrit change can be performed transcutaneously, tranarterially, intraarterially or across an extracorporeal arterial circulatory path.

In other embodiments of the cardiovascular measurement devices and methods, the methodology can be modified for clinical application to human patients. The present cardiovascular measurement devices and methods may be used on all human subjects, including adults, juveniles, children and neonates.

In yet another aspect of the cardiovascular measurement system and methods, the dialysis probe having the required optical fibers may be a ring like device having a channel opening which the blood tubing may snap into.

In yet another aspect of the cardiovascular measurement system and methods, the dialysis probe of the system may be calibrated by a probe calibrator, wherein the calibrator replaces the blood tubing and its generated lights.

An alternative embodiment comprises compensating for a change in the fluorescence of an indicator circulating in the bloodstream of a tissue or organ that is caused by a variation of the blood content of the detection area (i.e. measurement site). This compensation is achieved by using Doppler flowmetry technique.

A system of this alternative embodiment that may be used for determining a physical parameter of the cardiovascular system of a subject comprises an illumination system, a detection system and a computing system. The illumination system may be configured to provide an electromagnetic radiation to a detection area to excite an indicator administered to the cardiovascular system to fluoresce, and to provide said electromagnetic radiation to said detection area for a Doppler flowmetry measurement. The detection system may be configured to detect the indicator fluorescence intensity emerging from the detection area, and to detect the intensity and the frequency distribution of electromagnetic radiation reflected from the detection area. The computing system may be configured to (a) compute a parameter of the cardiovascular system by using the indicator fluorescence intensity, (b) compute a Doppler flowmetry parameter of the detection area by using the reflected electromagnetic radiation intensity and its frequency distribution, and (c) compensate the cardiovascular system computation for a variation of the blood content of the detection area by using the computed Doppler flowmetry parameter.

In this alternative embodiment, the illumination system may provide an electromagnetic radiation with a wavelength within the range of 400 nm to 1,000 nm. The electromagnetic radiation may even be provided with a wavelength within the range of 600 nm to 1,000 nm. The indicator of this alternative embodiment may be capable of fluorescing with a wavelength within the range of 400 nm to 1,000 nm. The indicator may also be capable of fluorescing with a wavelength within the range of 600 nm to 1,000 nm. For example, the indicator may comprise indocyanine green, fluorescein, rhodamine or mixtures thereof. This illumination system may be configured to provide electromagnetic radiation at least at one wavelength to cause the indicator to fluoresce and for the Doppler flowmetry measurement. For example, it may provide a laser light at about 780 nm for both the fluorescence and the Doppler flowmetry measurements. This illumination system may also be configured to provide electromagnetic radiation at a plurality of wavelengths to cause the indicator to fluoresce and for the Doppler flowmetry measurement.

The illumination system of this alternative embodiment may also be configured to provide a modulated electromagnetic radiation during detection of the indicator fluorescence intensity. In such embodiment, the system may comprise an illumination system configured to modulate the electromagnetic radiation intensity at a selected frequency, and a detection system configured to enhance the detection of the indicator fluorescence only at the selected modulation frequency by using a suitable demodulating system comprising, for example, a lock-in amplifier or a synchronous demodulator. In such embodiment, the system may further be configured to carry out the Doppler flowmetry measurements when the electromagnetic radiation is not modulated.

In this alternative embodiment, the system may further be configured for a calibration of the system for the fluorescence measurement by using a minimally invasive calibration technique. The system calibration may also be achieved by using a noninvasive calibration technique. The system may also be configured to compute the cardiac output of the subject in absolute units of volume over time by first converting the indicator fluorescence intensity detected over a period of time to a measured indicator concentration using a known calibration curve and then computing the cardiac output of the subject in absolute units over the period of time based on the measured indicator concentration. The system may also be configured to compute the blood volume of the subject in absolute units of volume over time by converting the indicator fluorescence intensity detected over a period of time to a measured indicator concentration using a known calibration curve and computing the blood volume by back extrapolating a slow phase of the indicator concentration curve to determine the blood volume.

In this alternative embodiment, the placement of the illumination system may be noninvasive, minimally invasive or invasive to provide the electromagnetic radiation to the detection area. For example, the illumination system may be placed in proximity to fingers, auricles of ears, or nostrils. It may also be placed subdermally in proximity to any blood vessel. The illumination system may also be placed intravascularly, for example within an artery. Similarly, in this alternative embodiment, the placement of the detection system may be noninvasive, minimally invasive or invasive in detection of the indicator fluorescence emerging and the electromagnetic radiation reflected form the detection area. For example, the detection system may be placed in proximity to fingers, auricles of ears, or nostrils. It may also be placed subdermally in proximity to any blood vessel. The detection system may also be placed intravascularly, for example within an artery.

In this alternative embodiment, a method of measuring a physical parameter of the cardiovascular system of a subject comprises (a) administering to the cardiovascular system of a subject a detectable amount of at least one indicator; (b) providing an electromagnetic radiation to a detection area by using an illumination system to excite the indicator present at the detection area thereby causing the indicator to fluoresce; (c) detecting the indicator fluorescence intensity emitted from the detection area by using a detection system; (d) detecting the intensity and the frequency distribution of the reflected electromagnetic radiation for a Doppler flowmetry measurement by using said detection system, (e) computing at least one physical parameter of the cardiovascular system using the detected indicator fluorescence intensity, and (f) compensating the physical parameter of the cardiovascular system for variations of the blood content of the detection area by using the Doppler flowmetry measurement.

In this alternative method, the electromagnetic radiation may be provided at a wavelength varying within the range of 400 nm to 1,000 nm. The electromagnetic radiation may also be provided at a wavelength varying within the range of 600 nm and 1,000 nm. And the indicator may be capable of fluorescing at a wavelength varying within the range of 400 nm to 1,000 nm. The indicator may also be capable of fluorescing at a wavelength varying within the range of 600 nm to 1,000 nm. Examples of the indicator suitable for this alternative embodiment may comprise indocyanine green, fluorescein, rhodamine or mixtures thereof. In this method the electromagnetic radiation may be provided to the detection area at one wavelength. For example, it may be a laser light at about 780 nm provided both for the fluorescence and the Doppler flowmetry measurements. The electromagnetic radiation may also be provided at a plurality of wavelengths to cause the indicator to fluoresce and for the Doppler flowmetry measurement.

In this alternative method, the provided electromagnetic radiation may be modulated during the detection of the indicator fluorescence intensity. This method may further comprise carrying out the Doppler flowmetry measurement when the electromagnetic radiation is not modulated.

This alternative method may further comprise calibrating the system by a minimally invasive calibration technique. This calibration may also be achieved by a noninvasive calibration technique. The alternative method further comprises converting the measured indicator fluorescence intensity over the time period to a measured indicator concentration using a known calibration curve and determining the cardiac output of the subject in absolute units over the time period based on the measured indicator concentration.

This alternative method may further comprise removing a blood sample containing indicator from the subject, determining the indicator concentration in the removed blood sample, and computing the at least one physical parameter of the cardiovascular system using the determined indicator concentration. This physical parameter may be cardiac output. For this parameter determination, the method may further comprise detecting the indicator fluorescence intensity over a time period and forming an indicator fluorescence intensity curve for the time period. The cardiac output computation may comprise at least one of curve fitting to a model equation or numerical integration. This physical parameter may also be blood volume. For this parameter determination, the method further comprises detecting the indicator fluorescence intensity over a time period and forming an indicator fluorescence intensity curve for the time period. The blood volume computation may comprise back extrapolating a slow phase of the intensity curve to determine the blood volume.

In this alternative method, the detection area may be arterialized by application of heat or pharmacologically, for example, prior to detecting the indicator fluorescence and/or the reflected light.

BRIEF DESCRIPTION OF THE DRAWINGS

FIGS. 22A-C is a depiction of multiple views of an alternative embodiment of a probe used in a hemodialysis process.

DETAILED DESCRIPTION OF ILLUSTRATIVE EMBODIMENTS

The method and system of the present cardiovascular measurement devices and methods are for the evaluation of cardiovascular parameters of a subject using an indicator dilution technique.

Figure 9:
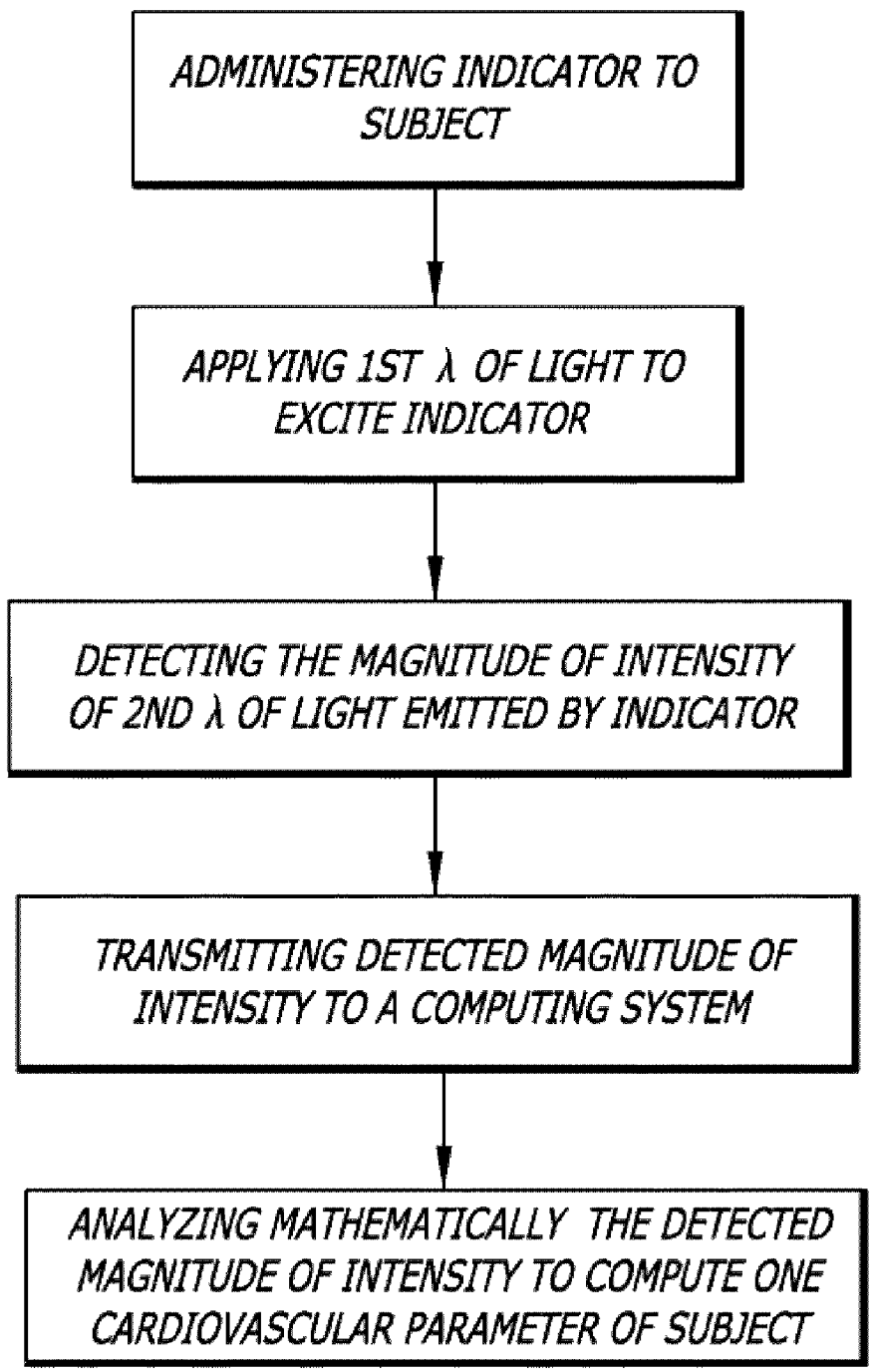
FIG. 9 is a flow chart depicting one exemplary cardiac output measurement.

The method of cardiac output generally involves the injection of a selected amount of indicator into the bloodstream of the subject (FIG. 9). The indicator can be illuminated using a first wavelength of excitation light selected to cause the indicator to fluoresce and emit a second wavelength of light. A photodetector can be placed near the subject for the detection of the intensity of the emitted second wavelength of light, which is proportional to the concentration of the indicator circulating within the circulatory system. The photodetector transmits this intensity information to a computing system, which records and preferably maps the intensity curve of the indicator detected over time.

Typically, the indicator concentration values increase to a peak rapidly after injection of the indicator. Then, the concentration values decrease rapidly, then more steadily as the indicator is mixed throughout the body circulatory system and metabolized over time. A microprocessor driven computation then can calculate from the concentration curve, the patient's cardiac output and/or blood volume values. Additionally, values can be generalized repeatedly using this method, at intervals of about every 2-5 minutes.

Indicators. The indicators useful in the cardiovascular measurement devices and methods may be inert and biocompatible in that they should not alter cardiovascular parameters such as heart rate. Further, the indicator may be a substance that once injected, does not diffuse out of the vasculature of the cardiovascular system. Also, the indicator may be selected to be one which is metabolized within the body at a rate such that repeated measures using this method may be conducted at intervals of about 2-5 minutes. It is also desirable that the background levels of circulating indicator be cleared between intervals, although measurements may be taken when background levels are not zero. Finally, the indicator can be selected to be detectable by the photodetector system selected.

In an exemplary embodiment, a non-invasive dye indicator dilution method may be used to evaluate cardiovascular function. Many different dye indicators may be used. The dye indicator may be fluorescent, having an excitation wavelength and an emission wavelength in the near infrared spectrum, preferably about 750 nm to about 1000 nm, and more preferably about 750 nm to about 850 nm.

For example, the indicator used may be indocyanine green (ICG; purchased for example from Akorn, Decatur or Sigma, St. Louis, Mo.; commercial names: Diagnogreen©, ICGreen©, Infracyanine©, Pulsion©). ICG has previously been used to study the microcirculation of the eye, the digestive system and liver function (Desmettre, T., J. M. Devoisselle, and S. Mordon. Fluorescence properties and metabolic features of indocyanine green (ICG) as related to angiography. Sury Opthalmol 45, 15-27, 2000). ICG fluoresces intensely when excited at near infrared wavelengths. ICG in blood plasma has a peak fluorescence of about 810 to 830 nm with an optimal excitation wavelength of about 780 nm (Hollins, B. et al. Fluorometric determination of indocyanine green in plasma. Clinical chemistry. 1987. pp. 765-768. vol. 33, No. 6; Dorshow. R. B. et al. Noninvasive fluorescence detection of hepatic and renal function. Journal of biomedical optics. July 1998. pp. 340-345. vol. 3, No. 3.). ICG breaks down quickly in aqueous solution, and metabolites are not fluorescent, minimizing recirculation artifact and reducing the time period between which measurements can be made. The wavelength of emission of ICG is also within the optical window (750-1000 nm) in which living tissues are relatively transparent to light.

Other biocompatible fluorescent dyes such as fluorescein and rhodamine would also be suitable in the cardiovascular measurement devices and methods. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

Indicator injection and dosage. The dosage of indicator can be selected such that an amount used is non-toxic to the subject, is present in the circulatory system for an amount of time adequate to establish an indicator concentration curve, but is metabolized in an amount of time such that repeated measurements can be conducted at intervals of about 2-5 minutes apart. Further, the indicator can be administered to the subject by injection into a vein.

In one exemplary embodiment, a dosage of about 0.015 mg/kg may be used as this dosage leads to peak blood concentrations below 0.002 mg/ml. In this concentration range, the measurement of the circulating indicator concentration is linearly related to the intensity of the emission wavelength detected. For example, in a laboratory animal model, about 0.045 mg can be injected into a 3 kg rabbit (blood volume=200 ml) such that the average circulating concentration is about 0.00023 mg/ml whole blood.

Dye dilution techniques have been applied in humans in other methods and systems using indocyanine green as a dye. Living tissues of humans and animals are relatively transparent for near infrared wavelengths of light which allows for transmission of light across several mm of tissue and transcutaneous detection of the fluorescence emission of ICG. The use of dosages in the ranges stated above is additionally suitable for human use.

In an exemplary embodiment, the injection method comprises intravenous rapid bolus injection of a minimum volume of fluorescent dye followed by a rapid bolus injection of an inert solution or vehicle (such as saline, for example) without the dye. For example, for an average 70 kg male, the injection method could include a 1.5 ml injection of the dye in solution, followed by a 3-5 ml flush with the vehicle (physiologic inert solution), each delivered over 1-2 seconds. The volumes and rates of injection would be expected to be different between application of this method in infants, children and adults, with the doses for infants and children being scaled down when compared to the adult doses. In some embodiments, the dye and the vehicle without the dye could be delivered in separate syringes, through a combination of a syringe and a fluid filled bag, or through a double barrel syringe or single syringe with separate compartments. The injection could either be delivered manually or using an automatic injector. If an automatic injector were employed, injection could be triggered by an external signal such as the subject's respiratory cycle, electrocardiogram or other biologic signal.

In most clinical or biological applications demanding bolus intravenous injection, the speed of injection, the volume of the bolus and whether or not the bolus is followed by a flush is typically not critical. In the thermodilution method, rapid injection may be helpful to obtain optimal signals for the thermodilution curve necessary for the calculation of cardiac output. In the thermodilution method, however, contrary to the dye dilution method, the volume of the injectate may not be too small. A bolus of small volume would result in excessive thermal losses of the injectate prior to reaching the sensing thermistor at the catheter's tip, with a resultant loss of the detected thermodilution signal. Typical volumes of injection for adults undergoing cardiac output measurement with the thermodilution method are 10 ml of an iced solution, with volumes substantially less resulting in questionable results. This compares to 1.5 ml typically used as the volume of injection for the transcutaneous dye dilution method of measuring cardiac output. Substantially larger volumes may present problems because of the prolonged duration to make such injections into a peripheral vessel and consequent susceptibility of the bolus to pooling and fragmentation. While the injectate in the thermodilution method is typically delivered with an invasive balloon catheter by an injection port deep in the venous compartment near the right atrium, the injectate in the fluorescence dye dilution method may be delivered through a short (1-2 in) catheter inserted in a peripheral vein.

Illumination Source. The illumination sources useful in cardiovascular measurement devices and methods may be selected to produce an excitation wavelength in the near infrared spectrum, in some embodiments about 750 nm to about 1000 nm, and in other exemplary embodiments about 750 to about 850 nm. This selection is advantageous in at least that most tissues are relatively transparent to wavelengths in this range. Thus, in some embodiments, an indicator in the blood stream is excitable transcutaneously and indicator emission can be detected transcutaneously. Further, blood constituents do not fluoresce at these wavelengths, thus there may be no other contributor to the measured fluorescence emission signal. Therefore, this method is advantageous in that at least the sensitivity of detection in this method is improved over other methods, which measure indicator absorption, as opposed to emission.

However, it is within the scope of the cardiovascular measurement devices and methods to use other wavelengths of light, for example in the visible range of the spectrum as some tissues are relatively transparent even at these wavelengths. Selection of the illumination source, therefore, can depend in part on the indicator selected and the tissue from which detection will be made. The illumination source may be selected to result in the peak emission wavelength of the indicator.

Examples of illumination sources which may be used in the cardiovascular measurement devices and methods include, but are not limited to lamps, light emitting diodes (LEDs), lasers or diode lasers.

In some embodiments, modifications to the system or illumination source may be done to further maximize the sensitivity or accuracy of the system for measuring indicator concentration. For example, in some embodiments, the excitation wavelength produced by the illumination source will be steady. Alternatively, the excitation wavelength produced by the illumination source can be modulated to allow for a lock-in detection technique. The excitation light can also be chopped to allow for a boxcar integration detection technique.

For example, the illumination source may emit light in a periodic varying pattern having a fixed frequency and the emission recorded by the photodetector read at the same frequency to improve the accuracy of the readings. The periodic varying pattern and frequency can be selected to improve noise-rejection and should be selected to be compatible with the rest of the instrumentation (such as the light source and photodetector).

The illumination source may be adapted to target a detection area of the subject's tissue from which emission wavelength intensity will be recorded. In some embodiments, the illumination source may comprise an optic fiber for directing the excitation light to the detection area. In some embodiments, the illumination source may comprise mirrors, filters and/or lenses for directing the excitation light to the detection area.

Detection Areas. The target detection area is that location of a subject's tissue which is exposed to the excitation wavelength of light and/or from which the emission wavelength light intensity output may be measured.

The method of detection may be non-invasive. In these embodiments, a detection area can be selected such that a photodetector can be placed in proximity to the detection area and emission wavelength light intensity measured. The photodetector may be placed transdermally to at least one blood vessel, and in some embodiments transdermally to a highly vascularized tissue area. Examples of detection areas include, but are not limited to fingers, auricles of the ears, nostrils and areas having non-keratinized epithelium (such as the nasal mucosa or inner cheek). In alternative embodiments, the method of detection is minimally invasive. For example, the photodetector can be placed subdermally (within or beneath the epidermis) and proximate to at least one blood vessel or in a perivascular position.

In yet alternative exemplary embodiments, the method of detection is minimally invasive. For example, the photodetector can be placed intravascularly to detect indicator emissions, such as within an artery. In such embodiments, an external probe for emitting and receiving light may not be needed. For example, in some embodiments the probe may include a fiber optic located within an intravascular catheter. Specifically, the device may include an intravascular catheter made of biocompatible plastic material which contains, embedded in the catheter wall, an optical fiber that ends at or near the tip of the catheter. For example, the catheter may have a diameter of 100 μm or less. The fiber optic can be used to optically sense the presence and concentration of endogenous substances in the blood or exogenous substances injected or infused in the blood stream through the catheter lumen or another catheter. A fiber optic connector at the proximal external end of the fiber optic connects the fiber to an external monitor. In use, the needle of an injection syringe can be inserted through the catheter lumen and used to inject the indicator material (meanwhile the catheter may be allowed to remain within the vein or artery). The injection needle may be withdrawn from the catheter after injection. After the indicator has been injected and the indicator has had sufficient time to circulate through the cardiovascular system, light from a light source can be directed to the blood and circulated indicator via the optical fiber embedded in the catheter. The optical fiber of the catheter may also be used to receive light from the indicator and transmit the light to the monitor. In alternative embodiments, the catheter may include a plurality of optical fibers for transmitting and/or receiving light used to obtain measure parameters of interest of the cardiovascular system. Catheters that include optical fibers are described in U.S. Pat. Nos. 4,730,622 to Cohen and 5,217,456 to Narciso. Entire contents of these patents are incorporated by reference. In addition, other sensing devices and mechanisms may be included in the intravascular probe.

Additionally, the detection area may be arterialized during indicator emission detection. Examples of conditions resulting in detection area arterialization include, but are not limited to heating or exposure to biologically active agents which effect sympathetic system blockade (such as lidocaine).

Photodetector. The detection of indicator emissions can be achieved by optical methods known in the art. Measurement of indicator concentration can be made by administering a detectable amount of a dye indicator and using either a non-invasive, minimally invasive or intravascular procedures preferably for continuous detection. The photodetector may be positioned proximately to the detection area of the subject. The photodetector may be positioned distally or proximately to the site of the illumination source.

Fluorescent light is emitted from the indicator with the same intensity for all directions (isotropy). Consequently, in some embodiments, the emission of the dye can be detected both in "transmission mode" when the excitation light and the photodetector are on opposite sides of the illuminated tissue and in "reflection mode" when the excitation and the photodetector are on the same side of the tissue. This is advantageous over other methods at least in that the excitation light and emitted light can be input and detected from any site on the body surface and not only optically thin structures.

Photodetectors may be selected to detect the intensity and wavelength of the electromagnetic radiation emitted from the selected indicator. Photodetectors having sensitivity to various ranges of wavelengths of light are well known in the art.

In some embodiments, modifications to the system are made to further enhance the sensitivity or accuracy of the system for measuring indicator concentration. For example in some embodiments, the detection system can incorporate a lock-in detection technique. For example, the excitation light may be modulated at a specific frequency and a lock-in amplifier can be used to amplify the output of the photodetector only at that frequency. This feature is advantageous in at least that it further improves the sensitivity of the system by reducing signal to noise and allows detection of very small amounts of fluorescence emission.

In some embodiments a photomultiplier tube can be utilized as or operably connected with another photodetector to enhance the sensitivity of the system. Finally, in some embodiments, additional features, such as filters, may be utilized to minimize the background of the emission signals detected. For example, a filter may be selected which corresponds to the peak wavelength range or around the peak wavelength range of the indicator emission.

The detected electromagnetic radiation can be converted into electrical signals by a photoelectric transducing device which is integral to or independent of the photodetector. These electrical signals are transmitted to a microprocessor which records the intensity of the indicator emissions as correlated to the electrical signal for any one time point or over time. (For an example of such a device see U.S. Pat. No. 5,766,125, herein incorporated by reference.)

System Calibration

A) Minimally Invasive Calibration

The method may be minimally invasive in requiring only a single peripheral blood draw from the circulatory system to be taken for calibration purposes. Indicator concentration may be measured continuously and non-invasively using a photodetector. One blood sample from the subject may be withdrawn for calibration of the actual levels of circulating indicator with the indicator levels detected by the system. For example, a blood sample may be drawn from the subject at a selected time after the administration of the indicator into the blood stream. The blood sample may then be evaluated for the concentration of indicator present by comparison with a calibration panel of samples having known indicator concentrations. Evaluation of the indicator concentration may be made spectrophotometrically or by any other means known in the art. At subject's blood indicator concentration varying in a range of about 0.001 mg/ml to about 0.002, the concentration-fluorescence intensity curve is linear and it crosses the origin of the axes, that is the fluorescence intensity is zero when the concentration is zero. Therefore a single measurement point suffices to define the calibration curve, and no further blood samples need be taken.

B) Noninvasive Calibration

In another embodiment no blood draw is required for calibration of this system. The fluorescence of some indicators, such as ICG, does not substantially vary from patient to patient and that the skin characteristics are relatively constant for large classes of patients. Thus, the fluorescence in the blood of the patient measured from a given site on the body surface can be converted to an absolute measurement of ICG concentration, once the curve of indicator concentration vs. fluorescence is defined for that site of measurement.

Figure 11A:
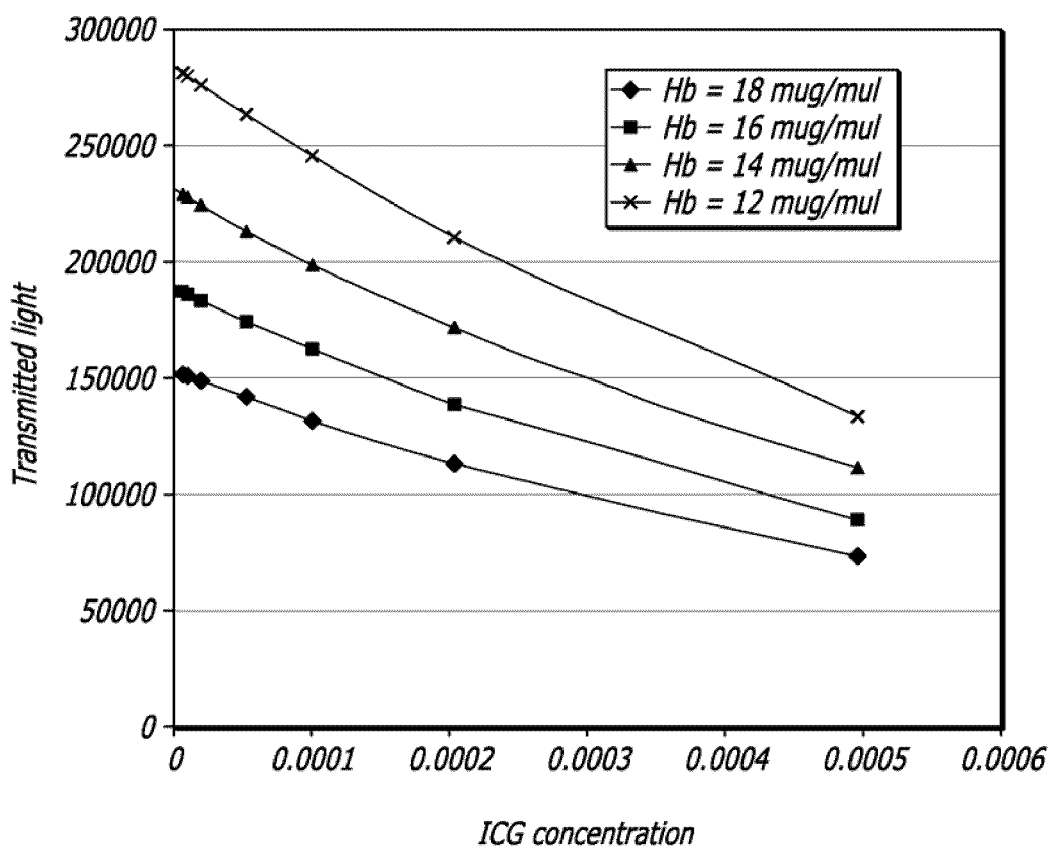
FIGS. 11A-11D are graphs showing calculated transmission and fluorescence signals at 784 nm and 830 nm for different ICG concentrations and hemoglobin contents when absorption coefficients are the same at these two wavelengths.
Figure 11B:
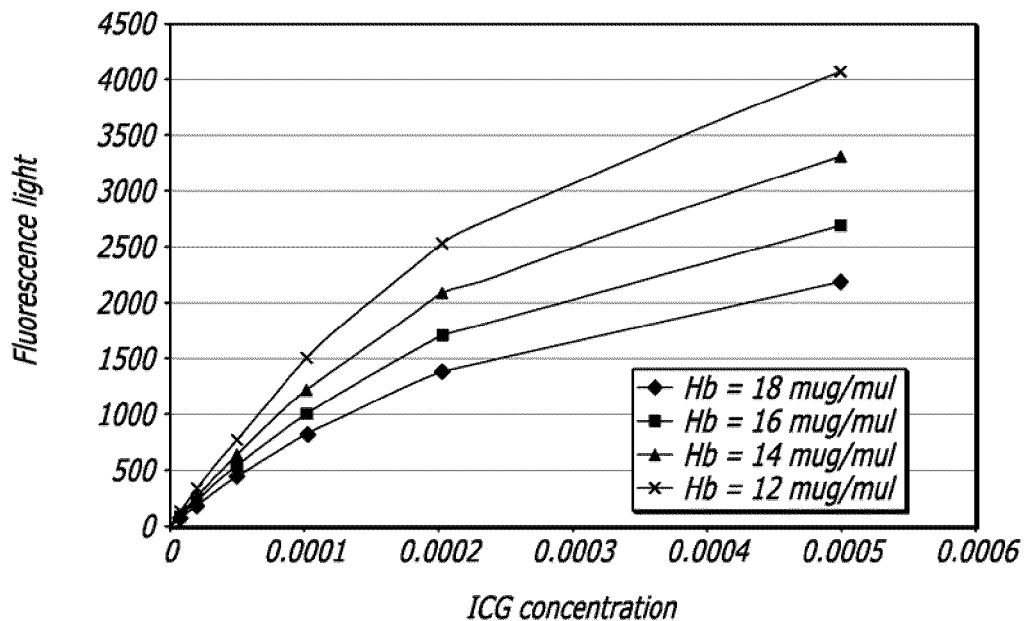
Figure 11C:
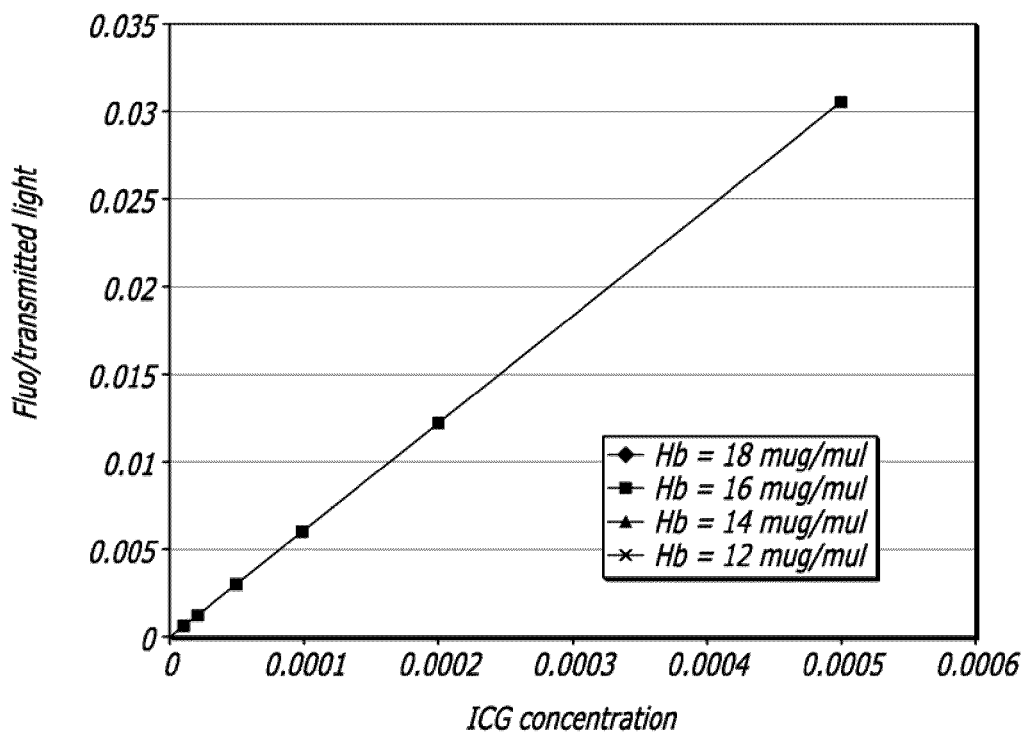

In an exemplary embodiment using the noninvasive calibration technique, the concentration of a fluorescent indicator (ICG) injected to the bloodstream can be determined without taking a blood sample. A probe (including or connected to one or several photodetectors, as described above) can measure the intensity of fluorescent light emitted by the ICG indicator when illuminated by a light source in or near the skin. The probe can also measure the intensity of the light reflected by or transmitted through the illuminated skin site. Since the ratio of emergent fluorescent light to transmitted excitation light is directly proportional to ICG concentration (see FIGS. 11A-D, FIGS. 12A-12D, and Example 3 below), the concentration of ICG can be determined from the ratio of emergent fluorescent light to transmitted excitation light. For example, the graph in FIG. 11C shows that ICG concentration is directly proportional to the ratio of fluorescent light to transmitted excitation light. In another example illustrated by the graph of FIG. 12C, ICG remains directly proportional to the ratio of fluorescent light to transmitted excitation light even when factoring the variations of absorption properties for hemoglobin (Hb) and ICG with wavelength and the absorption by bloodless tissue. While the slopes of the lines in FIG. 12C vary slightly depending upon hemoglobin content, the differences between the light ratios are relatively small. The ratios may be normalized by creating a table of coefficients that take into account various factors that may affect the light ratios (such as absorption by bloodless tissue, hemoglobin content, path length, skin color, moisture on skin surfaces, body hair, and other factors known to those skilled in the art).

The probe used to transmit and receive light may include a single optical fiber, multiple optical fibers for transmitting and/or receiving light, or other configuration known to those skilled in the art. The excitation light that is received and used in the ratio against fluorescence may be reflected and/or transmitted light. For example, in one embodiment, the light transmitter and receiver can be on the same skin surface so that the receiver can receive light reflected from the tissue. In such an embodiment, the receiving and transmitting element are the same optical fiber (See Diamond et al., "Quantification of fluorophore concentration in tissue-simulating media by fluorescence measurements with a single optical fiber;" *Applied Optics*, Vol. 42, No. 13, May 2003; the contents of which are incorporated herein by reference). In other embodiments, they may be different optical fibers (or other devices known to those skilled in the art). In such embodiments, the various optical fibers may be spatially positioned in relation to each other to optimize measurement, as described in Weersink et al. (See Weersink et al., "Noninvasive measurement of fluorophore concentration in turbid media with a simple fluorescence/reflectance ratio technique;" *Applied Optics*, Vol. 40, No. 34, December 2001; and U.S. Pat. No. 6,219,566 to Weersink et al.; the contents of both of which are incorporated herein by reference). In another embodiment, the transmitter and receiver are positioned substantially opposite each other to allow transmission of the light (such as forward scattering) from the transmitter, through the tissue, and out of the tissue to the receiver on the other side of the tissue.

C) Noninvasive Hemodialysis Probe Calibration

In another exemplary embodiment of a non-invasive calibration process of a hemodialysis process the concentration of a fluorescent indicator (ICG) injected in the bloodstream can be determined without taking a blood sample. During kidney dialysis, as fluid is removed from the vascular space, the circulating blood hematocrit increases and the blood becomes more concentrated in hemoglobin. The increase of the blood hematocrit changes the optical properties of the blood. The light absorption and light scattering increase as the density of red blood cells and the hemoglobin content of the blood increase. As the optical properties of the blood change, the relationship between the fluorescence of ICG in blood and the ICG concentration changes. This effect complicates the calibration of the fluorescence signal as a function of circulating ICG concentration in the dialyzer tubing.

Figure 13:
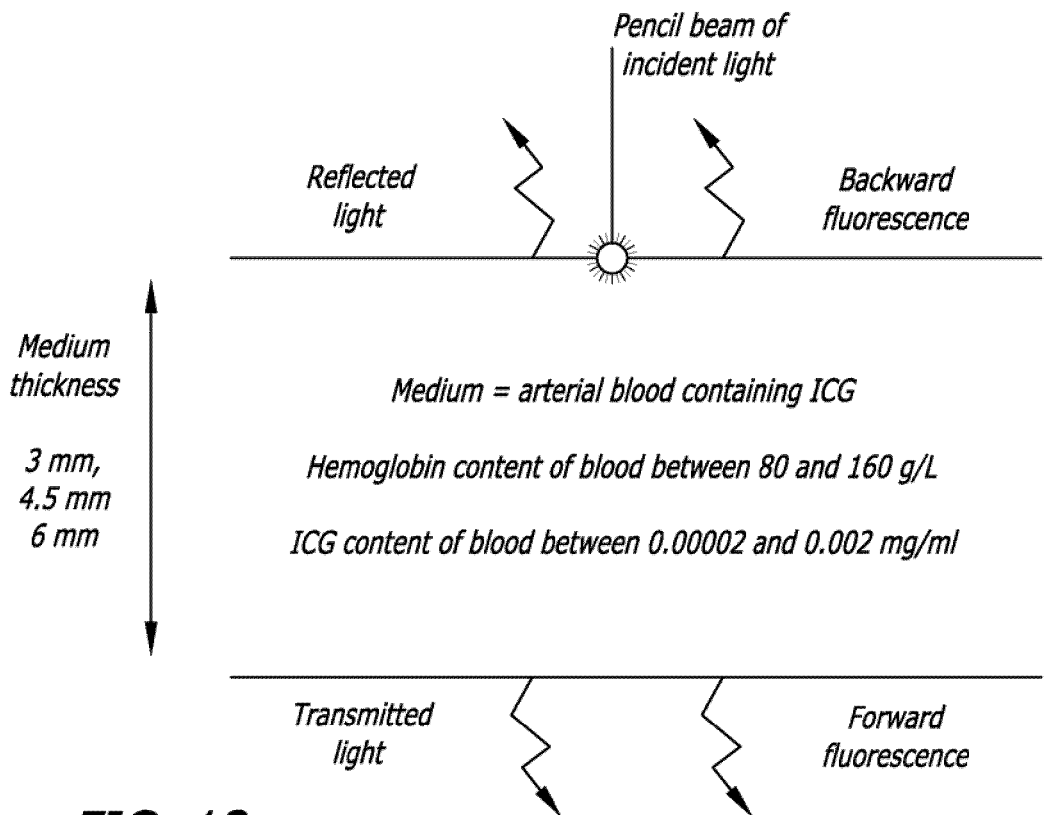
FIG. 13 is a depiction of a model used in calibration of the hemodialysis system.

To quantify these effects and find a way to calibrate the fluorescence signal, we have modeled a propagation of light in a blood slab containing ICG allowing the ICG concentration and the hemoglobin content of the blood to vary (See FIG. 13). The model study pointed to a calibration equation to derive the concentration of ICG from the fluorescence remitted from the blood medium and the transmitted light intensity across the blood medium or the light intensity reflected by the blood medium.

Model Study

The model as shown in FIG. 13 has used the Monte-Carlo method to simulate the transport of light from a pencil beam that shines on a semi-infinite slab of blood. The medium thickness is set to be 3, 4.5, or 6 mm (the dialyzer tube has a diameter of 4.5 mm). The optical properties of the blood in the slab are adjusted to match those of blood with a hemoglobin content comprised between 80 and 160 g/L, an excitation wavelength of 784 nm, and an ICG fluorescence emission wavelength of 830 nm. The blood is assumed to be fully saturated in $O_2$ (since arterial blood is pumped into the dialyzer). The blood contains ICG with a concentration between $2.10^{-5}$ µg/µL and $2.10^{-3}$ µg/µL. (the peak ICG concentration in human blood in our clinical trial is approximately $2.10^{-3}$ µg/µL when the injected ICG dose is 1 mg). The Monte Carlo program was developed following the approach of Wang et al. (Wang, L. Jacques, S L. Zheng, L. MCML—Monte Carlo modeling of light transport in multi-layered tissues. Computer Methods & Programs in Biomedicine. 47(2):131-46, 1995).

The simulation follows 1,500,000 photons as they propagate in the medium and occasionally transform into fluorescent photons. Emerging photons at the wavelength of the incident light are tabulated as a function of the distance between the point of incidence and the point of emergence on the side of the illumination beam (reflected light) and on the opposite side to the illumination beam (transmitted light). Likewise, fluorescent photons are tabulated as a function of the distance between the point of incidence and the point of emergence on the side of the illumination beam (back fluorescence) and on the opposite side (forward fluorescence). While the simulation keeps track of the angle between the direction of the emergent photons and the normal to the surface of the medium, all photons are added in the results presented in this summary which is akin to using detectors with large angles of acceptance.

We present here the results for the 4.5 mm thick blood slab. Results for the other thicknesses reflect similar behaviors. (The reflectance and back-fluorescence signals are essentially the same for the three thicknesses. The transmittance decreases as the thickness increases but the transmittance intensity can still be used to correct for changes of the back-fluorescence with hemoglobin content.)

Figure 14A:
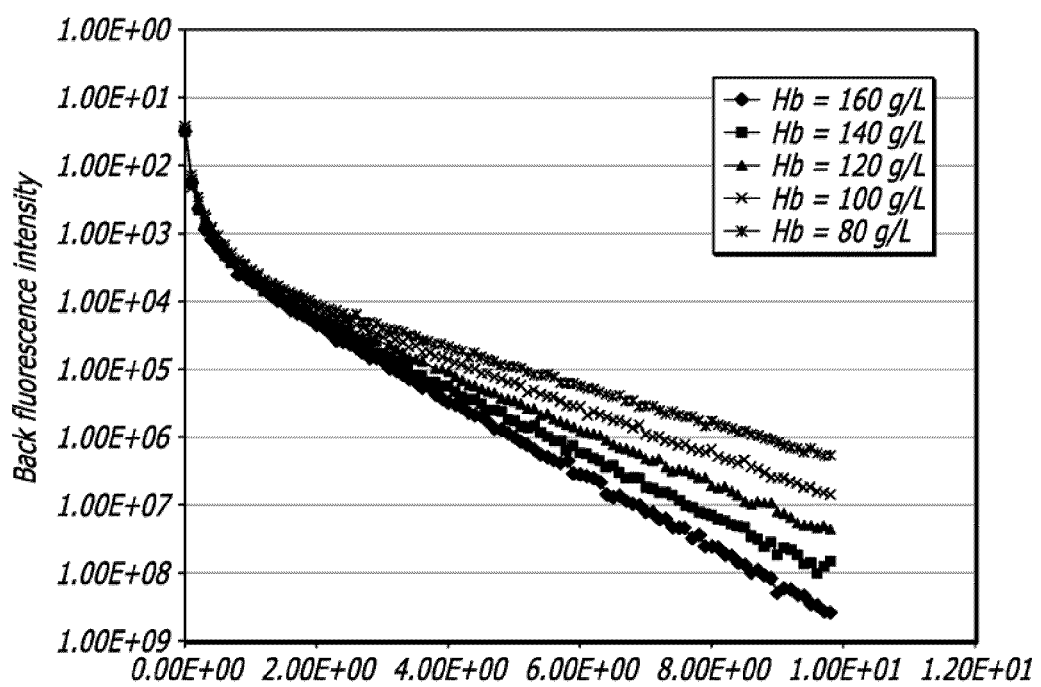
FIGS. 14A-C illustrate light intensity profiles for back-fluorescence, transmittance and reflectance for a blood ICG concentration, respectively.
Figure 14B:
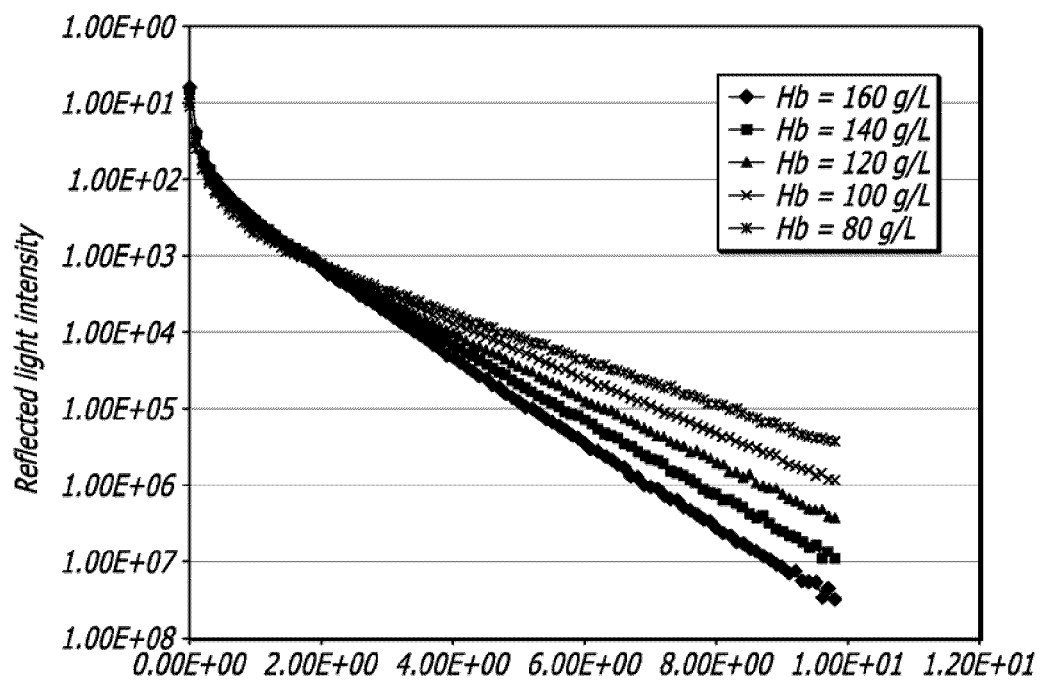
Figure 14C:
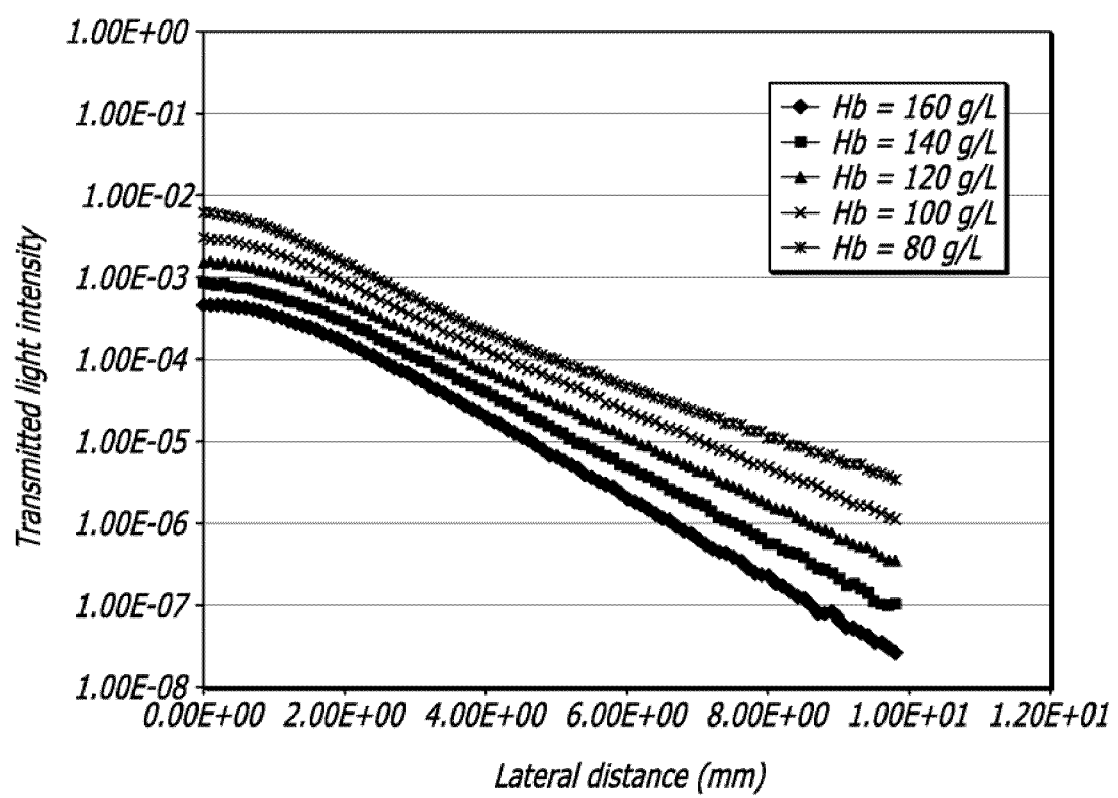

FIGS. 14*a-c* present graphs of typical light intensity profiles for the back-fluorescence, transmittance, and reflectance signals, for a blood ICG concentration of $5 \times 10^{-4}$ µg/µL. All the results are normalized to an incident light intensity of 1.

The graph of FIG. 14*a* presents the back-fluorescence intensity decreases at all distances when the blood hemoglobin content increases. As the blood hemoglobin content increases, the fluorescent light is absorbed more intensely and the back-fluorescence decreases. This is the effect that prevents us from using the same calibration equation between fluorescence and ICG concentration for all blood hemoglobin contents in the dialysis situation. We also note a linear dependence of the logarithm of the back-fluorescence signal as a function of lateral distance starting from 1.5 mm approximately from the point of entry.

The graph of FIG. 14*b* presents the reflected light intensity that is higher at short distances from the point of entry of the incident beam when the blood hemoglobin content is more elevated. At far distances from the point of entry of the incident beam, the reflected light intensity decreases when the blood hemoglobin content increases. This is interpreted considering that when the blood hemoglobin content is more elevated, light scattering is more intense. Therefore, the probability for photons to bounce out of the medium close to the point of entry is higher. Photons exiting the blood farther from the point of entry have traveled a longer distance in the blood and have been absorbed in larger amounts. The reflected light intensity decreases when absorption and scattering (blood hemoglobin content) increase. The reflected light intensity curves cross at a distance of ~1.6 mm from the point of incidence of the excitation beam. The same distance is found for the three thicknesses, all the ICG concentrations and all the hemoglobin contents tested. As for the back-fluorescence, we note a linear dependence of the logarithm of the reflected light signal as a function of lateral distance starting from 2 mm approximately from the point of entry of the incident light beam.

The graph of FIG. 14*c* presents the transmitted light signal decreases as the blood hemoglobin concentration increases for all distances from the direction formed by the incident beam, to reflect the increase in absorption and scattering of the medium. The transmitted light intensity is in the same range as the back-fluorescence when the medium thickness is 4.5 mm. This observation suggests that since we easily detect back-fluorescence from our blood calibration cell, we should also be able to detect light transmitted through 4.5 mm of blood (especially given that the quantum yield for fluorescence is assumed to be 1 in the simulations, vs. ~0.04 in reality). Again we note a linear dependence of the logarithm of the transmitted light signal as a function of lateral distance starting from 3 mm approximately from the point of entry of the incident light beam The graphs in this summary correspond to a blood ICG concentration of $5\times10^{-4}$ g/L. Similar trends noted for all ICG concentrations.

At this point, we needed to establish a calibration relationship for the back-fluorescence signal using the transmitted light. we reasoned that since the logarithm of the back-fluorescence varies linearly with lateral distance and the logarithm of the transmitted light varies linearly with lateral distance, the two quantities should vary linearly as a function of each other. Furthermore, the back-fluorescence intensity varies linearly with blood ICG concentration up to ICG concentrations of ~$10^{-3}$ µg/µL as previous simulations and empiric results have abundantly established. Consequently, the logarithm of the back-fluorescence intensity should linearly vary with the logarithm of the blood ICG concentration. Combining the two propositions, we would expect that the logarithm of the back-fluorescence satisfies a multiple linear relationship with the logarithm of the transmitted light and the logarithm of the ICG concentration.

The optical signals have been integrated (summed) over defined distance intervals from the point of entry and have performed multiple linear regression analyses considering the logarithm of the back-fluorescence signal as the dependent variable and the logarithm of the transmitted light and the logarithm of the ICG concentration as the independent variables (See results in Table 1).

away from the point of entry of the excitation light as a function of blood ICG concentration (model 1). Note that the back-fluorescence does not depend linearly on blood ICG concentration on the plot. The decrease of the transmitted light intensity with increasing blood ICG concentration acts as a correction factor which makes the linear coefficient of the ICG concentration term near 1 in the multiple linear regression analysis. Intuitively, the increase of the back-fluorescence signal intensity is not linear for elevated blood ICG concentrations because fluorescent light at 830 nm is absorbed in part by the ICG dye in the blood. The ICG dye also absorbs light at the wavelength of excitation (784 nm) which emerges across the slab and is measured as transmitted light. Because the optical properties of blood (absorption and scattering coefficients) and the absorption coefficient of ICG are similar at these two wavelengths, the effect of ICG on light transport at 830 nm and at 784 nm are similar. The absorption of the transmitted signal associated with blood ICG concentration can be used to account for the absorption of the back-fluorescence intensity with blood ICG concentration.

The traces of FIG. 14c present the back-fluorescence signal emerging near the point of entry of the light (model 2). Note that the traces appear a little more linear than those measured for a larger distance from the point of entry of the light (model 1). The effect of the blood hemoglobin content is less acute for near distances when compared to far distances of detection. The fluorescence signal intensity is about 15 times larger. Thus, there are several advantages to placing the detector measuring the back-fluorescence signal as close as possible to the incident beam.

The near transmittance signal in FIG. 14d shows similar variations to those of the far transmittance signals with respect to blood hemoglobin concentration and ICG concen-

TABLE 1

| Linear regression analysis | Model 1: optical signals integrated between 2.1 and 4 mm | Model 2: optical signals integrated between 0.2 and 2 mm (T starts at 0 mm) | Model 3: optical signals integrated between 0.5 and 2 mm (T starts at 0 mm) |
| --- | --- | --- | --- |
| Coefficient of variation, $R^2$ | 0.999 | 0.999 | 0.999 |
| Constant | 1.113 | 1.474 | 1.080 |
| Concentration Coefficient | 0.968 | 0.980 | 0.972 |
| Transmitted light coefficient | 0.516 | 0.189 | 0.198 |

The results show that the multiple linear relationships may account very well for the variations of the back-fluorescence signal ($R^2$>0.999). The coefficient of the concentration term is nearly 1, suggesting that there is a one-to-one correspondence between the back-fluorescence intensity and blood ICG concentration, once the increased opacity of the blood with increasing ICG concentration and blood hemoglobin concentration are accounted for by a decrease of the transmitted light signal. The coefficient associated with the transmitted light signal increases when the intensity of the transmitted signal decreases because of sampling farther away from the illumination axis. Measuring the optical signals near or far from the direction of entry of the light does not affect the quality of the fit or the partial one-to-one dependence of the back-fluorescence signal on blood ICG concentration.

Figure 15A:
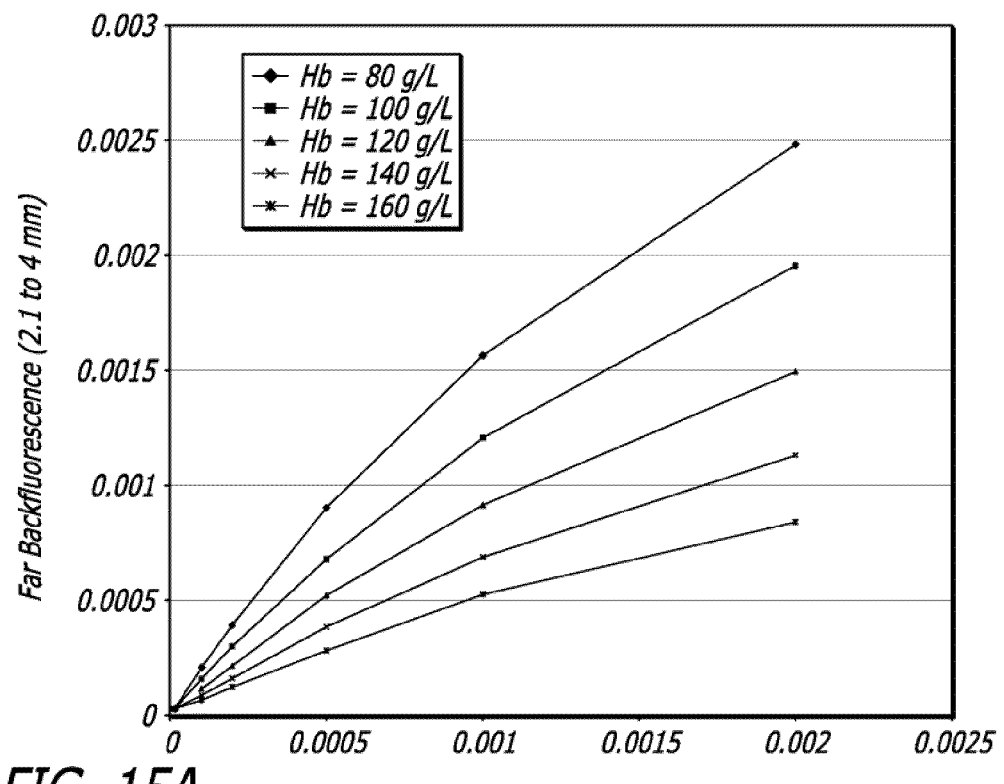
FIGS. 15A-D illustrate the plots the far back-fluorescence, far transmittance, near back-fluorescence and near transmittance signals, respectively, relative to the ICG concentration.
Figure 15B:
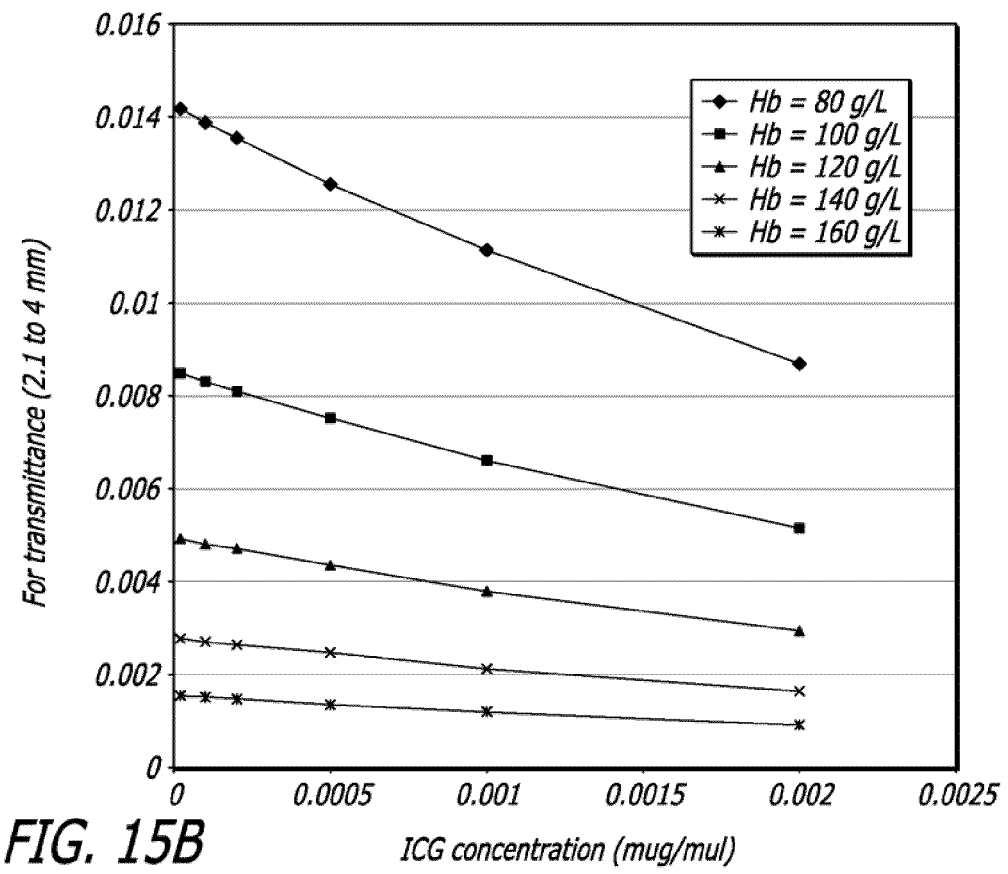
Figure 15C:
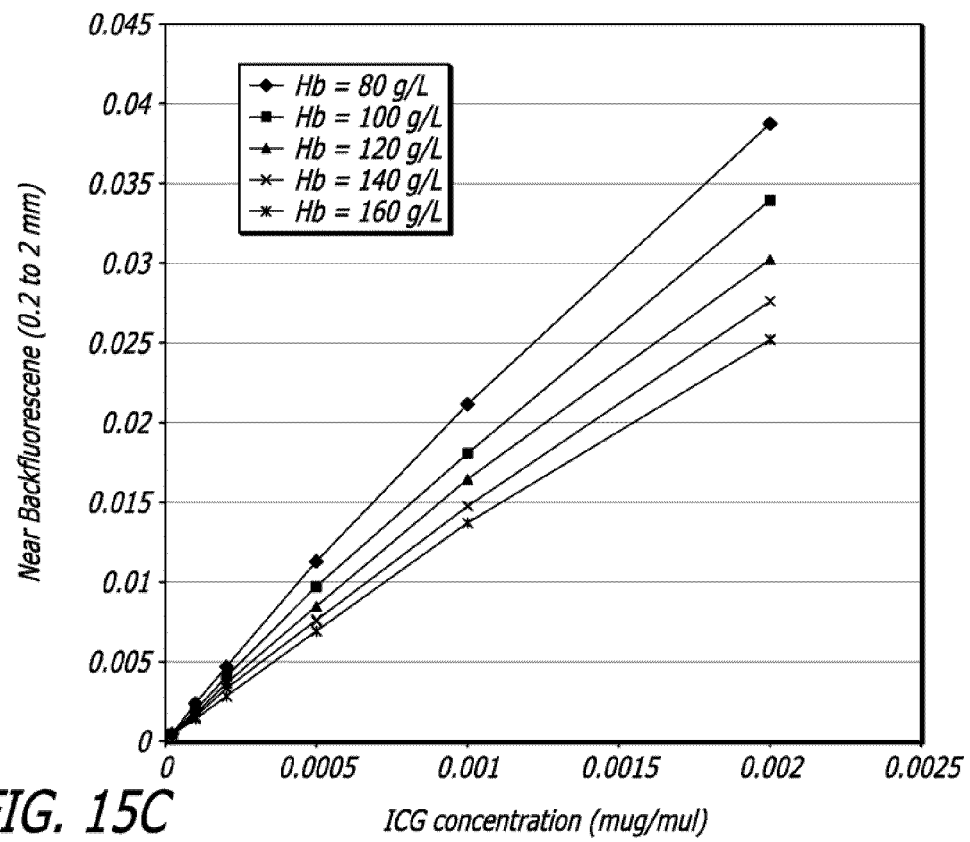
Figure 15D:
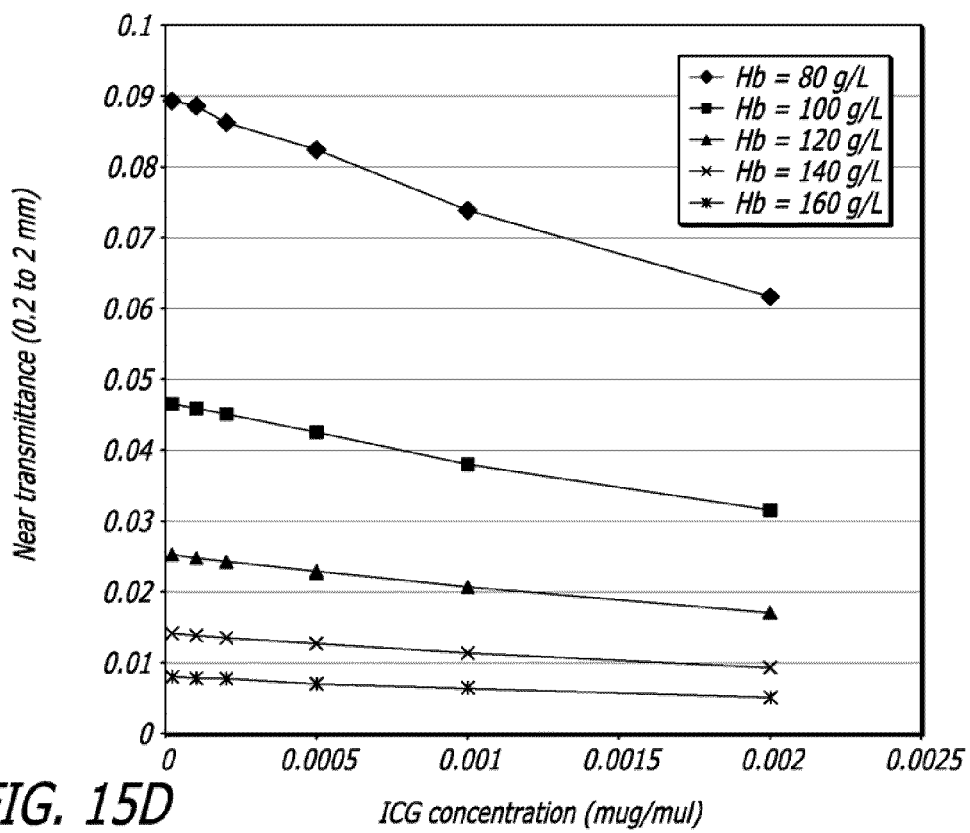

The graphs of FIGS. 15a-b show the dependence of the back-fluorescence and transmittance signals measured far tration, while being approximately 5-6 times more intense than the transmittance measured away from the direction of the incident beam.

Next, we need to establish a calibration relationship for the back-fluorescence signal using the reflected light. The reasoning presented in regard to the transmitted light also applies to the reflected light. We can expect a linear dependence of the logarithm of the back-fluorescence on the logarithm of the concentration and that of the reflected light intensity. As above, we integrated (summed) the optical signals over defined distance intervals from the point of entry and performed multiple linear regression analyses considering the logarithm of the back-fluorescence signal as the dependent variable and the logarithm of the reflected light and the logarithm of the ICG concentration as the independent variables. Three situations were tested.

TABLE 2

| Linear regression analysis | Model 4: optical signals integrated between 2.1 and 4 mm | Model 5: optical signals integrated between 0.2 and 2 mm | Model 6: back-fluorescence integrated between 0.5 and 2 mm, R between 2.1 and 4 mm |
|---|---|---|---|
| Coefficient of variation, $R^2$ | 0.999 | 0.999 | 0.999 |
| Constant | 4.668 | −0.082 | 2.764 |
| Concentration Coefficient | 1.075 | 0.936 | 1.022 |
| Reflected light coefficient | 1.975 | −0.974 | 0.820 |

We note that the coefficient of the concentration term in the multiple linear regressions is near 1. This suggests a one-to-one dependence of the back-fluorescence signal on blood ICG concentration, once the self-absorption of the fluorescence by ICG is accounted for by the variation of the reflected light. In addition, the coefficient of the reflected light is >0 when the reflected light is measured far from the point of entry of the light beam. Conversely, the coefficient of the reflected light is <0 when the reflected light is measured near the point of entry of the light beam. This result is consistent with the observation made earlier that the reflected light intensity increases near the point of entry whereas the reflected light intensity decreases away from the point of entry when hemoglobin increases (the back-fluorescence decreases for all distances when hemoglobin increases).

Based on these results, an alternate approach to account for the effect of blood hemoglobin content of the relationship between blood ICG concentration and back-fluorescence is to measure the reflected light intensity. Naturally, simultaneous measurement of the reflected and transmitted light could further specify the correction factors to use and account for this effect.

Next, we need to select of a correction approach. Using the coefficients derived from the multiple linear regression models, we compared the "experimental" back-fluorescence intensities for the different situations of the model with those predicted by the linear regression analyses.

TABLE 3

| | Model 1 | Model 2 | Model 3 |
|---|---|---|---|
| Mean relative error magnitude | 2.95% | 1.96% | 2.70% |
| Peak relative error magnitude | 10.2% | 4.28% | 7.84% |

| | Model 4 | Model 5 | Model 6 |
|---|---|---|---|
| Mean relative error magnitude | 8.36% | 4.67% | 4.40% |
| Peak relative error magnitude | 23.23% | 11.7% | 10.92% |

Figure 16:
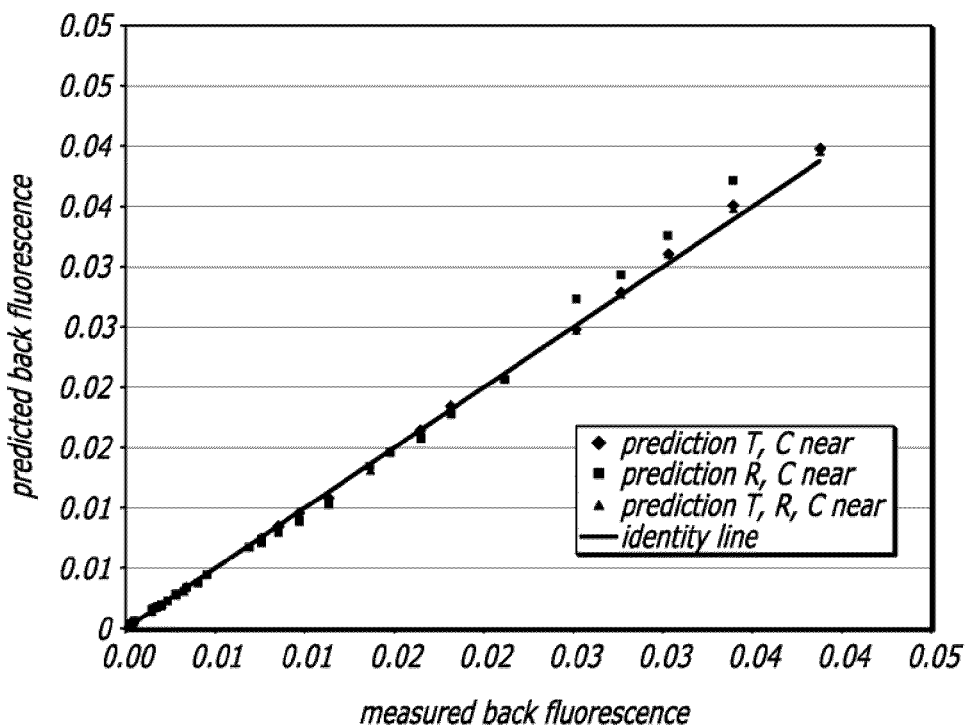
FIG. 16 illustrates the plot of predicted back-fluorescence vs. measured back-fluorescence.

The graph of FIG. 16 shows the back-fluorescence predicted by models 2 and 5 as a function of the experimental back-fluorescence. The tabulated results and the plot suggest that the correction approach that uses the transmitted light intensity is more effective at accounting for the changes of the optical properties of the medium associated with the blood hemoglobin content changes than the approach that uses reflected light, especially for the higher back-fluorescence intensities (i.e. ICG concentrations). This must be weighed against the fact that the reflected light is far more intense than the transmitted light and potentially easier to measure with respect to the probe design. Using both the transmitted and reflected light signals (yellow dots) improves the quality of the fit only marginally.

The calibration equation for model 2 reads:

$$C=10^{-1.505} \cdot T^{-0.192} \cdot B_F^{1.02}$$

Figure 17:
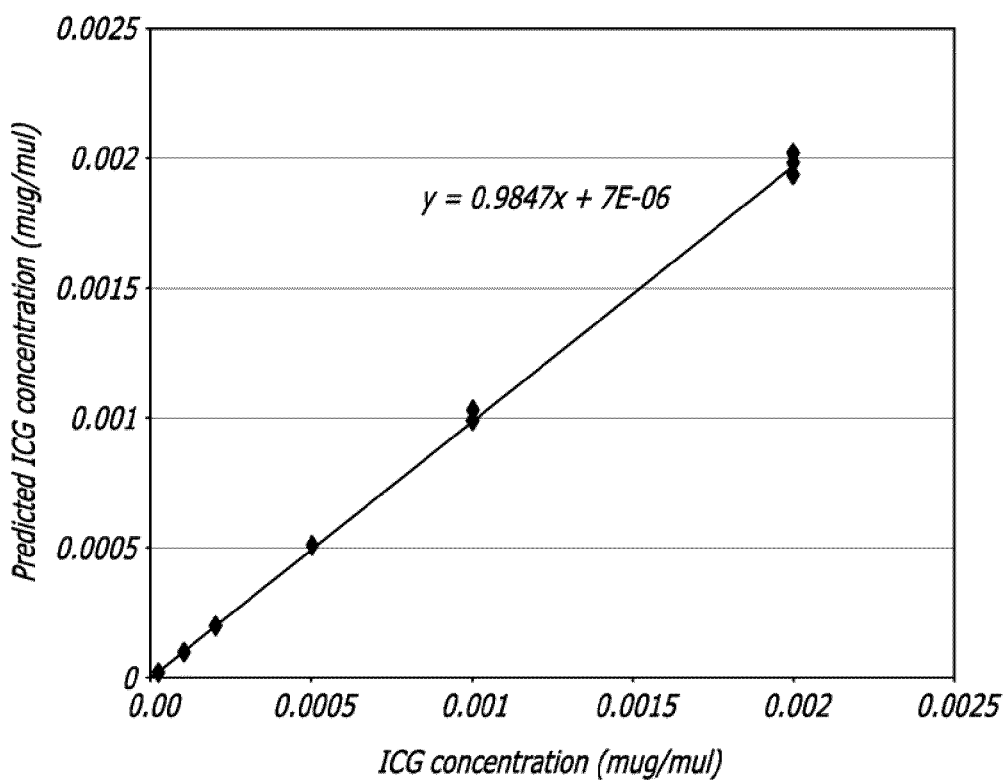
FIG. 17 illustrate the plot of the predicted ICG concentration vs. the true ICG concentration.

The relative error between predicted and real ICG concentrations=abs(C−predicted C)/C averages 0.02 and has a maximum value of 0.046 over the whole range of ICG concentrations and blood hemoglobin concentrations. The graph of FIG. 17 shows the predicted ICG concentration as a function of the true ICG concentration over the range of concentrations tested.

The results above indicate that it is possible to derive a single relationship to express the blood ICG concentration as a function of the back-fluorescence intensity and transmitted light intensity. The form of the relationship is as follows:

$$C_{ICG}=A \cdot T^{\alpha} \cdot B_{Fluo} \text{ and } C_{ICG}=K \cdot R^{\gamma} \cdot B_{Fluo}$$

Where $C_{ICG}$ is the blood ICG concentration, $B_{Fluo}$ represents the back-fluorescence intensity and T and R are the transmitted and reflected light intensities, respectively. Parameters A, K, α and γ are constants to be determined experimentally.

In addition to the above findings the study also indicated that it is possible to derive another relationship to express the blood ICG concentration such as the ICG concentration as a function of a forward-fluorescence intensity detected across the thickness of the tube and the transmitted or reflected light emitted from the medium carrying the indicator as follows:

$$C_{ICG}=B \cdot T^{\beta} \cdot F_{Fluo} \text{ and } C_{ICG}=K \cdot R^{\gamma} \cdot F_{Fluo}$$

Where $C_{ICG}$ is the blood ICG concentration, $F_{Fluo}$ represents the forward fluorescence intensity, T is the transmitted light intensity and the R is the reflected light intensity. Parameters B, K, β, γ are constants to be determined experimentally.

Experimental Validation

Figure 18:
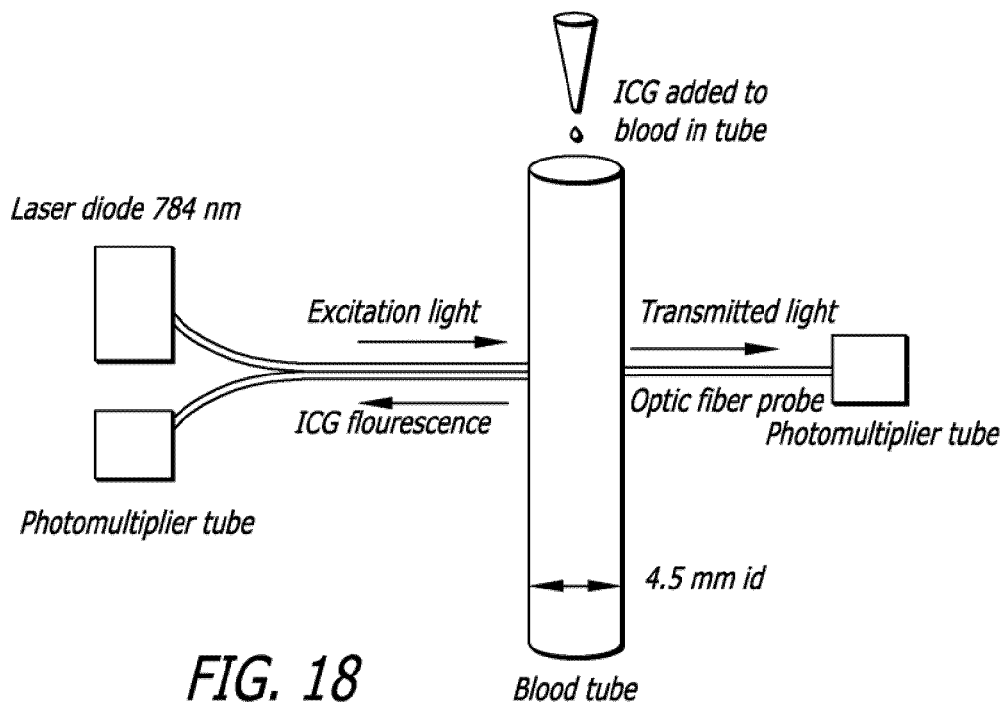
FIG. 18 is a depiction of the experimental setup used for calibration of the hemodialysis system.

The experimental validation was carried out in accordance with FIG. 18 in a segment of transparent plastic tube with diameter 4.5 mm. The tube was held snuggly in a black plastic holder in which two optical fiber probes were inserted perpendicular to the tube. The excitation/back-fluorescence probe was made of one 400 micron excitation glass fiber surrounded by six 400 micron fibers used to measure the back-fluorescence remitted by blood in the tube. The excitation fiber was coupled to the output of a laser diode emitting at 784 nm. The back-fluorescence fibers were connected to a photomultiplier tube, whose output was amplified with a lock-in amplifier. On the opposite side, the transmitted light probe was similar to the excitation/back-fluorescence probe. The six 400 micron glass fibers were connected to a second photomultiplier tube while the central 400 micron fiber was unused.

The plastic tube was closed at the bottom with a three-way stopcock that was used to insert and mix rabbit blood to varying amounts of indocyanine green. The hematocrit of the blood was varied by mixing blood from the rabbit to either plasma or red blood cells obtained by centrifugation of a second blood sample. For each level of hematocrit, the blood ICG concentration was varied between 0 and $3\times10^{-3}$ µg/µl approximately. The fluorescence and transmitted light intensities were recorded after each addition of ICG.

Figure 19:
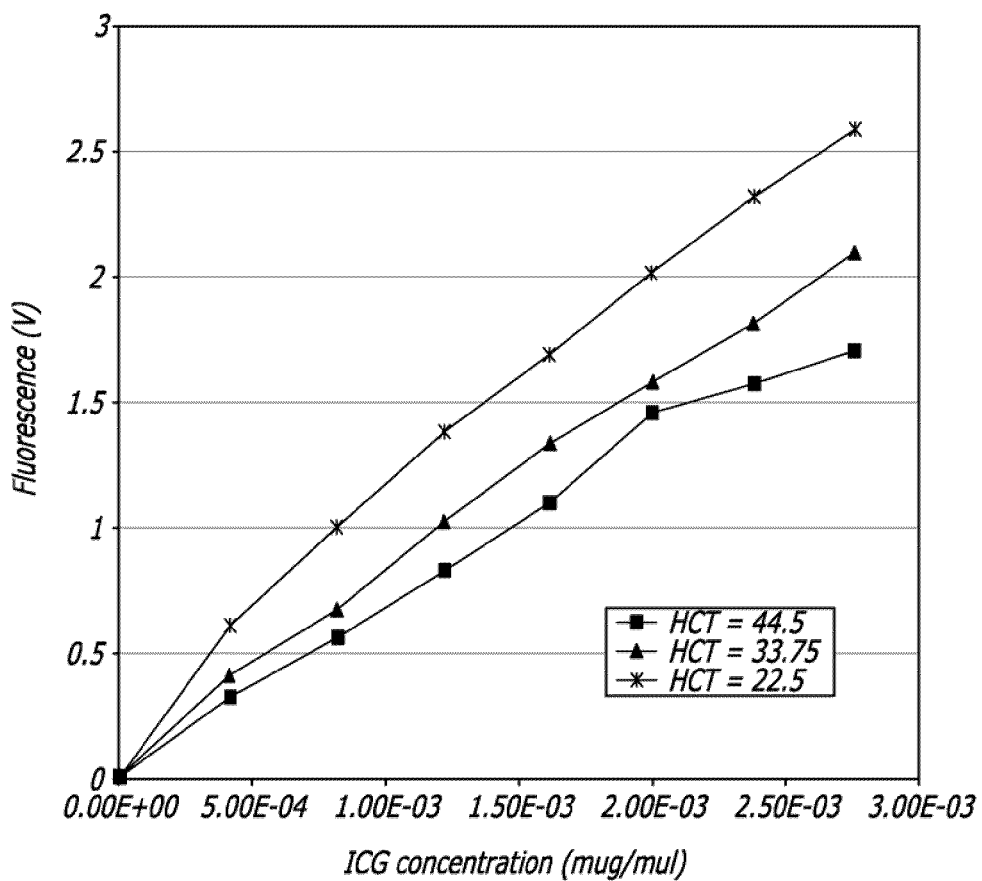
FIG. 19 is a depiction of a plot of fluorescence signal vs. ICG concentration based on multiple levels of hematocrits.

The graph of FIG. 19 shows the fluorescence recorded in one study for three levels of hematocrits. The experimental fluorescence decreases as the hematocrit increases to reflect the increased absorption of the fluorescent light by blood hemoglobin. This result is similar to that observed in the simulation study (for comparison, a hematocrit of 33.75 corresponds to a blood hemoglobin content of approximately 110 g/L)

Figure 20:
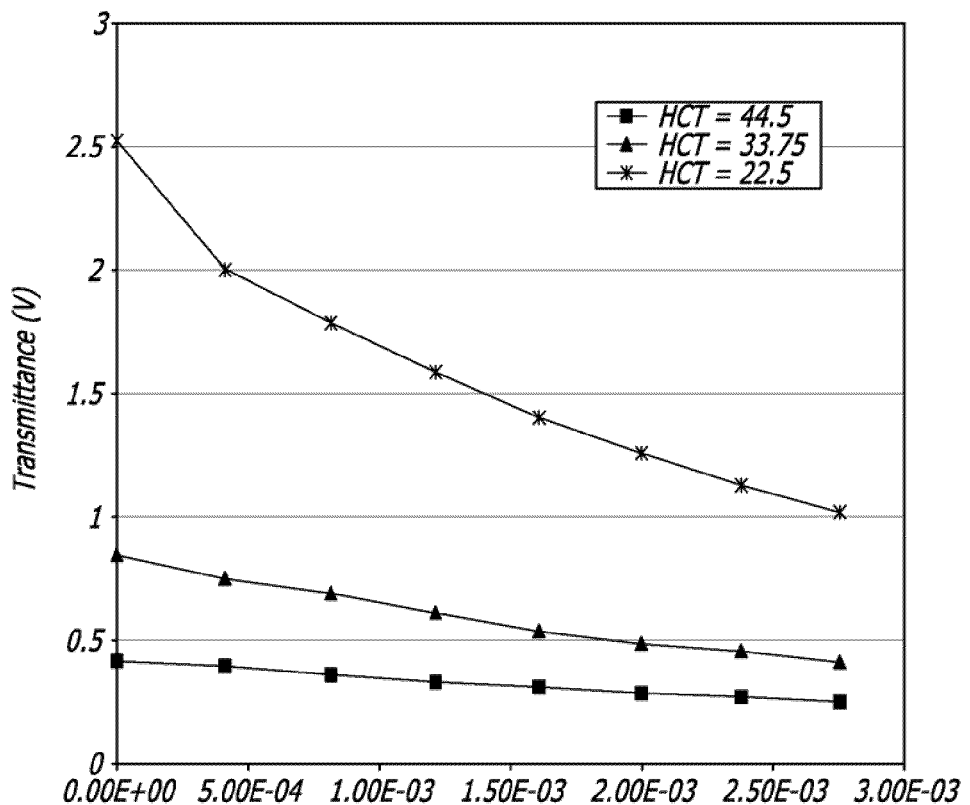
FIG. 20 is a depiction of a plot of transmittance signal vs. ICG concentration based on different levels of hematocrits.

The graph FIG. 20 shows the transmitted light intensity variations as a function of blood ICG concentration for different levels of hematocrit. Addition of ICG renders the blood more absorbent, which decreases the transmitted light. When the hematocrit is higher, the transmitted light intensity is decreased because both scattering by red blood cells and absorption by blood hemoglobin are increased. The experimental trends reflect the results of the simulation.

To validate the model, we approximated the data collected in two different experiments with the model $C_{1-ICG}=A\cdot T^{\alpha}\cdot B^{\beta}_{Fluo}$. Parameters A, α and β were selected by least squares approximation of the empirical data with those predicted by the model equation. The approximation yielded $\alpha=-0.26$, $\beta=0.97$. Parameter β was statistically not different from 1 in agreement with the predictions from the simulation study. Parameter α had sign predicted by the simulation and a numeric value in the range predicted by the simulation study. The exact value of α depends on the area over which the transmitted light intensity is collected and other experimental factors, which could not be matched exactly in the simulation study and the experiments, hence the difference between the values predicted in the simulation and our experimental results. Note also that scaling of the transmitted light or fluorescence measurements obtained by changing the gain of an amplifier or the laser intensity only affects the coefficient A without changing the power coefficients α and β.

Figure 21:
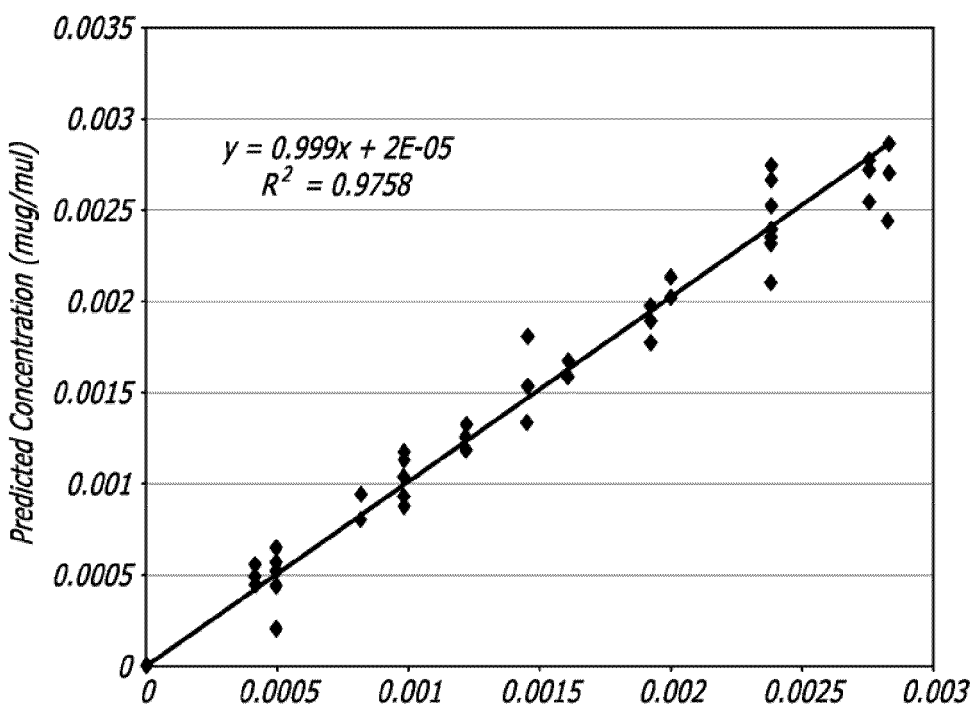
FIG. 21 is a depiction of model predicted ICG concentration vs. measured experimental ICG concentration.

The graph FIG. 21 shows the ICG concentration in blood predicted by the model as a function of the experimental ICG concentration. The regression line between the two variables is not different from the line of identity. The average quadratic error between the model prediction and the experimental ICG concentration is $10^{-4}$ µg/µl. This error corresponds to ~5% of the peak concentration observed clinically during cardiac output fluorescence dilution measurements when the injected ICG dose is 1 mg.

We have established through computer simulations and verified experimentally that the ICG concentration in blood can be estimated by measuring the fluorescence intensity of the ICG and the light intensity transmitted through the container of the blood.

This calibration method can be used to calculate the ICG concentration in blood flowing through the dialyzer tube during kidney dialysis. The calibration method corrects for changes in the blood hematocrit or hemoglobin content between different subjects or within the same subject as hematocrit changes during the dialysis.

When transmitted light intensity (T) and fluorescence intensity ($B_{Fluo}$) are measured, the calibration equation is of the form $C_{ICG}=A\cdot T^{\alpha}\cdot B_{Fluo}$ where α is constant, once the conditions of measurement of the transmitted light intensity (acceptance angle, detection area) are set. Parameter A depends on experimental factors such as the intensity of the excitation light.

The computer simulations predict a similar equation $C_{ICG}=K\cdot R^{\gamma}\cdot B_{Fluo}$ when the reflected light intensity (R) and fluorescence intensity ($B_{Ruo}$) are measured. In this equation, exponent γ is constant, once the conditions of measurement of the reflected light intensity (acceptance angle, detection area) are set. Parameter K depends on experimental factors.

The simulations provide indications about the design of the probe used to measure the fluorescence and transmitted light intensities: 1) Use fibers with large acceptance angles to capture as much light as possible, 2) Measure the back-fluorescence intensity as close as possible to the point of entry of the incident light. Covering approximately a 1 mm ring around the point of entry captures the most intense back-fluorescence signal, 3) Measure the transmitted light signal over approximately a 1 mm ring across from the point of entry of the incident light beam, 4) Using a probe that measures both the transmitted and reflected light signals could further improve the quality of the correction.

These methods and systems may be utilized to measure several cardiovascular parameters. Once the system has been calibrated to the subject (where necessary) and the indicator emissions detected and recorded over time, the computing system may be used to calculate cardiovascular parameters including cardiac output and blood volume.

Cardiac output calculations. In some embodiments, the cardiac output can be calculated using equations which inversely correlate the area under the first pass indicator emission curve (magnitude of intensity curve) with cardiac output. Cardiac output is typically expressed as averages (L/min). The general methods have been previously described (Geddes, supra, herein incorporated by reference).

Classically, the descending limb of the curve is plotted semi-logarithmically to identify the end of the first pass of indicator. For example, the descending limb of the curve may be extrapolated down to 1% of the maximum height of the curve. The curve can then be completed by plotting values for times preceding the end time. Finally, the area under this corrected curve is established and divided by the length (time) to render a mean height. This mean height is converted to mean concentration after calibration of the detector. The narrower the curve, the higher the cardiac output; the wider the curve, the lower the cardiac output. Several variations of this calculation method are found, including methods that fit a model equation to the ascending and descending portions of the indicator concentration curve.

Depending upon the indicator type and dosage selected, the curve may not return to zero after the end of the first pass due to a residual concentration of indicator re-circulating in the system. Subsequent calculations of cardiac output from the curve may then account for this recirculation artifact by correcting for the background emissions, prior to calculating the area under the curve.

Sequential measurements of a cardiovascular circulatory parameter, such as cardiac output or blood volume, may be taken. Each measurement may be preceded by the administration of an indicator to the cardiovascular system. Each measurement may be separated by a time period during which the indicator that was previously administered is substantially eliminated from the circulatory system, for instance by metabolic processes.

To obtain a measurement in absolute physical units, e.g., in liters per minute for cardiac output or liters for blood volume, a blood sample may be taken after each administration of the indicator for calibration purposes, as explained in more detail above.

Another approach may be to take a blood sample only after the first administration of the indicator and to use this blood sample for calibration purposes during each subsequent administration of the indicator and measurement of its resulting fluorescence. However, the operating characteristics of the test equipment may shift during these tests. The optical properties of the tissue being illuminated may also change. The positioning of the illumination source and/or the photo detector may also change. All these changes can introduce errors in the computation of the parameter in absolute physical units when the computations are based on a blood sample that was taken before the changes occurred.

These errors may be minimized by measuring the changes that occur after the blood sample is taken and by then adjusting the measured fluorescence intensity to compensate for these measured changes. This may be accomplished by measuring the intensity of the illumination light after it is transmitted through or reflected by the tissue through which the administered indicator passes. This illumination intensity measurement may be made shortly before, during or shortly after each administration of the indicator. The computations of the cardiovascular parameter that are made during tests subsequent to the first test (when the calibrating blood sample was taken) may then be adjusted in accordance with variations in these illumination intensity measurements.

For example, the computation of the cardiovascular parameter that is made following the second administration of the indicator may be multiplied by the ratio of the illumination intensity measurement made prior to the first administration of the indicator to the illumination intensity measurement made prior to the second administration of the indicator. If the illumination intensity between the first and second measurements doubles, for example, application of this formula may result in a halving of the computation. Other functional relationships between the measured cardiovascular parameter and the illumination intensity measurements may also be implemented.

Any equipment may be used to make the illumination intensity measurements. In one embodiment, the photo detector that detects the fluorescence intensity may also be used to make the illumination intensity measurements. The optical filter that removes light at the illumination frequency may be removed during the illumination intensity measurements. The leakage of the illumination thought this filter may instead be measured and used as the information for the computation.

Another approach to minimizing the number of needed blood samples for a sequence of tests is to take advantage of the known relationship between the amount of indicator that is injected, the volume of blood in the circulatory system and the resulting concentration of the indicator in that blood.

One step in this approach is to determine the volume of blood in the cardiovascular circulatory system using any technique, such as a tracer dilution technique, applied for instance with the Evans Blue dye. The concentration of the indicator after it is administered and mixed throughout the total blood volume, with no offset for metabolic elimination, may then be computed by dividing the amount of the indicator that is administered by the volume of the blood.

Figure 10:
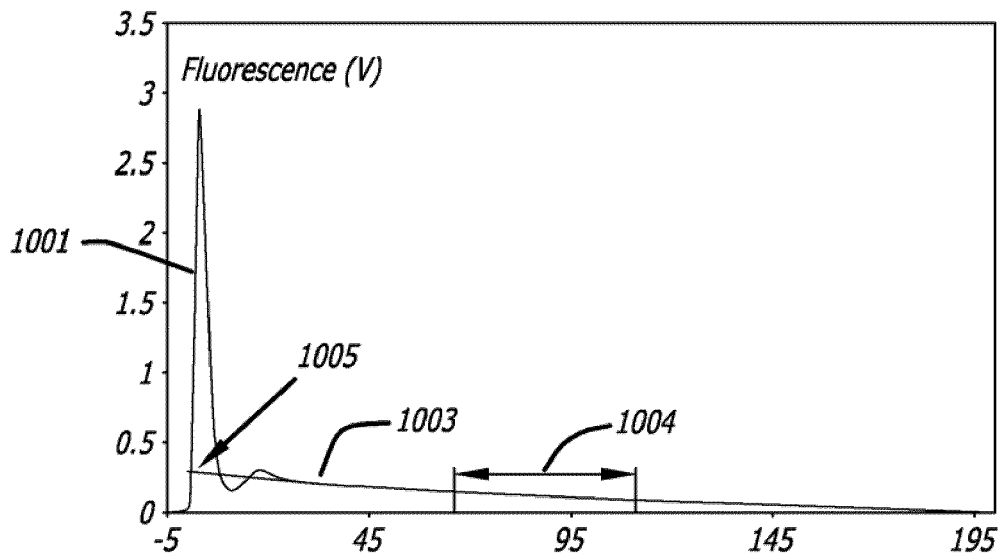
FIG. 10 illustrates a fluorescence intensity curve that includes an extrapolation that intercepts the point on the curve at which the fluorescence is indicative of the concentration of the indicator when mixed throughout the volume of blood of the subject.

The theoretical magnitude of the intensity of the fluorescence from the indicator after the indicator is mixed throughout the total blood volume, without having been metabolized or otherwise eliminated from the circulatory system, may then be determined from the fluorescence curve. FIG. 10 illustrates one way that this may be done. As shown in FIG. 10, the intensity of the fluorescence of an administered indicator will often rise quickly after the injection, as illustrated by a sharply rising portion 1001. The intensity may then decay slowly, as illustrated by a slowly falling portion 1003. A portion of the curve 1004 during the slow decay may be extrapolated until it intercepts a point 1005 on the fast rising portion. The level of the intensity of the fluorescence at the point 1005 may represent the concentration of the indicator after it is administered and mixed throughout the total blood volume, with no offset for metabolic elimination, i.e., the concentration of the indicator that was computed above.

Based on this extrapolated point, a conversion factor may then be determined that converts the measured intensity of the fluorescence to the concentration of the indicator in the cardiovascular system. The conversion factor may be determined by equating it to the ratio of the concentration of the indicator that was calculated above to the measurement of the intensity of the fluorescence at the intercepted point. The concentration of the indicator at other points on the fluorescence intensity curve shown in FIG. 10 may then be computed by multiplying the measured fluorescence intensity value by the conversion factor.

Subsequent administrations of indicator may be made and measured to monitor the cardiovascular parameter over short or long periods of time. The same computational process as is described above may be used each time to determine the absolute physical value of the desired cardiovascular parameter without having to again take a blood sample. The process may also intrinsically compensate for changes between measurements, other than changes in blood volume, such as changes in the operating characteristics of the test equipment, the optical properties of the tissue being illuminated, and/or the positioning of the illumination source and/or the photo detector.

All of the foregoing computations, as well as others, may be automatically performed by a computing system. The computing system may include any type of hardware and/or software.

Results obtained using this system can be normalized for comparison between subjects by expressing cardiac output as a function of weight (CO/body weight (L/min/kg)) or as a function of surface area (cardiac index=CO/body surface area (L/min/m$^2$)).

Blood volume calculations. In some embodiments, blood volume may be measured independently or in addition to the cardiac output. General methods of measuring blood volume are known in the art. In some embodiments, circulating blood volume may be measured using a low dose of indicator which is allowed to mix within the circulatory system for a period of time selected for adequate mixing, but inadequate or the indicator to be completely metabolized. The circulating blood volume may then be calculated by back extrapolating to the instant of injection the slow metabolic disappearance phase of the concentration curve detected over time (Bloomfield, D.A. Dye curves: The theory and practice of indicator dilution. University Park Press, 1974). Alternative methods of calculation include, but are not limited to those described in U.S. Pat. Nos. 5,999,841, 6,230,035 or 5,776,125, herein incorporated by reference.

This method and system may be used to examine the general cardiovascular health of a subject. In one embodiment, the method may be undertaken one time, such that one cardiac output and or blood volume measurement would be obtained. In other embodiments, the method may be undertaken to obtain repeated or continuous measurements of cardiovascular parameters over time. Further, repeated measures may be taken in conditions where the cardiovascular system is challenged such that a subject's basal and challenged cardiovascular parameters can be compared. Challenges which may be utilized to alter the cardiovascular system include, but are not limited to exercise, treatment with biologically active agent which alter heart function (such as epinephrine), parasympathetic stimulation (such as vagal stimulation), injection of liquids increasing blood volume (such as colloidal plasma substitutes) or exposure to enhanced levels of respiratory gases.

Figure 1:
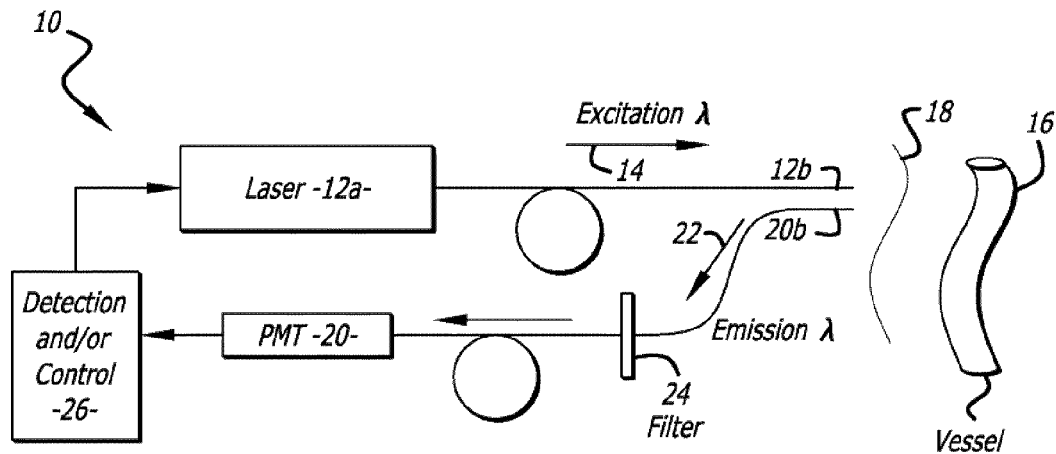
FIG. 1 is a diagrammatic depiction of an example of one embodiment of an exemplary cardiac output measurement system.
Figure 2:
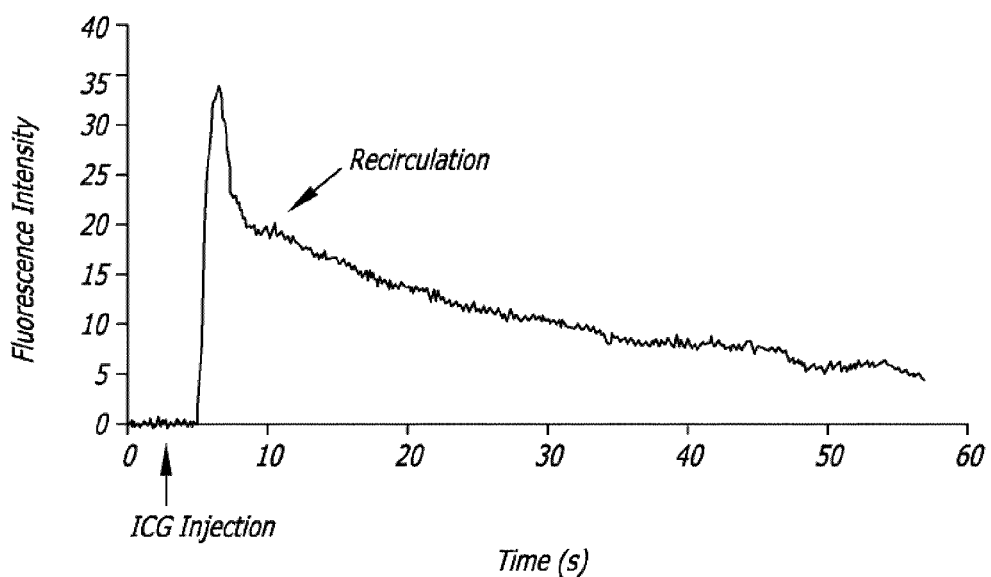
FIG. 2 is a fluorescence intensity curve generated using one embodiment of the cardiovascular measurement devices and methods.
Figure 3:
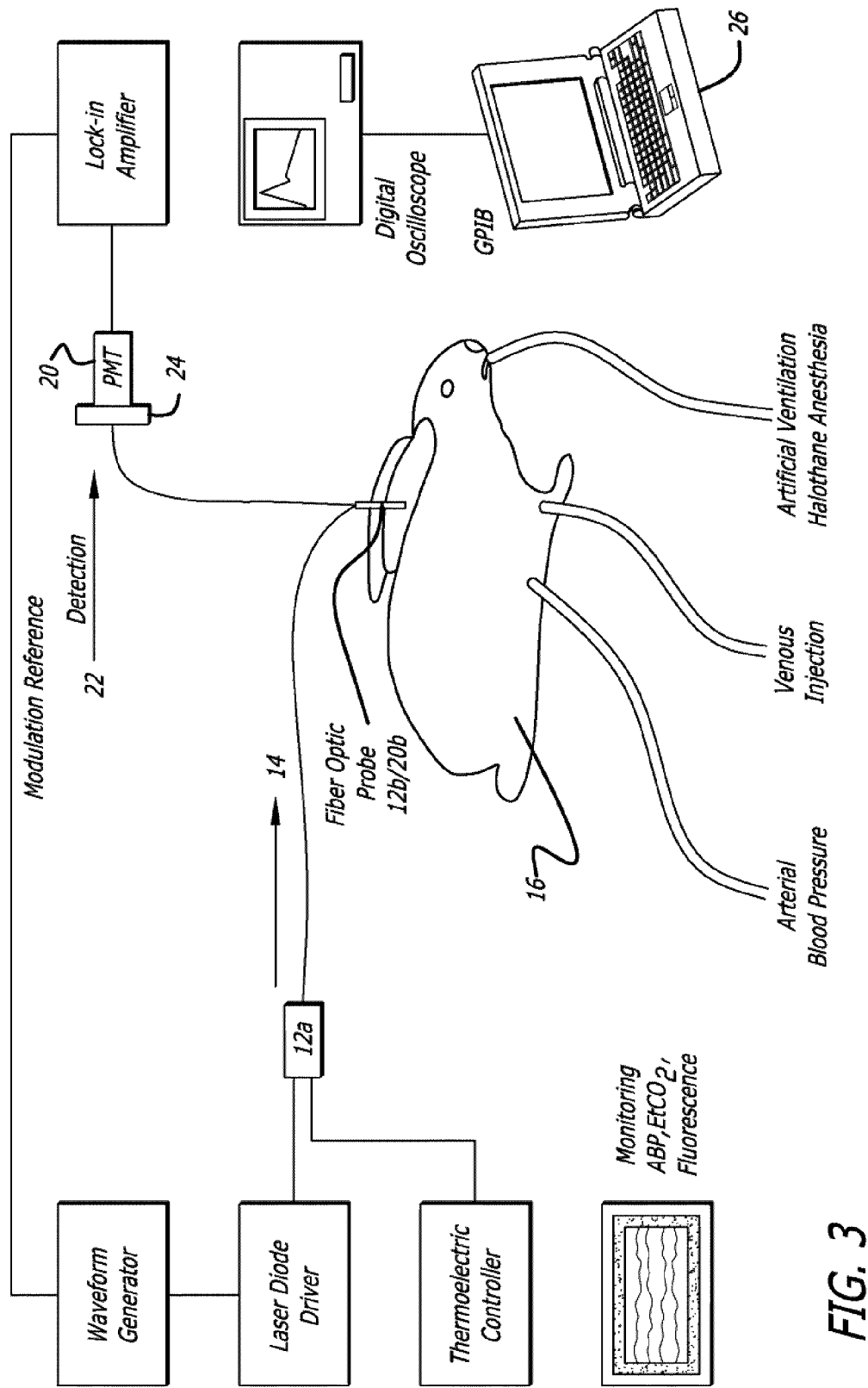
FIG. 3 is a diagrammatic depiction of an example of one embodiment of the cardiovascular measurement device having a photodetector positioned on the ear skin surface.

A schematic of one embodiment of an exemplary system 10 is shown in FIG. 1. The system comprises an illumination source 12 here a 775 nm laser selected to emit a excitation wavelength of light 14 which maximally excites ICG, the indicator selected. Here the illumination source 12 is positioned proximately to the subject 16, such that the excitation wavelength of light 14 is shone transdermally onto the indicator circulating in the bloodstream. The system also comprises a photodetector 20 placed in proximity to the subject's skin surface 18 for detection of the indicator emission wavelength 22. Optionally, a filter 24 may be used for isolating the peak wavelength at which the indicator emits, being about 830 nm. Finally, the photodetector 20 is operably connected to a microprocessor 26 for storing the electronic signals transmitted from the photodetector 20 over time, and generating the indicator concentration curve (FIG. 2). Optionally, the microprocessor 26 may regulate the illumination source to coordinate the excitation and detection of emissions from the indicator, for example using a modulation technique. The microprocessor may also comprise software programs for analyzing the output obtained from the detector 20 such that the information could be converted into values of cardiac output or blood volume, for example and/or displayed in the form of a user interface.

In order to demonstrate the utility of cardiovascular measurement devices and methods, a non-invasive indicator detection system 10 was used to repeatedly monitor cardiac output. With reference to FIG. 1, a fiber optic 12b transmitted light from illumination source 12a to the subject's skin 18. A second fiber optic 20b, positioned near the skin 18 transmitted the emitted light to a photodetector 20. The indicator was intravenously injected. A body portion which included blood vessels near the surface of the skin was irradiated with a laser. A characteristic fluorescence intensity/concentration curve was obtained upon excitation with laser light at about 775 nm and detection of the fluorescence at about 830 nm. From this information cardiac output and blood volume for the subject was calculated.

The system used for this method may comprise a variety of additional components. For example, non-invasive detection is described for monitoring of indicators within the circulatory system of the patient. Modifications of the detectors to accommodate to various regions of the patient's body or to provide thermal, electrical or chemical stimulation to the body are envisioned within the scope of cardiovascular measurement devices and methods. Also, calibration of the system may be automated by a computing system, such that a blood sample is drawn from the patient after administration of the indicator, concentration detected and compared with known standards and/or the emission curve. Also, software may be used in conjunction with the microprocessor to aid in altering parameters of any of the components of the system or effectuating the calculations of the cardiovascular parameters being measured. Further, software may be used to display these results to a user by way of a digital display, personal computer or the like.

Hemodialysis Applications. In an exemplary embodiment, the measurement of the fluorescence dilution trace may be performed by placing the illumination and detection probe on the skin surface at the level of the AV fistula or AV shunt, on the proximal side of the fistula or shunt. Injection of the fluorescent dye may be performed through a fine needle inserted at the distal end of the fistula in venous blood returning toward the right heart. The abundant blood flow through the fistula or shunt carries the dye toward the central circulation where it mixes and gives rise to dye dilution profile that can be detected by illuminating the dye transcutaneously at an appropriate wavelength to excite its fluorescence. Analysis of the fluorescence dilution profile may be performed to estimate the cardiac output and circulating blood volume. This procedure can be operated before, during, and/or after the dialysis procedure without delaying or compromising the procedure. The patient may be monitored during the hemodialysis procedure by comparing the estimated parameters (i.e. cardiac output or circulating blood volume) to the parameters obtained before the procedure. This way the rate of fluid removal from the patient can be controlled if for example any one of cardiac output or circulating blood volume parameters changes significantly. If the measurement is performed during the dialysis procedure with blood flowing through the dialyzer, the estimated volume can include that of the blood compartment in the dialyzer, which may be subtracted to determine the patient's circulating blood volume. Cardiac output, which can be estimated from the first pass dilution curve, may not depend on whether the test is performed during the dialysis procedure.

In another exemplary embodiment, the illumination and detection probe may be attached on the external wall of the transparent tubing transporting blood from the artery to the dialyzer, or alternatively attached to the wall of a special fitting that inserts on the blood path from the patient's artery to the dialyzer as configured in an alternative embodiment of FIGS. 22A-C. Injection of the dye in the venous blood stream may be performed through a side port in the venous connection returning the dialyzed blood to the patient, through a fine needle inserted in the AV fistula or shunt or through a catheter inserted in another vein of the subject, for instance the antecubital vein. FIG. 22A represents the front view of the hemodialysis probe. The probe includes the probe body 2209 and the communication module 2201. The tubing 2207 having blood running out of the patient's body into the dialyzer is illuminated through the line 2202 by laser illumination. The lines 2203 and 2204 represent back-fluorescence intensity and reflected light intensity, respectively. The lines 2205 and 2206 represent the forward-fluorescence and transmitted light, respectively. FIGS. 22B and 22C represent the oblique and side views, respectively, of the probe. The communication module 2201 controls the illumination and receiving of emitted light intensities.

Such implementations may simplify the calibration procedure, which can be performed in-vitro in a blood loop system to characterize the light transmission and fluorescence detection characteristics of the fittings as discussed above with respect to the non-invasive calibration. While the probe configuration is presented as shown in FIGS. 22A-C and discussed above, applicant's probe is not limited to the probe of FIGS. 22A-C. Alternative embodiments of the probe's configurations are within the scope of the applicant's invention. An ordinary practitioner in this field would use the most appropriate configuration of the probe for a given application.

As discussed above the following relationships together or interchangeably can be used to determine the ICG concentration of blood during hemodialysis procedure:

$$C_{ICG} = A \cdot T^{\alpha} \cdot B_{Fluo} \text{ and } C_{ICG} = K \cdot R^{\gamma} \cdot B_{Fluo}$$

Where $C_{ICG}$ is the blood ICG concentration, $B_{Fluo}$ represents the back-fluorescence intensity and T and R are the transmitted and reflected light intensities, respectively, and parameters A, K, $\alpha$, $\gamma$ are constants that are determined experimentally; and the relationships:

$$C_{ICG} = B \cdot T^{\theta} F_{Fluo} \text{ and } C_{ICG} = K \cdot R^{\gamma} \cdot F_{Fluo}$$

Where $C_{ICG}$ is the blood ICG concentration, $F_{Fluo}$ represents the forward fluorescence intensity, T is the transmitted light intensity and the R is the reflected light intensity and the parameters B, K, β, γ are constants that are determined experimentally.

This implementation may also provide an improved signal-to-noise ratio since there is no attenuation of the excitation light and fluorescence by biologic tissue. As a result, the amount of injected ICG can be reduced several fold compared to that used for detection through the skin in humans (typically 1 mg or larger). As a result, the measurements of cardiac output can be repeated frequently (~5 min) after the dye is metabolized by the liver.

Typically, more than 95% of ICG injected in the bloodstream binds to blood proteins such that the protein-bound ICG is not cleared by the dialysis procedure. Unbound ICG (MW 775) is too large to be efficiently cleared by the dialyzer. Thus, there may be no artifact or impediment in implementing such measurements during dialysis.

Furthermore, the venous injection of the ICG could be made through any large peripheral vein and does not necessarily have to be at the venous side of the AV fistula. Likewise, detection of the fluorescence dilution trace does not necessarily have to take place at the level of the AV fistula or shunt, and may occur at any site on the body surface (such as the ear lobe or the wing of the nose) if the site is well perfused and/or arterialized by local heating.

The utility of the cardiovascular measurement devices and methods is further illustrated by the following examples, which are not intended to be limiting.

EXAMPLE 1

Experimental system and method. An implementation of the system and method of the cardiovascular measurement devices and methods was tested in rats. The excitation source was a 775 nm pulsed diode laser and the fluorescence was detected with a detector being a photomultiplier tube (PMT) with extended response in the near-infrared range of the spectrum (FIG. 1). Optic fibers were placed in close contact with the skin of the animal's ear for the excitation and detection of the indicator within the blood stream. After injection of a 100 µl bolus of ICG (0.0075 mg/ml) into the jugular vein of a rat, the fluorescence intensity trace (indicator concentration recording) was measured transcutaneously at the level of the rat's ear using reflection mode detection of emissions (FIG. 2).

Calculation of blood volume and cardiac output. The initial rapid rise and rapid decay segments of the fluorescence intensity trace represent the first pass of the fluorescent indicator in the arterial vasculature of the animal. Such a waveform is characteristic of indicator dilution techniques. This portion of the recording is analyzed with one of several known algorithms (i.e. Stewart Hamilton technique) to compute the "area under the curve" of the fluorescence intensity trace while excluding the recirculation artifact. Here, the initial portion of the fluorescence trace y(t) was fitted with a model equation $y(t)=y_0 t^\alpha \exp(-\beta t)$ which approximates both the rising and descending segments of the trace. This equation derived from a "tank-in-series" representation of the cardiovascular system has been found fit well the experimental indicator dilution recordings. The numerical parameters of the fit were determined from the approximation procedure, and then the "area under the curve" was computed by numeric integration and used to find the cardiac output with the known formula:

$$Q = \frac{m}{\int_0^\infty C(t)dt} = \frac{\text{amount injected}}{\text{area under the curve}}$$

Back extrapolation of the slow decay segment of the fluorescence intensity trace to the instant when ICG is first detected in the blood (time 0) yields the estimated concentration of ICG mixed in the whole circulating blood volume. By dividing the amount of injected ICG by this extrapolated ICG concentration at time 0, the circulating blood volume was computed.

Calibration methods. Indicator concentration C(t) was computed from the fluorescence y(t) using one of two calibration methods. Transcutaneous in vivo fluorescence was calibrated with respect to absolute blood concentrations of ICG, using a few blood samples withdrawn from a peripheral artery after bolus dye injection of ICG. The blood samples were placed in a fluorescence cell and inserted in a tabletop fluorometer for measurement of their fluorescence emission. The fluorescence readings were converted into ICG concentrations using a standard calibration curve established by measuring with the tabletop fluorometer the fluorescence of blood samples containing known concentrations of ICG.

An alternative calibration procedure which avoids blood loss uses a syringe outfitted with a light excitation—fluorescence detection assembly. The syringe assembly was calibrated once before the cardiac output measurements by measuring ICG fluorescence in the syringe for different concentrations of ICG dye in blood contained in the barrel of the syringe. During the measurement of cardiac output, a blood sample was pulled in the syringe during the slow decay phase of the fluorescence trace, that is the phase during which re-circulating dye is homogeneously mixed in the whole blood volume and is being slowly metabolized. The fluorescence of that sample was converted to concentration using the syringe calibration curve and then related to the transcutaneous fluorescence reading. So long as the ICG concentrations in blood remain sufficiently low (<0.001 mg/ml), a linear relationship can be used to relate fluorescence intensity to concentration.

Either one of these calibration methods can be developed on a reference group of subjects to produce a calibration monogram that would serve for all other subjects with similar physical characteristics (i.e., adults, small children etc.). This is advantageous over prior methods at least in that an additional independent measurement of the blood hemoglobin concentration for computation of the light absorption due to hemoglobin is not required.

EXAMPLE 2

A. A Sample Method and System for Measuring Cardiac Output and Blood Volume

Figure 4:
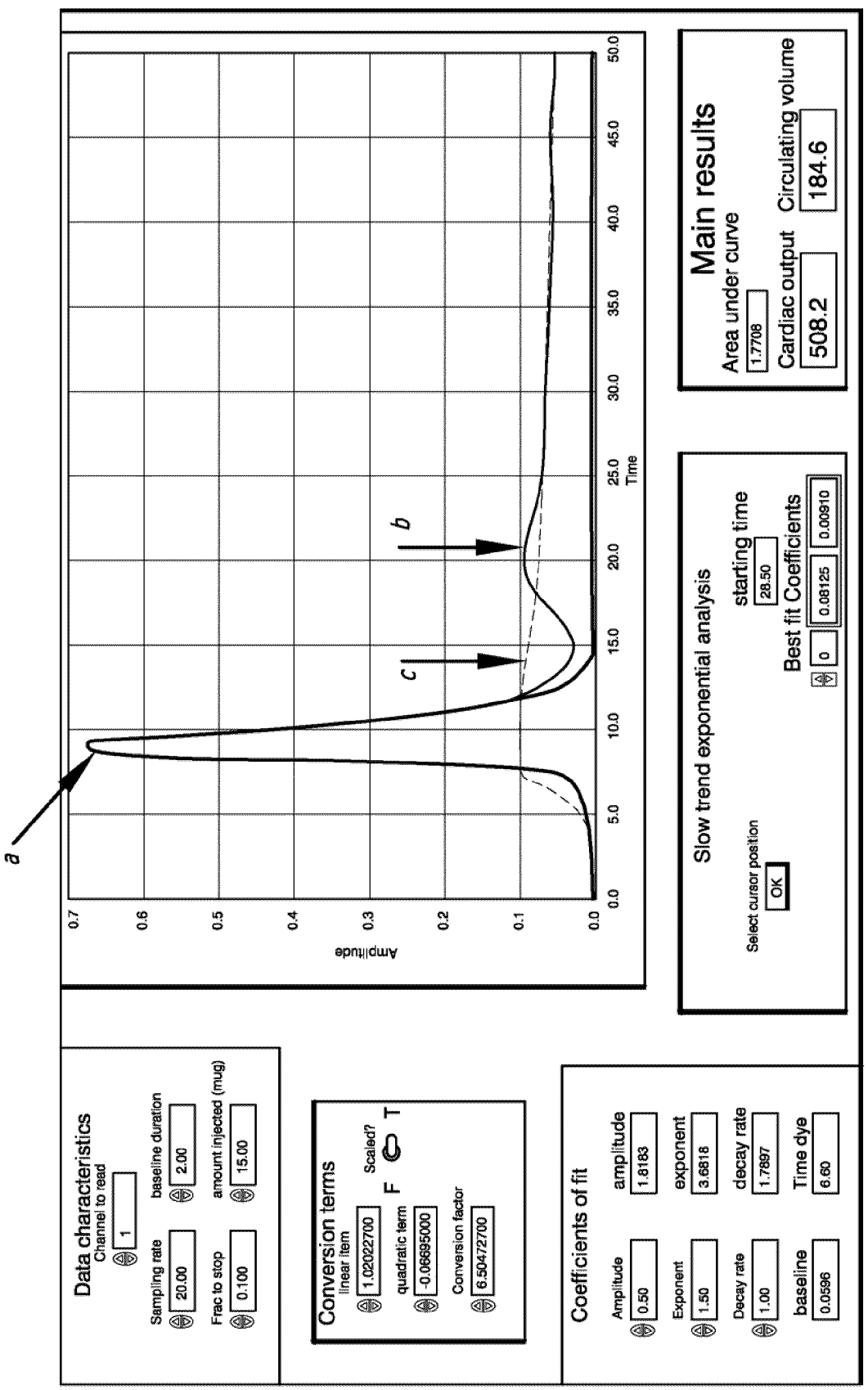
FIG. 4 is a diagrammatic depiction of a user interface of a cardiac output computer program. The interface may depict information regarding values measured and converted from fluorescence to concentration, and parameters of the curve fit for the values obtained using the method or system.

Experiments have been performed in New Zealand White rabbits (2.8-3.5 Kg) anesthetized with halothane and artificially ventilated with an oxygen-enriched gas mixture ($Fi_{O2}$~0.4) to achieve a $Sa_{O2}$ above 99% and an end-tidal $C_{O2}$ between 28 and 32 mm Hg (FIG. 4). The left femoral artery was cannulated for measurement of the arterial blood pressure throughout the procedure. A small catheter was positioned in the left brachial vein to inject the indicator, ICG. Body temperature was maintained with a heat lamp.

Excitation of the ICG fluorescence was achieved with a 780 nm laser (LD head: Microlaser systems SRT-F780S-12) whose output was sinusoidally modulated at 2.8 KHz by modulation of the diode current at the level of the laser diode driver diode (LD Driver: Microlaser Systems CP 200) and operably connected to a thermoelectric controller (Microlaser Systems: CT15W). (MicroLaser Systems, 12841 Western Avenue, Suite H, Garden Grove, Calif. 92841; Phone: +1 714 898-6001; Fax +1 714 897-0979.) The near-infrared light output was forwarded to the animal preparation with a fiber optic bundle terminated by a waterproof excitation-detection probe. The fluorescence emitted by the dye in the subcutaneous vasculature was detected by the probe and directed to a 830 nm interferential filter (Optosigma 079-2230) (OptoSigma, 2001 Deere Avenue, Santa Ana, Calif. 92705; Phone: +1 949 851-5881; Fax: +1 949 851-5058) which passed the fluorescence emission at 830±10 nm and rejected the retro-reflected excitation light at 780 nm. The fluorescence intensity was measured with a photomultiplier tube (PMT; such as Hamamatsu H7732-10MOD) (Hamamatsu Corporation, 360 Foothill Road, Bridgewater, N.J. 08807; Phone: +1 908 231-0960; Fax: +1 908 231-1218) connected to a lock-in amplifier (Stanford Research SR 510) (Stanford Research Systems, Inc., 1290-D Reamwood Avenue, Sunnyvale, Calif. 94089; Phone: +1 408 744-9040; Fax: +1 408 744-9049) for phase-sensitive detection of the fluorescence emission at the reference frequency of the modulated excitation light. The output of the lock-in amplifier was displayed on a digital storage oscilloscope and transferred to a computer for storage and analysis.

In most experiments, one excitation-detection probe was positioned on the surface of the ear arterialized by local heating. In some studies, the laser emission beam was separated in two beams with a beam splitter and directed to two measurement sites (ear skin and exposed right femoral artery). Two detection systems (PMT+lock in amplifier) were used for measurement of the fluorescence dilution traces from the two sites. In all experiments, a complete record of all experimental measurements (one or two fluorescence traces, arterial blood pressure, end-tidal Co2, Doppler flow velocity) was displayed on line and stored for reference.

Calculations. A Lab View program was used to control the oscilloscope used for sampling the fluorescence dilution curves, transfer the data from the oscilloscope to a personal computer and analyze the curves online for estimation of the cardiac output and circulating blood volume. As shown on the program user interface (FIG. 5), the measured fluorescence dilution trace (a) is converted to ICG blood (b) using the calibration parameters estimated as described in the next section of this application and fitted to a model: $C(t)=C_0 t^\alpha \exp(-\beta t)$.

The model fit is performed from the time point for which the fluorescent ICG is first detected to a point on the decaying portion of the trace that precedes the appearance of re-circulating indicator (identified from the characteristic hump after the initial peak in the experimental trace). The model equation is used to estimate the "area under the curve" for the indicator dilution trace. The theory of indicator dilution technique predicts that the area under the concentration curve is inversely proportional to the cardiac output $$(Q) = m \bigg/ \int_0^\infty C(t)\,dt$$

Where m is the mass amount of injected indicator and c(t) is the concentration of indicator in the arterial blood at time t. The program also fits the slow decaying phase of the measurement to a single exponential to derive the circulating blood volume from the value of the exponential fit at the time of injection. For the experimental ICG trace shown in FIG. 4, the estimated cardiac output is 509 ml/min and the circulating blood volume is 184 ml, in the expected range for a 3 Kg rabbit. This computer program is advantageous in that it improved the ability to verify that the experimental measurements are proceeding as planned or to correct without delay any measurement error or experimental malfunction.

Indicator dosage. In this experiment, it was found that a dose of about 0.045 mg injected ICG was optimal in this animal to allow for detection of an intense fluorescence dilution curve and at the same time rapid metabolic disposal of the ICG. Further, with this small dose cardiac function measurements could be performed at about intervals of 4 minutes or less.

Detector placement. Defined fluorescence readings were obtained by positioning the detection probe above the skin surface proximate to an artery or above tissue, such as the ear or the paw arterialized by local heating.

B. Calibration of Transcutaneous Indicator Intensity and Circulating Indicator Concentration Calibration of the transcutaneous fluorescence intensity measured at the level of the animals' ear as a function of ICG concentration in blood was performed as follows. A high dose of ICG (1 mg) was injected intravenously and equilibrated homogeneously with the animal's total blood volume in an about one minute period. At equilibrium, the blood ICG concentration resulting from this high dose is several times larger than the peak ICG concentration observed during the low dose ICG injections (0.045 mg) used to measure cardiac output. In this way, a calibration curve was created that accommodated the full range of ICG concentrations observed during the cardiac function measurements.

As the liver metabolizes ICG, the blood ICG concentration decreases back to 0 in about 20 minutes. During that time period, 5 to 8 blood samples (1.5 ml) were withdrawn from the femoral artery and placed in a pre-calibrated blood cuvette. The fluorescence intensity of the blood in the cuvette was converted to a measurement of concentration using the known standard curve of fluorescence intensity versus ICG concentration established for the cuvette. ICG fluorescence was measured at the level of the ear at the exact time of the blood sample withdrawal. Because ICG is homogeneously equilibrated in the animal's blood volume, when the blood samples are withdrawn, the fluorescence intensity measured at the level of the ear corresponds directly to the ICG blood concentration at the time of the measurement and therefore the ICG concentration determined from the cuvette reading. As this example shows, transcutaneous ICG fluorescence is proportional to blood ICG concentration such that a single blood withdrawal can suffice to find the proportionality factor between the two quantities.

Figure 5:
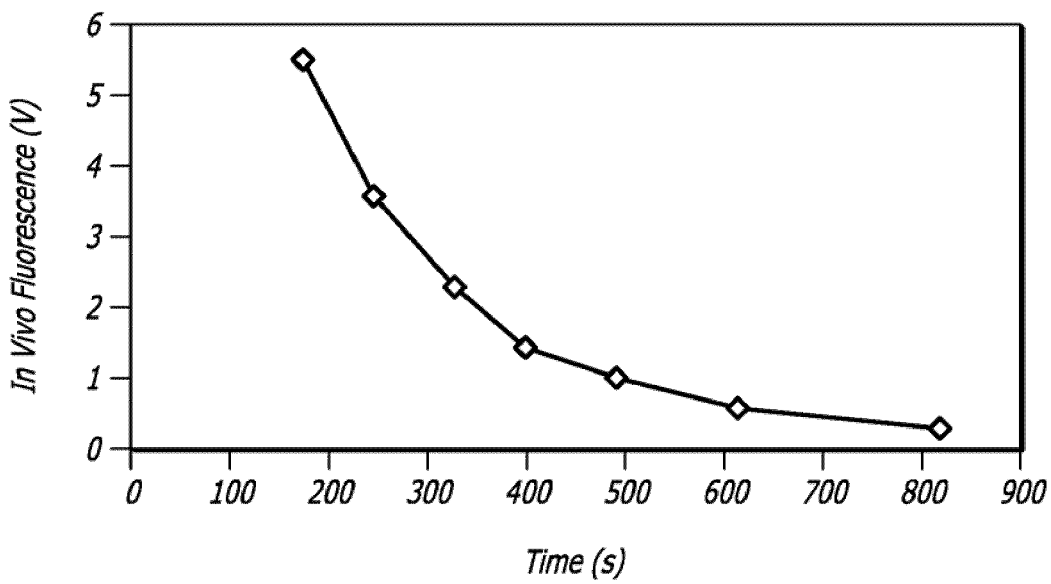
FIG. 5 is a depiction of a decay of fluorescence intensity curve as a function of time following injection of a 1 mg dose of indocyanine green (ICG) in an experimental animal.
Figure 6:
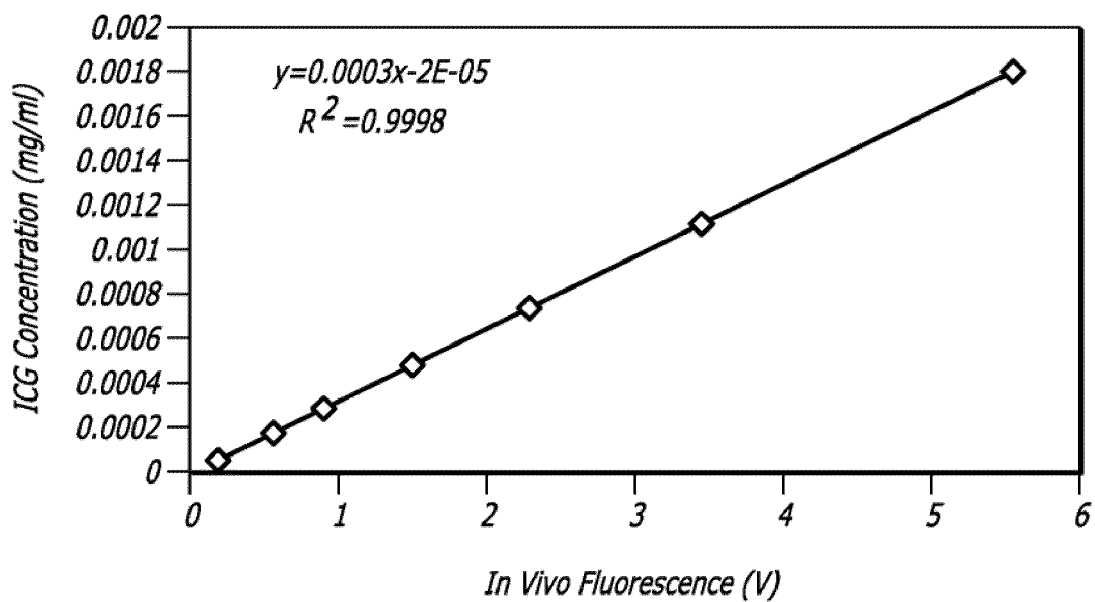
FIG. 6 is a depiction of a calibration curve for blood ICG concentration as a function of transcutaneous ICG fluorescence.

As shown in FIG. 5, the transcutaneous ear fluorescence intensity (in V) as a function of time (in s) after the high dose (1 mg) ICG injection during the calibration sequence. FIG. 5 shows the characteristic first order exponential decay of ICG in blood as the dye is being metabolized. FIG. 6 shows the ICG concentration (in mg/ml) as a function of the in vivo fluorescence for the same example and the same time points. For the range of concentrations used in these studies, ICG concentration and transcutaneous fluorescence were linearly related. The calibration line passes through the origin of the axes since there is no measured fluorescence when the ICG blood concentration is 0.

Thus, a simple proportionality factor exists between blood ICG concentration and transcutaneous fluorescence. This feature of the fluorescence dilution technique measuring light emission is advantageous over the conventional dye dilution technique based on ICG absorption which requires light absorption caused by ICG to be separated from light absorption by tissue and blood. After the proportionality factor is determined, ICG fluorescence dilution profiles can only then be converted into concentration measurements for computation of the cardiac output using the indicator-dilution equation.

Results of cardiac output measurements. Calibrated cardiac output readings have been obtained in 5 animals (body wt: 3.0±0.2 Kg). The following table lists the values during baseline conditions. The values are presented as the mean ± standard deviation of three consecutive measurements obtained within a 15 min period.

TABLE 4

| Exp. | Cardiac output (ml/min) |
|---|---|
| 1 | 530 ± 15 |
| 2 | 500 ± 17 |
| 3 | 370 ± 12 |
| 4 | 434 ± 16 |
| 5 | 481 ± 6 |

The average for the five experiments (463 ml/min) is in order of reported cardiac outputs (260±675 ml/min) measured with ultrasound or thermodilution techniques in anesthetized rabbits (Preckel et al. Effect of dantrolene in an in vivo and in vitro model of myocardial reperfusion injury. Acta Anaesthesiol Scand, 44, 194-201, 2000. Fok et al. Oxygen consumption by lungs with acute and chronic injury in a rabbit model. Intensive Care Med, 27, 1532-1538, 2001). Basal cardiac output varies greatly with experimental conditions such as type of anesthetic, duration and depth of anesthesia, leading to the wide range of values found in the literature. In this example, the variability (standard deviation/mean) of the calculated cardiac output with fluorescence dilution is ~3% for any triplicate set of measurements which compares favorably with the reported variability for the thermodilution technique (~5-10%).

C. Comparison of Measurements Obtained by Fluorescence Dilution Cardiac Output Method Via Transcutaneous Measurement and Subcutaneous Measurement Experimental methodology. The experimental preparation described in the preceding section (Example 2) includes two measurement sites for the fluorescence dilution traces: a transcutaneous site at the level of the ear central bundle of blood vessels and the exposed femoral artery. The ear vasculature is arterialized by local heating. With this preparation, the cardiac output estimates obtained from the peripheral non-invasive (transcutaneous) measurement site were compared with estimates obtained by interrogating a major artery.

The intensity of the fluorescence signal at the level of the exposed femoral artery during the slow metabolic disappearance phase of the injected ICG is compared to the calibrated ear fluorescence measurement to derive a calibration coefficient (arterial ICG fluorescence into ICG blood concentration). In this way cardiac output estimates expressed in ml/min were derived from the two sites.

Figure 8:
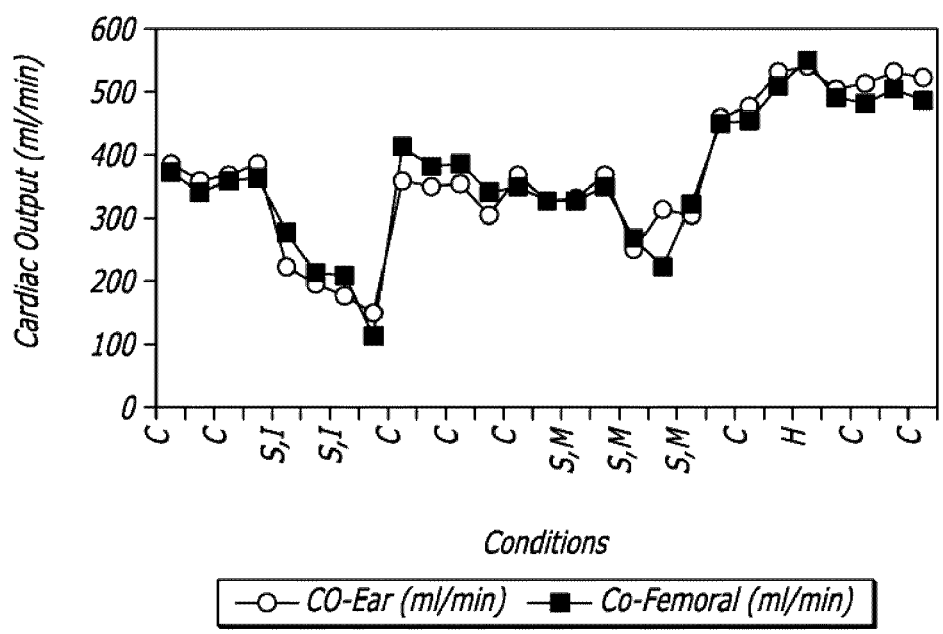
FIG. 8 is a depiction of cardiac output measurements derived from sites on the ear surface and on the exposed femoral artery during one experiment.

Results. FIG. 8 shows the time course of the cardiac output measurements obtained from the ear site and from the exposed femoral artery in a representative experiment during control conditions (C), intense then mild vagal stimulation (S,I and S,M), and post-stimulation hyperemia (H). Near-identical estimates of the cardiac output are obtained from the two sites during all phases of the study.

The relationship between cardiac output derived from measurement of the fluorescence dilution curve at the level of the skin surface ($CO_{skin}$, in ml/min) and at the level of the exposed femoral artery ($CO_{fem}$, in ml/min) was investigated. The linear relationships between the two measures are summarized in the table below:

TABLE 5

| Exp. | Linear regression | Regression Coefficient | Number of measurements |
|---|---|---|---|
| 1 | $CO_{skin} = 0.65 (\pm 0.11) * CO_{fem} + 145.0 (\pm 54.0)$ | 0.81 | 22 |
| 2 | $CO_{skin} = 1.01 (\pm 0.06) * CO_{fem} + 2.0 (\pm 22.0)$ | 0.96 | 27 |
| 3 | $CO_{skin} = 1.05 (\pm 0.14) * CO_{fem} - 56.0 (\pm 54.0)$ | 0.91 | 13 |

The two measures of fluorescence cardiac output are tightly correlated. In the last two experiments, the slope of the regression line is not statistically different from 1.0 and the ordinate is not different from 0.0 indicating that the two measurements are identical. These observations suggest that fluorescence dilution cardiac output can be reliably measured transcutaneously and from a peripheral site of measurement that has been arterialized by local application of heat. Attenuation of the excitation light and ICG fluorescence emission by the skin does not prevent the measurement of well-defined dye dilution traces that can be analyzed to derive the cardiac output.

D. Comparison of Measurements Obtained by Fluorescence Dilution Cardiac Output Method and Doppler Flow Velocity Technique Experimental methodology. The present method was compared with an ultrasonic Doppler velocity probe method to record cardiac output measurements. In this example the above procedure was modified in that, the animal's chest was opened with a median incision of the sternum and a 6 mm 20 MHz Doppler velocity probe was gently passed around the ascending aorta and tightened into a loop that fits snuggly around the aorta.

For detection of the fluorescent detection of the indicator, two illumination +detection fiber optic probes were used: one probe was placed on or above the ear middle vessel bundle and the other probe was placed in proximity to the dissected left femoral artery. Local heating to 42 degrees centigrade arterialized the ear vasculature.

Figure 7:
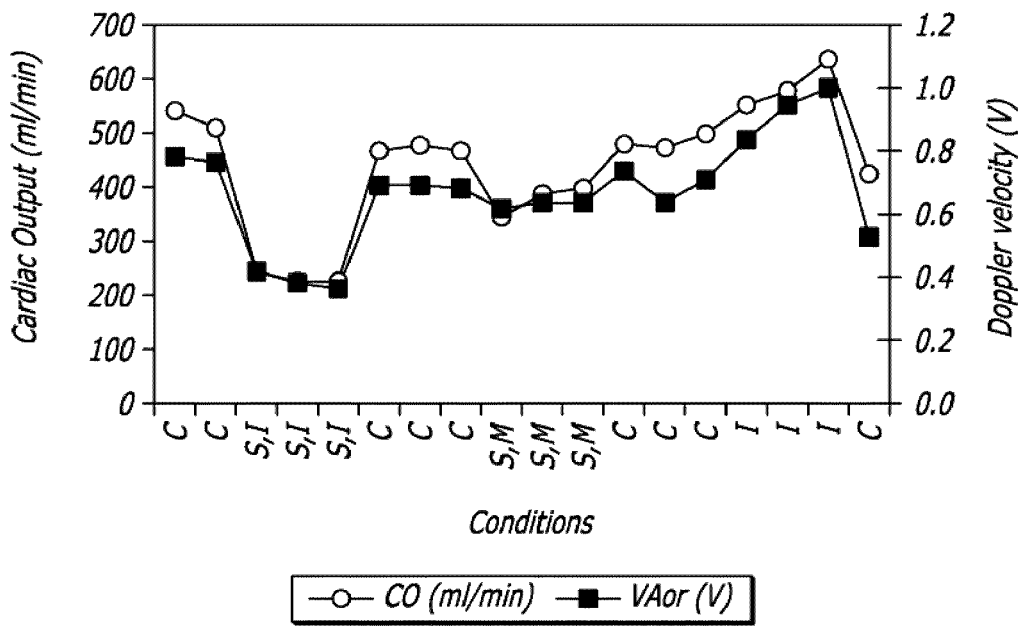
FIG. 7 is a depiction of cardiac output and aortic velocity measurements during one representative experiment.

In this example, two maneuvers were used to change the cardiac output from its control level: vagal stimulation, which reduces the cardiac output, and saline infusion, which increases the circulating volume and cardiac output. The right vagal nerve was dissected to position a stimulating electrode. Stimulation of the distal vagus results in a more or less intense decrease of the heart rate that depends on the stimulation frequency and voltage (1 ms pulses, 3 to 6 V, 10 to 30 Hz). The cardiac output and aortic flow velocity also decrease during vagal stimulation even though less markedly than the heart rate decreases because the stroke volume increases. Saline infusion at a rate of 15-20 ml/min markedly increases the cardiac output. FIG. 7 shows the time course of the cardiac output and aortic velocity measurements in one experiment including control conditions (C), intense then mild vagal stimulation (S,I and S,M), and saline infusion (I).

Results. There is consistent tracking of the Doppler aortic velocity by the fluorescence dilution cardiac output measurement. The relationship between fluorescence dilution cardiac output and aortic Doppler flow velocity was investigated in four rabbits. The linear relationships between fluorescence dilution cardiac output (CO, in ml/min) and aortic flow velocity signal ($V_{aor}$, not calibrated, in Volts) are summarized in the table:

TABLE 6

| Exp. | Linear regression | Regression Coefficient | Measurements |
|---|---|---|---|
| 1 | CO = 789(±123) * $V_{aor}$ + 166(±34) | 0.79 | 27 |
| 2 | CO = 607(±62) * $V_{aor}$ + 50(±32) | 0.90 | 24 |
| 3 | CO = 614(±64) * $V_{aor}$ − 45(±38) | 0.90 | 27 |
| 4 | CO = 654(±41) * $V_{aor}$ − 3(±29) | 0.97 | 18 |

This data indicates that the fluorescence dilution cardiac output is highly correlated with aortic flow velocity as indicated by the elevated regression coefficient ($\geq 0.9$ in 3 experiments). Further, the slopes of the linear regression lines between fluorescence dilution cardiac output and aortic flow velocity are similar and statistically not different in the four studies. This suggests a constant relationship between the two variables across experiments. The ordinates of regression lines are not different from 0 in the last three experimental studies, which suggests absence of bias between the two measures of aortic flow.

The results above establish that fluorescence dilution cardiac output measured transcutaneously tracks the Doppler flow velocity measured in the ascending aorta.

EXAMPLE 3

Comparison with Thermodilution Method

Experimental methodology. Other experiments were performed in New Zealand White rabbits using the methodology described for the preceding example 2. In addition, a 4F thermodilution balloon catheter was inserted into the right femoral vein and advanced until the thermistor reached the main pulmonary artery. Correct placement of the catheter tip was verified visually through the thoracotomy. The catheter was connected to a cardiac output computer to measure the thermodilution cardiac output. Cardiac output measurements were obtained with the present method ($CO_{ICG}$) and the comparison thermodilution method ($CO_{TD}$) during baseline conditions, reduced flow conditions resulting from vagal stimulation, and increased flow conditions resulting from blood volume expansion with saline.

Results. Average values of $CO_{ICG}$ and $CO_{TD}$ measured in baseline conditions in the 10 animals were 412 (±13) ml/min and 366 (±11) ml/min, respectively, in the expected range for anesthetized rabbits. In each animal, $CO_{ICG}$ was linearly related to $CO_{TD}$ as shown on the following table 7. The slope of the regression line (range: 0.74-1.25) was not different from 1.0 in 8 studies. In the combined data from all 10 studies the linear relationship between $CO_{ICG}$ and $CO_{TD}$ had a slope (0.95±0.03) not different from 1.0 and an ordinate (77±10 ml/min) that was slightly >0.

TABLE 7

| Experiment | EQUATION | N | R |
|---|---|---|---|
| 1 | $CO_{ICG}$ = 0.94†(±0.08) $CO_{TD}$ + 84(±23) | 21 | 0.94 |
| 2 | $CO_{ICG}$ = 1.25†(±0.17) $CO_{TD}$ − 0*(±39) | 17 | 0.88 |
| 3 | $CO_{ICG}$ = 0.74(±0.11) $CO_{TD}$ + 122(±26) | 20 | 0.85 |
| 4 | $CO_{ICG}$ = 0.90†(±0.05) $CO_{TD}$ + 98(±15) | 11 | 0.99 |
| 5 | $CO_{ICG}$ = 1.08†(±0.11) $CO_{TD}$ + 84(±47) | 14 | 0.94 |
| 6 | $CO_{ICG}$ = 1.07†(±0.09) $CO_{TD}$ + 16*(±33) | 14 | 0.96 |
| 7 | $CO_{ICG}$ = 1.15†(±0.06) $CO_{TD}$ + 29*(±25) | 12 | 0.99 |
| 8 | $CO_{ICG}$ = 0.82†(±0.09) $CO_{TD}$ + 83(±37) | 12 | 0.94 |
| 9 | $CO_{ICG}$ = 0.88†(±0.12) $CO_{TD}$ + 98*(±62) | 16 | 0.89 |
| 10 | $CO_{ICG}$ = 1.05†(±0.08) $CO_{TD}$ − 20*(±33) | 15 | 0.97 |
| All | $CO_{ICG}$ = 0.95†(±0.03) $CO_{TD}$ + 74(±10) | 152 | 0.94 |

These studies further established that cardiac output $CO_{ICG}$ measured with the present method is linearly related to thermodilution cardiac output $CO_{TD}$. The slope of the regression line between these variables was near 1.0 for most experiments, as well as for the grouped data from all experiments.

EXAMPLE 4

A. Noninvasive Calibration

One embodiment of the calibration system includes a method to determine non-invasively transcutaneously the concentration of a fluorescent indicator injected in the bloodstream by measuring the intensity of the fluorescence light emitted by the indicator when illuminated by a light source in or near the skin and the intensity of the light from that source reflected by or transmitted through the illuminated skin site.

In the pulse dye densitometer (Cardiac output and circulating blood volume analysis by pulse dye densitometry. Iijima T. et al. Journal of Clinical Monitoring, 13, 81-89, 1997, incorporated herein in its entirety by reference), light absorption is measured at two wavelengths: 805 nm where ICG absorption is near maximum and 890 nm where ICG absorption is very small. Assuming at first that tissue absorption of light is only due to blood hemoglobin and ICG, the ratio $C_{ICG}/C_{Hb}$ can be expressed as a function of the ratio $\Phi$ of the optical densities measured at 805 nm and 890 nm, $$C_{ICG}/C_{Hb} = \frac{E_{Hb,805} - \Psi E_{Hb,890}}{\Psi E_{ICG,890} - E_{ICG,805}}$$

where E represents the absorption coefficient from Beer's Law. The latter is expressed as $I_x = I_0 e^{-E \cdot C \cdot x}$ with C=concentration, E=absorption coefficient, x=path length in substance. Note that if we assume that $E_{ICG, 890}$=0, the ratio of the concentrations $C_{ICG}/C_{Hb}$ is linearly related to the ratio of the optical densities measured at two wavelengths.

Taking into account scattering and absorption by other material beside ICG and Hb, the developers of the pulse dye densitometer established that the ratio of the optical density changes between before and after ICG administration at 805 nm and 890 nm could be expressed as a function of the ratio $C_{ICG}/C_{Hb}$.

ICG fluorescence is proportional to the absorption of light by ICG at the wavelength of excitation (805 nm in the model above or 784 nm in our studies). Therefore, we hypothesized that the ratio $C_{ICG}/C_{Hb}$ can be derived from the ratio of the change in light signal measured at the wavelength of emission (related to ICG fluorescence) to the light signal measured at the wavelength of excitation (related to ICG and Hb absorption).

We considered a model of light propagation in tissue, which at first assumed that only hemoglobin and ICG were absorbers (See Table 8 below). The absorption coefficients of ICG and Hb were derived from the literature and considered to be independent of wavelength. We then added a dependence of the absorption coefficients on wavelength and tissue absorption in the model to investigate the effect of these factors.

Figure 11D:
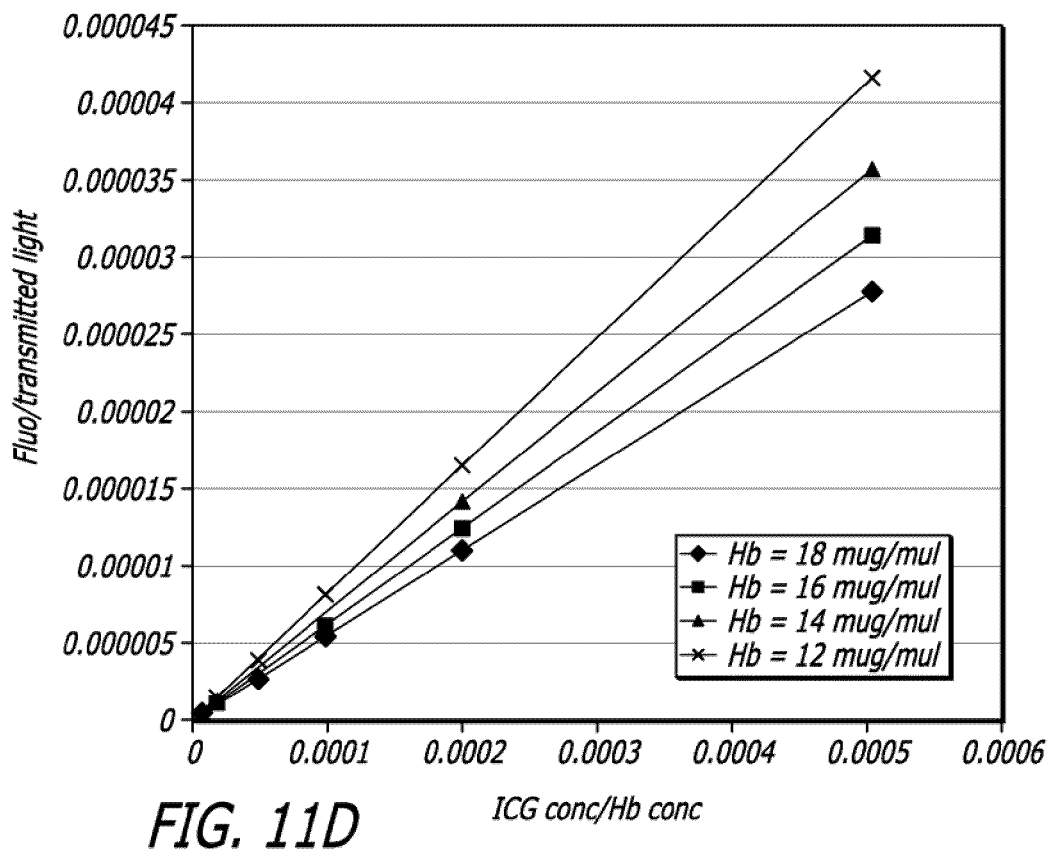

Also, the ratio (emergent fluorescence light/transmitted excitation light) is proportional to the ratio (ICG concentration/Hb concentration) but in this case the slope varies with the hemoglobin content of the tissue (see FIG. 11D). In an alternative embodiment of the calibration system, the concentration of Hb may be obtained from a blood sample, and this concentration value can be used to determine the ratio of ICG value to Hb value, which can then be used with the ratio of transmitted excitation light to fluorescence light to determine the concentration of ICG for calibration.

TABLE 8

1-D Model of Light Propagation and Fluorescence Generation

| | $\Delta x$ | | $\Delta x$ | | $\Delta x$ |
|---|---|---|---|---|---|
| | Excitation absorbed Hb $I_0\mu_{a,Hb}C_{Hb}\Delta x$ | | Excitation absorbed Hb $I_1\mu_{a,Hb}C_{Hb}\Delta x$ | | Excitation absorbed Hb $I_2\mu_{a,Hb}C_{Hb}\Delta x$ |
| Incident $I_0$ | Excitation absorbes ICG $I_0\mu_{a,ICG}C_{ICG}\Delta x$ | Excitation transmitted total $I_1 = I_0 - I_0(\mu_{a,Hb}C_{Hb} + \mu_{a,ICG}C_{ICG})\Delta x$ | Excitation absorbes ICG $I_1\mu_{a,ICG}C_{ICG}\Delta x$ | Excitation transmitted total $I_2 = I_1 - I_1(\mu_{a,Hb}C_{Hb} + \mu_{a,ICG}C_{ICG})\Delta x$ | Excitation absorbes ICG $I_2\mu_{a,ICG}C_{ICG}\Delta x$ |
| | Excitation absorbed total $I_0(\mu_{a,Hb}C_{Hb} + \mu_{a,ICG}C_{ICG})\Delta x$ | | Excitation absorbed total $I_1(\mu_{a,Hb}C_{Hb} + \mu_{a,ICG}C_{ICG})\Delta x$ | | Excitation absorbed total $I_2(\mu_{a,Hb}C_{Hb} + \mu_{a,ICG}C_{ICG})\Delta x$ |
| | Fluorescence produced ICG $Q \cdot I_0\mu_{a,ICG}C_{ICG}\Delta x$ | Fluo. transmitted total $F_1 = Q \cdot I_0\mu_{a,ICB}C_{ICG}\Delta x$ | Fluorescence produced ICG $Q \cdot I_1\mu_{a,ICG}C_{ICG}\Delta x$ | Fluo. transmitted total $F_1 = Q \cdot I_0\mu_{a,ICG}C_{ICG}\Delta x - F_1(\mu_{a,Hb} + \mu_{a,ICG}C_{ICG})\Delta x$ | Fluorescence produced ICG $Q \cdot I_2\mu_{a,ICG}C_{ICG}\Delta x$ |
| $F_0 = 0$ | Fluorescence absorbed Hb 0 | | Fluorescence absorbed Hb $F_1\mu_{a,Hb}C_{Hb}\Delta x$ | | Fluorescence absorbed Hb $F_2\mu_{a,Hb}C_{Hb}\Delta x$ |
| | Fluorescence absorbed ICG 0 | | Fluorescence absorbed ICG $F_1\mu_{a,ICG}C_{ICG}\Delta x$ | | Fluorescence absorbed ICG $F_2\mu_{a,ICG}C_{ICG}\Delta x$ |
| | Fluorescence absorbed total 0 | | Fluorescence absorbed total $F_1(\mu_{a,Hb}C_{Hb} + \mu_{a,ICG}C_{ICG})\Delta x$ | | Fluorescence absorbed total $F_2(\mu_{a,Hb}C_{Hb} + \mu_{a,ICG}C_{ICG})\Delta x$ |

The following data and assumptions were applied to the model of Table 8:

$\mu_{a,ICG}$=38.1 µl·µg$^{-1}$·mm$^{-1}$ for wavelength $\lambda$=784 nm $\mu_{a,HbO2} \sim \mu_{a,Hb}$=0.0026 µl·µg$^{-1}$·mm$^{-1}$ for wavelength $\lambda$=784 nm Initially, we assume that the absorption coefficients have the same values at 830 nm (fluorescence) and at 784 nm (incident excitation light).

$C_{Hb}$=12–18 g·dl$^{-1}$=120–180 µg/µl in blood $C_{ICG}$ max=0.005 µg/µl in blood Tissue assumed to contain 10% blood Quantum yield of ICG fluorescence=0.04

Transmission calculated through 40 mm tissue in 0.02 mm increment

We modeled transmission and fluorescence signals at 784 nm and 830 nm for different ICG concentrations and hemoglobin contents when absorption coefficients are the same, and the results are illustrated in the graphs of FIGS. 11A-11D. For this simple model, the transmitted excitation light decreases nonlinearly as a function of ICG concentration in the model and the curve varies with the hemoglobin content (see FIG. 11A). Also the emergent fluorescence light nonlinearly increases with ICG concentration (inner filter effect) and the curve varies with hemoglobin content (see FIG. 11B). Thus, the fluorescence signal varies markedly if there is more or less absorption by blood in the tissue.

However, the ratio (emergent fluorescence light/transmitted excitation light) is proportional to the ICG concentration and independent of the hemoglobin content of the tissue (see FIG. 11C). Therefore, by measuring the ratio and if the relationship is known, the ICG concentration can be estimated.

We also modeled transmission and fluorescence signals and at 784 nm and 830 nm for different ICG concentrations and hemoglobin contents when absorption coefficients are the different and an additional absorber is included, and the results are illustrated in the graphs of FIGS. 12A-12D.

Absorption by ICG is actually slightly more elevated at 784 nm (excitation) than it is at 830 nm (fluorescence peak). In contrast oxy-hemoglobin absorption is less at 784 nm (excitation) than it is at 830 nm. In addition to blood hemoglobin and ICG, bloodless tissue absorbs to a certain extent. We determined various values from the literature:

$\mu_{a,ICG}$=38.1 µl·µg$^{-1}$·mm$^{-1}$ for wavelength $\lambda$=784 nm $\mu_{a,HbO2} \sim \mu_{a,Hb}$=0.0026 µl·µg$^{-1}$·mm$^{-1}$ for wavelength $\lambda$=784 nm $\mu_{a,ICG}$=34.1 µl·µg$^{-1}$·mm$^{-1}$ for wavelength $\lambda$=830 nm $\mu_{a,HbO2} \sim \mu_{a,Hb}$=0.0035 µl·µg$^{-1}$·mm$^{-1}$ for wavelength $\lambda$=830 nm $\mu_{a,tissue}$=0.1·mm$^{-1}$ independent of wavelength in the range 784-830 nm.

$C_{Hb}$=12-18 g·dl$^{-1}$=120-180 µg/µl in blood $C_{ICG}$ max=0.005 µg/µl in blood Tissue assumed to contain 10% blood Quantum yield of ICG fluorescence=0.04

Transmission calculated through 40 mm tissue in 0.02 mm increment

For this more complete model, the magnitude of the transmitted excitation light and emergent fluorescent lights are markedly decreased when compared to the first model primarily because of the absorption by bloodless tissue. Both signals follow the pattern found for the simple model. In particular, the emergent fluorescence light nonlinearly increases with ICG concentration (inner filter effect) and the curve varies with hemoglobin content.

Figure 12A:
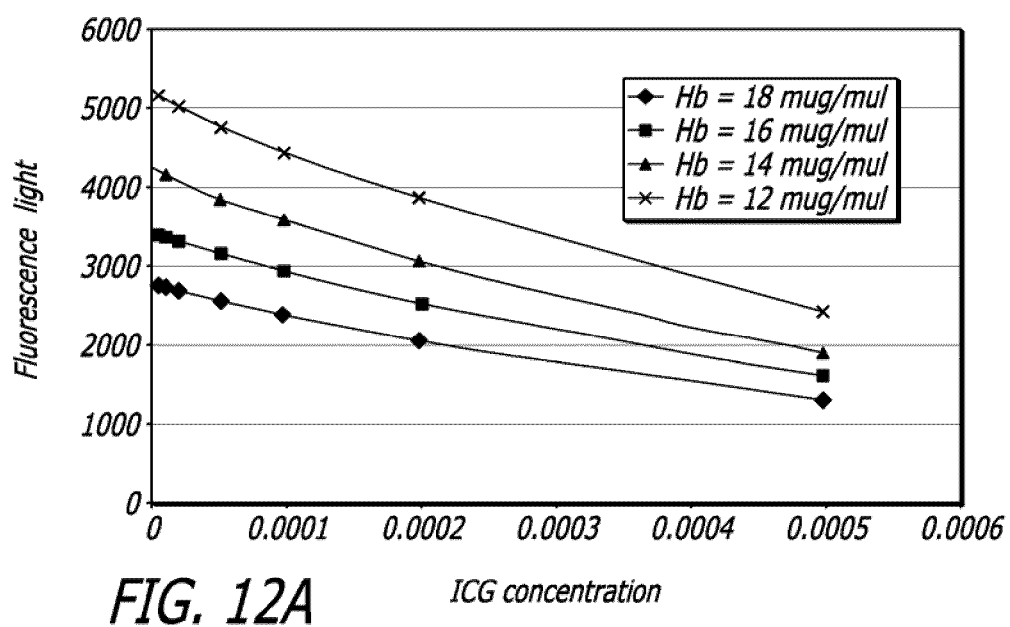
FIGS. 12A-12D are graphs showing transmission and fluorescence signals at 784 nm and 830 nm for different ICG concentrations and hemoglobin contents when absorption coefficients vary with wavelength and an additional absorber is included.
Figure 12B:
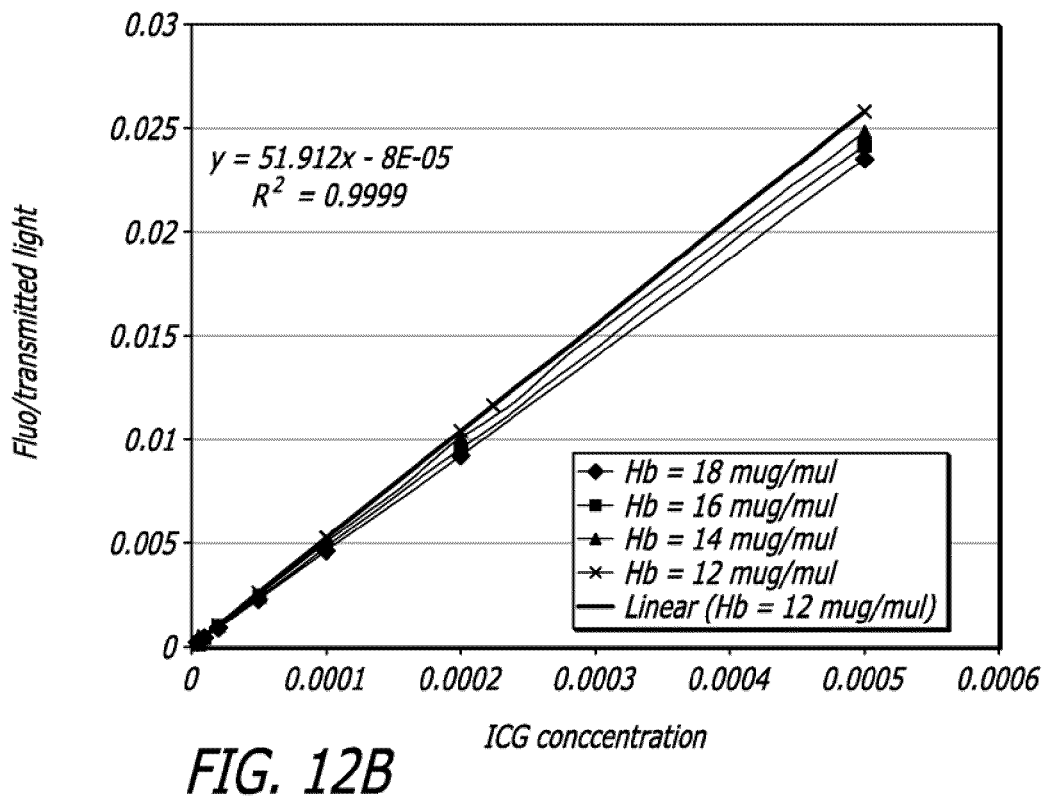
Figure 12C:
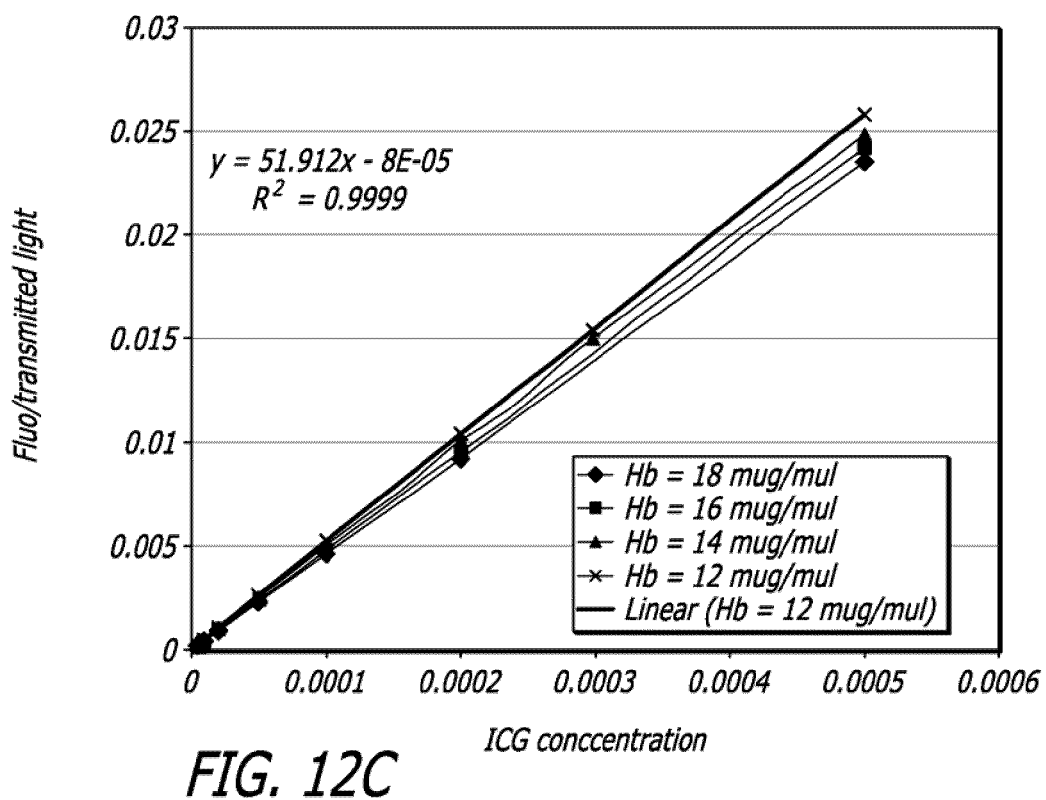
Figure 12D:
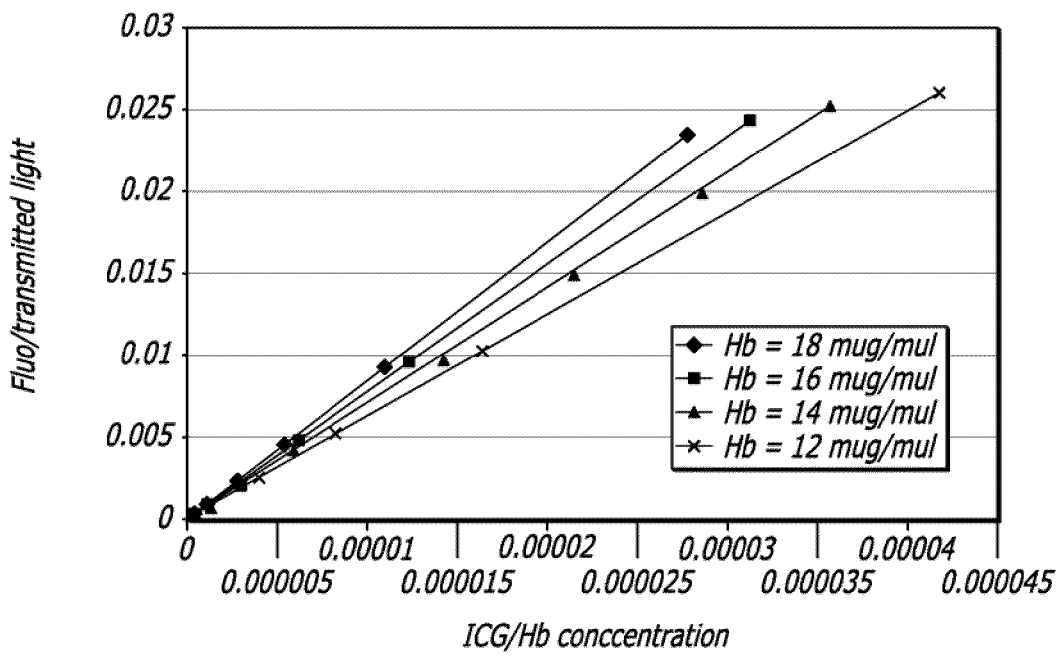

As before the ratio (emergent fluorescence light/transmitted excitation light) is proportional to the ICG concentration (See FIG. 12C). While the slope is dependent on the hemoglobin content, there are only small differences between the four levels of hemoglobin considered. This suggests that by measuring the ratio of the fluorescence/transmitted light, the ICG concentration can be estimated once the linear relationship is determined and possibly including a factor that accounts for the hemoglobin content.

While these models do not consider tissue scattering, the latter is often assumed to increase the path length of light in tissue by a fixed proportionality factor: the path length factor (about 3.6 for human forearm, see Measurement of hemoglobin flow and blood flow by near-infrared spectroscopy. Edwards A. D. et al.—J. Appl. Physiol. 75, 1884-1889, 1993, the entire contents of which are incorporated herein by reference). This suggests that the model analysis above would likely remain valid even in the presence of scattering.

Determination of Hematocrit and Cardiac Output from Optical Transmission and Reflection Changes A. The optical transmission and reflection through blood filled tube vary unequivocally with hematocrit. In the Monte-Carlo simulations in which we studied the variations of the optical signals for different hematocrit levels and different ICG concentrations, we obtained relationships between optical transmission, optical reflection, and hematocrit.

Figure 23A:
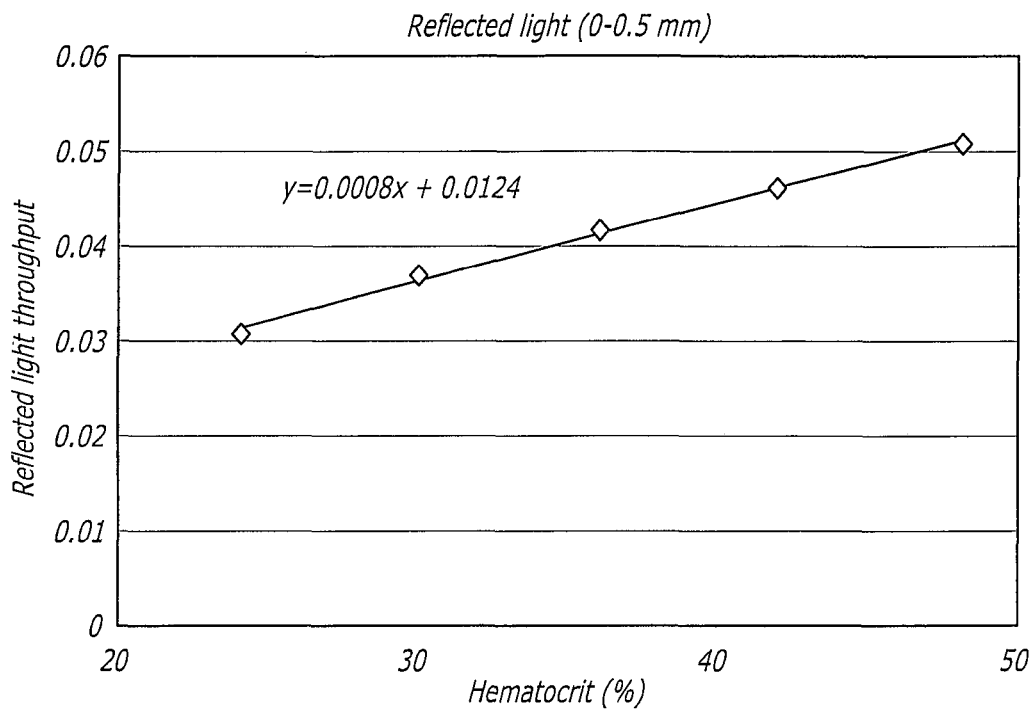
FIGS. 23 A-B illustrate reflected and transmitted light throughput profiles, respectively, relative to changes of hematocrit in blood.
Figure 23B:
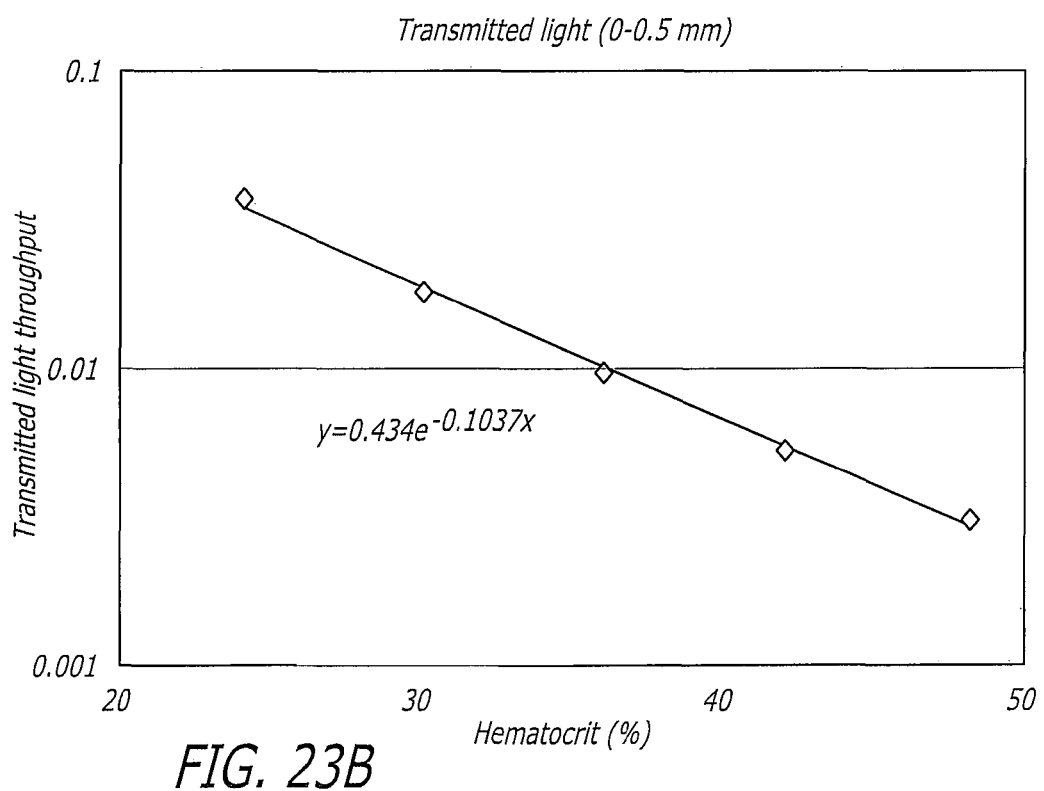

As shown in FIGS. 23 A and B, the reflected light intensity measured near the point of illumination increases linearly with hematocrit (FIG. 23A). The transmitted light intensity measured across the tube facing the point of illumination decreases exponentially with hematocrit (FIG. 23B).

Figure 24:
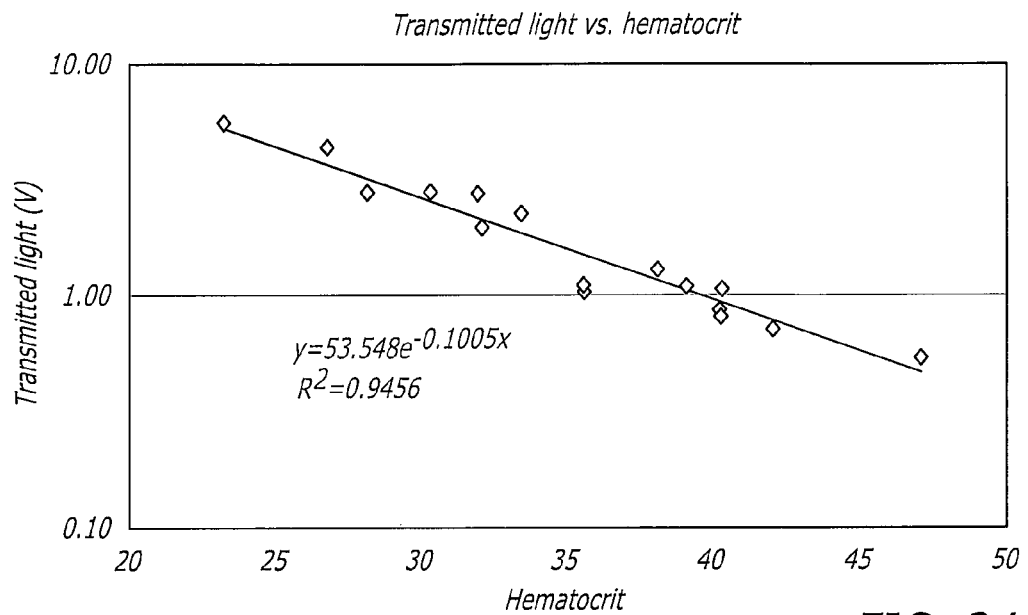
FIG. 24 is a depiction of a plot of transmitted light vs. hematocrits.

Measuring both optical signals simultaneously, we determined the hematocrit or hematocrit change due to a perturbation. Confirmation of the variation of the transmitted light with hematocrit was obtained in the bovine blood tube experiments performed in June/July 2007 (FIG. 24). In these experiments, we had blood mixtures circulated through a blood-filled tube. The hematocrit was manipulated by adding varying amounts of plasma or red blood cells to the blood mixture. The optical signals were monitored with a probe carrying illumination, reflected light, and transmitted light fibers. The back-fluorescence and forward fluorescence were monitored as well.

The dimensions of the collecting optics for the transmitted light signal were the same as that used in the computer simulations. Concurrently, the exponential rate of the transmitted light decay with hematocrit (=slope on log scale) is not different from that predicted in the simulations. The observations combined from several studies confirm the simulation results and indicated an exponential dependence of the transmitted light with hematocrit. Once this relationship was known for a tube geometry and illumination/detection pattern, it can be reversed to determine the hematocrit from the optical transmission. Note that the reflected light results from these studies are not usable because of instrumental changes done from one study to the next.

Figure 25:
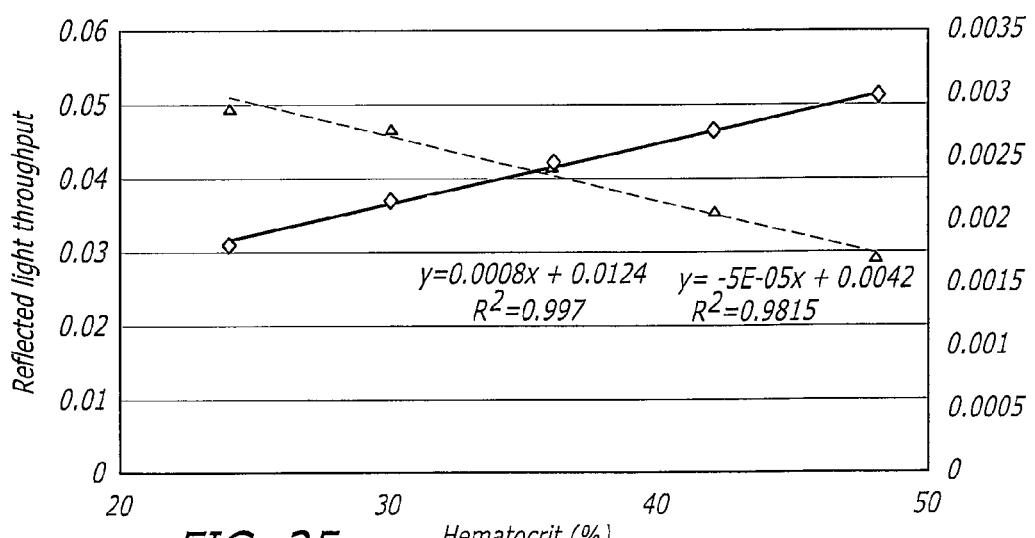
FIG. 25 is a depiction of plot of the reflected light measured away from the point of illumination being less intense than the reflected light measured near the point of illumination.

An alternative to the transmission measurement is to measure the ratio of the reflected light intensity at two distances from the point of illumination. We know from the simulation studies that the reflected light intensity measured away from the point of illumination decreases when the hematocrit increases. On the graph of FIG. 25, the reflected light measured away from the point of illumination (red trace) is about 15 times less intense than the reflected light measured near the point of illumination (blue trace, same data as above) and it decreases when hematocrit increases. The decreasing trend is not perfectly linear.

Figure 26:
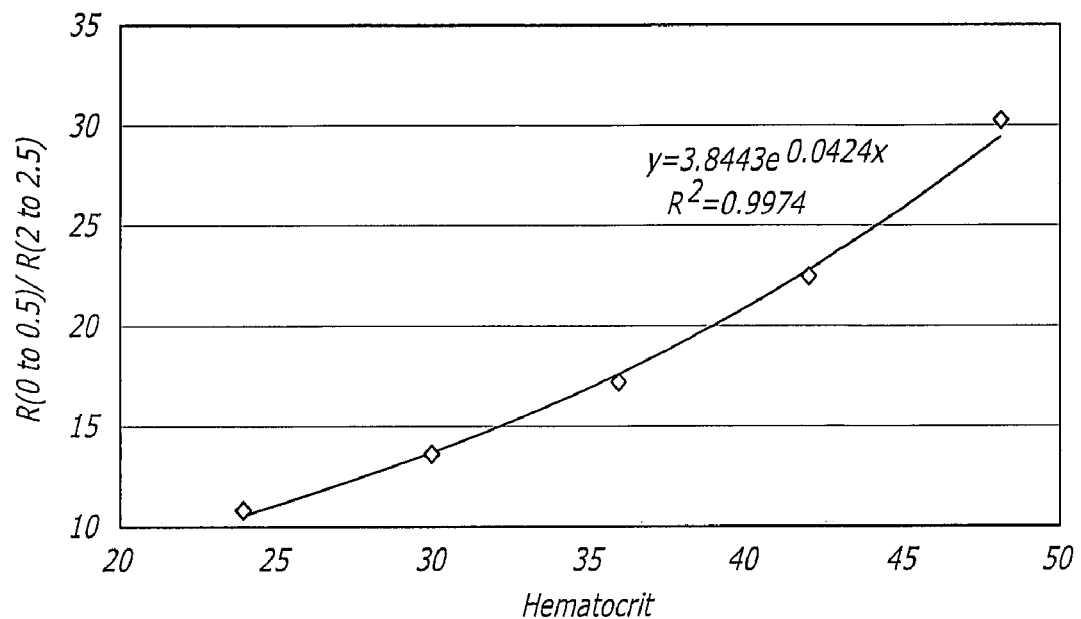
FIG. 26 is depiction of plot of the ratio of two reflected light intensities increases exponentially with hematocrit.

The ratio of the two reflected light intensities shown in FIG. 26 increases nearly exponentially with hematocrit. The advantage of using this ratio is that it is in all likelihood much less sensitive to variations in the coupling of the illumination and detection probes with the blood tube. For instance, we could build a probe with two sets of fibers, the farther fibers being arranged along the long axis of the tube. Also, the dynamics of the signal change is substantially larger for the reflectance ratio when compared to the change of the reflectance alone (~300% vs. 65% for Hct increasing from 24 to 48).

From these observations, we disclose that hematocrit can be determined from optical measurements of reflected light in combination with transmitted light or from reflected light measured from one or multiple locations on a blood carrying medium. The measurement could be performed transcutaneously, transarterially, intraarterially, or across an extracorporeal arterial circulatory path.

B. Cardiac Output is Related to Hematocrit Changes Detected in an Artery.

Going back to the indicator dilution method applied to plasma and red blood cells, and considering that blood is composed primarily of these two substances. The plasma volume that passes through the outflow of the heart during time $\Delta t$ is equal to:

$$V_{plasma} = (1-Hct) \cdot Q \cdot \Delta t$$

We assume that a small amount of plasma is injected in the venous circulation and remains intravascular at least until the location of the sensor at the outflow of the heart. Also the added plasma volume is small enough to keep cardiac output Q unchanged. In such conditions, the change in plasma volume at the location of the sensor is $$\Delta V_{plasma} = -\Delta Hct \cdot Q \cdot \Delta t$$

Replacing the finite interval of time $\Delta t$ with a differential dt and integrating over time yields $$\text{Injected amount} = \int_0^\infty \Delta V_{plasma} dt = -Q \int_0^\infty \Delta Hct \cdot dt$$

Therefore the cardiac output Q can be determined based on the amount of plasma (or saline) injected and the hematocrit change trace integrated over time. The usual approximation for eliminating the recirculation is applied. Also, the hematocrit change can be measured anywhere along the arterial circuitry.

$$Q = -\frac{\text{Injected amount}}{\int_0^\infty \Delta Hct \cdot dt}$$

Where "Injected amount" is the volume of plasma injected and $\Delta Hct$ represents the hematocrit change detected on the arterial side.

By combining these observations we disclose that cardiac output can be determined by monitoring optical transmission or reflection changes detected on a blood carrying medium. The measurement could be performed transcutaneously, transarterially, intraarterially, or across an extracorporeal arterial circulatory path.

Figure 27:
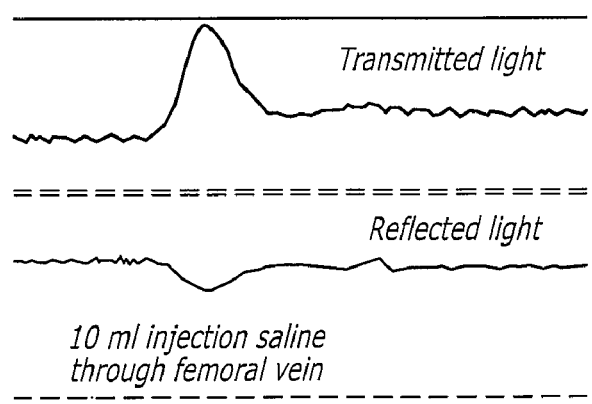
FIG. 27. is a depiction of results of cardiac output device for the dialysis application.

Note that in-vivo (rabbit) test of the cardiac output device for the dialysis application, we observed marked changes of the transmitted (blue) and reflected (pink) light signals detected with the probe (FIG. 27).

While the injected dose (10 ml) was likely too high to keep the cardiac output constant, these observations suggest that the optical readings could be used to determine hematocrit changes and therefore cardiac output from small dose injections of saline or other inert liquid. A necessary condition is that the liquid remains intravascular between the injection site and the detection site. This may be enhanced by the use of agents that osmotically bind the water, such as albumin, other proteins or starches that are used for intraoperative volume replacement such as Hespan.

In addition, the hematocrit changes predicted in the simulations and experimentally observed both in-vitro and in-situ in the animal could be detectable transcutaneously, transarterially, intraarterially, or across an extracorporeal arterial circulatory path.

The disclosed methods for hematocrit and cardiac output determination are similarly performed by the systems of U.S. patent application Ser. No. 11/625,184, filed Jan. 19, 2007; U.S. patent application Ser. No. 11/744,147, filed May 3, 2007; U.S. patent application Ser. No. 11/744,157, filed May 3, 2007; U.S. patent application Ser. No. 11/744,229, filed Jul. 6, 2007, the content of all of these applications is incorporated herein by reference.

Dialysis Probe for Cardiac Output Measurement

Figure 28A:
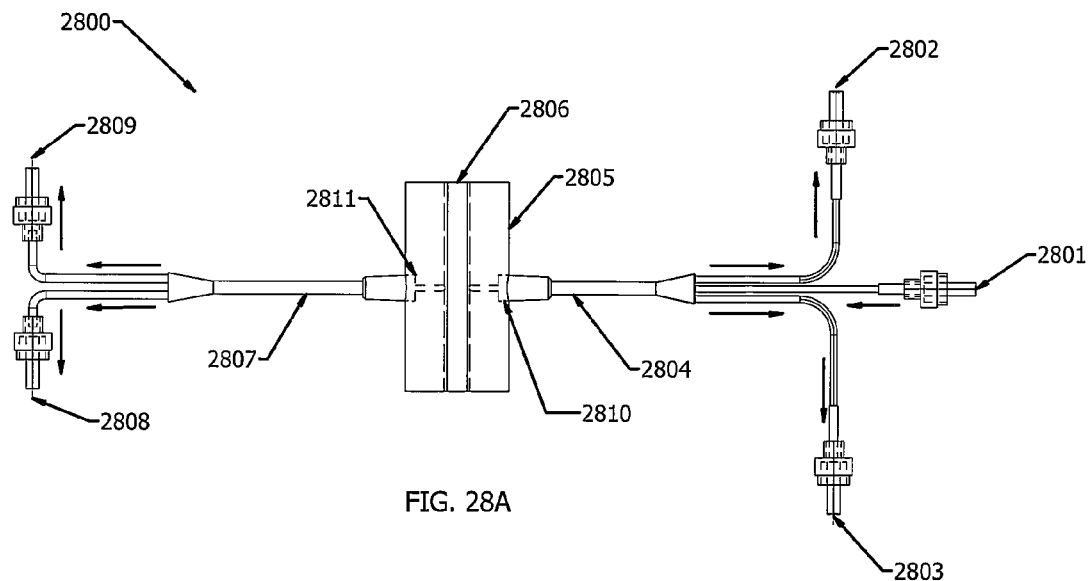
FIGS. 28 A-C depict a probe assembly configuration that may be attached to tubing of a dialysis machine.

FIG. 28A depicts an alternative probe configuration which its operation is substantially similar to that of the dialysis probe depicted in FIGS. 22A-C above. The probe fixture 2805 includes an opening slot 2806 so that the dialysis tubing can snap into the center of the fixture 2805 without additional locking elements. The probe configuration 2800 may receive a laser input through the port 2801 and illuminates the indicator or ICG carrying blood of the patient. There may be two main ports 2810 and 2811 which are positioned on substantially opposite sides of the probe fixture 2805.

The port 2810 includes fibers responsible for laser illumination 2801 and detection of back fluorescence 2802 and reflectance 2803 of the emitted light having a wavelength within 750-1000 nm.

The port 2811 includes fibers to detect forward fluorescence 2809 and transmission light 2808.

Each of the ports 2802, 2803, 2808 and 2809 will be connected to their corresponding photomultipliers (PMT) for detecting their electrical values.

The hemodialysis system will receive the back fluorescence and reflectance through the ports 2802 and 2803, respectively. Additionally, the system is capable of receiving the forward fluorescence and transmission lights through ports 2809 and 2808, respectively. FIG. 28A is a side view of the probe and channel assembly configuration. Each channel has been marked by an arrow identifying the direction of travelling light.

Figure 28B:
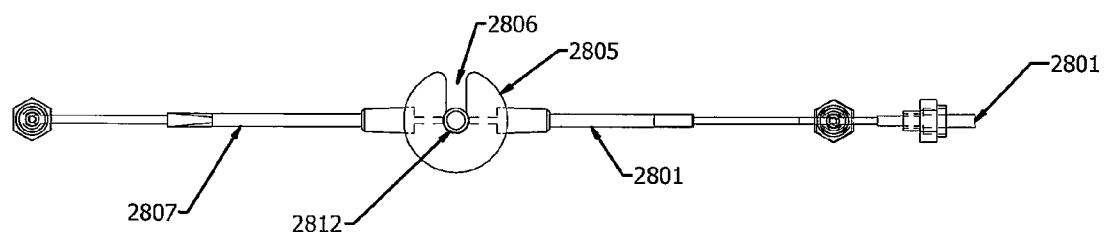
Figure 28C:
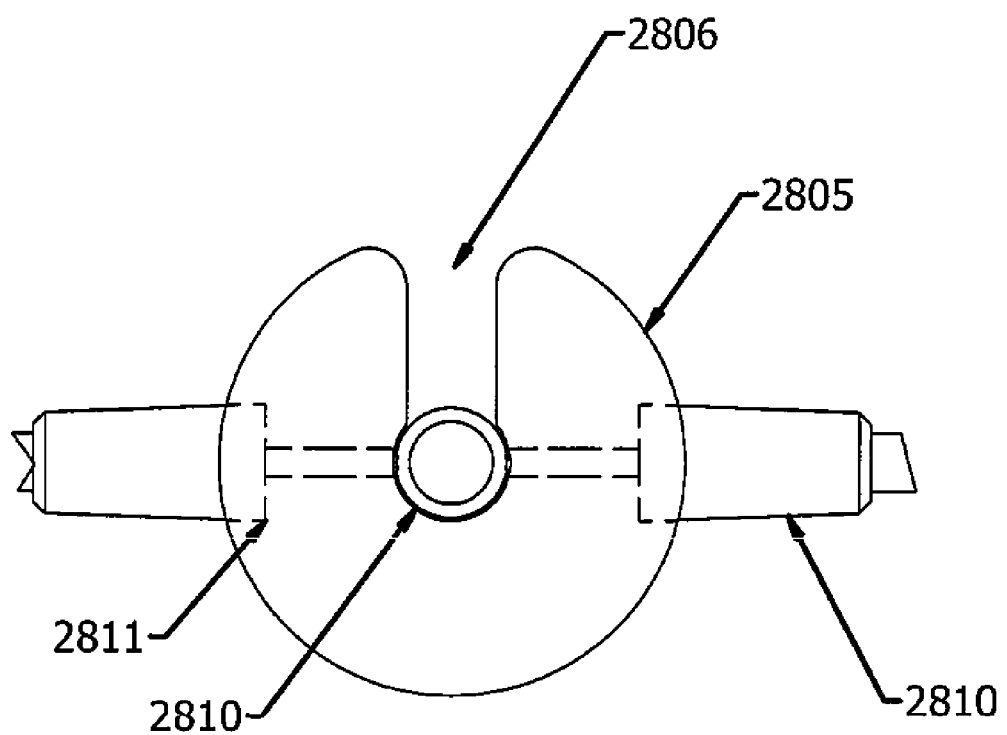

FIG. 28B displays the top view of the assembly having the blood transporting tube 2812 installed in the middle of the probe fixture 2805. The tube 2812 is inserted through opening 2806 to be positioned in the center of the fixture 2805. FIG. 28C displays a magnified top view of the probe fixture 2805.

Figure 29A:
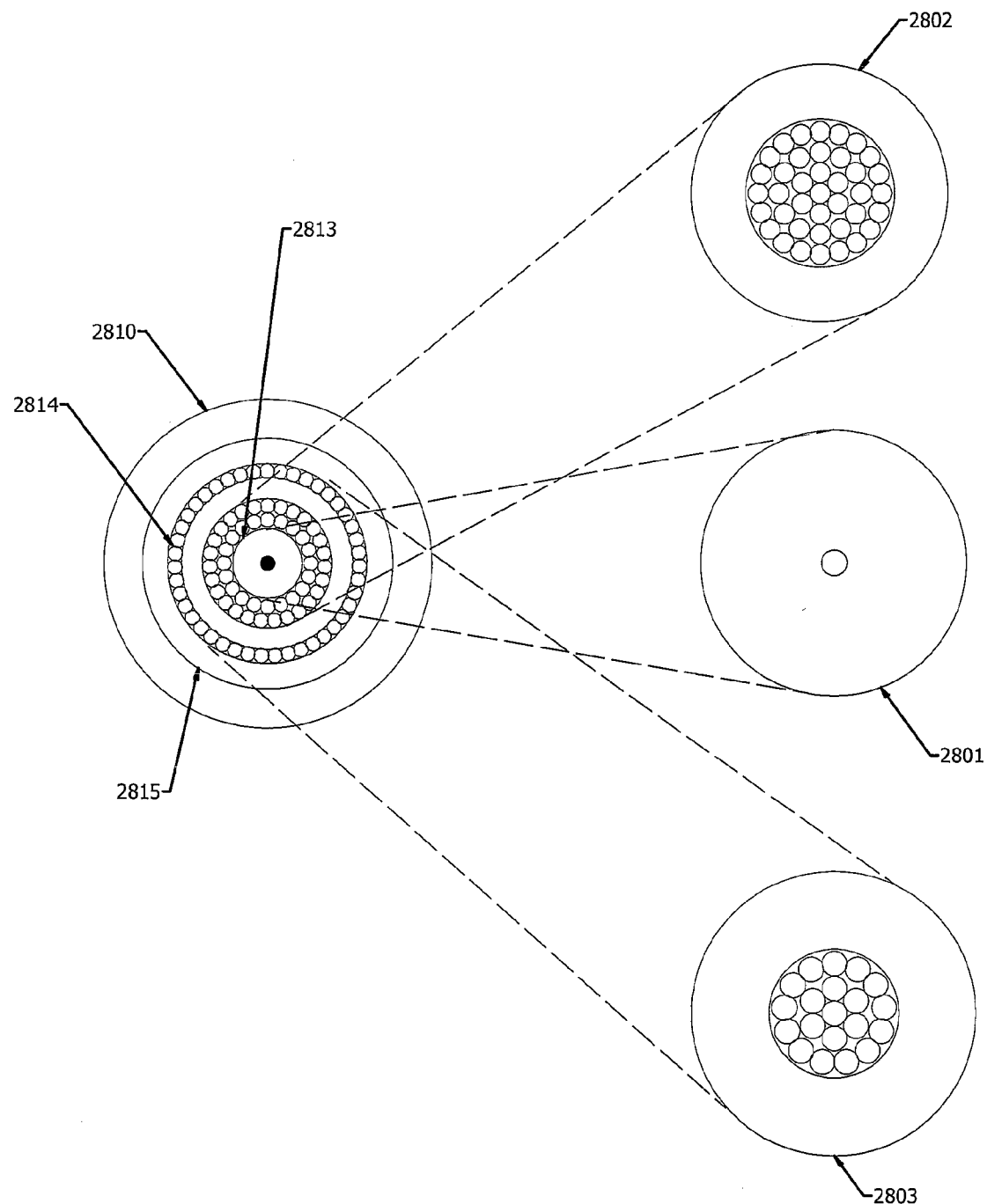
FIGS. 29 A-B depict the fiber configurations of the probe of FIGS. 28 A-C.

FIG. 29A depicts the port 2810 along with its extensions to ports 2801, 2802 and 2803. Each of the ports has been shown in front view displaying their fiber assembly.

The displayed fiber assembly of port 2810 in FIG. 29A includes laser input line 2813, the back fluorescence line 2814 and reflectance line 2815. Each line connects to its corresponding port 2801, 2802, and 2803, respectively. The selected laser line has outer wall thickness of 6.5-7.5 micron which effectively is the space between the laser fiber and the back fluorescence detection fibers. The space between the back fluorescence fibers and the reflectance fibers have been provided by the outer wall of the back fluorescence fiber line having a thickness of approximately 7.5-11 micron. The present invention is not limited to the above thickness and or spacing between the different fiber lines. It would be obvious to an ordinary skilled practitioner to select the proper spacing for a given dialysis application.

Figure 29B:
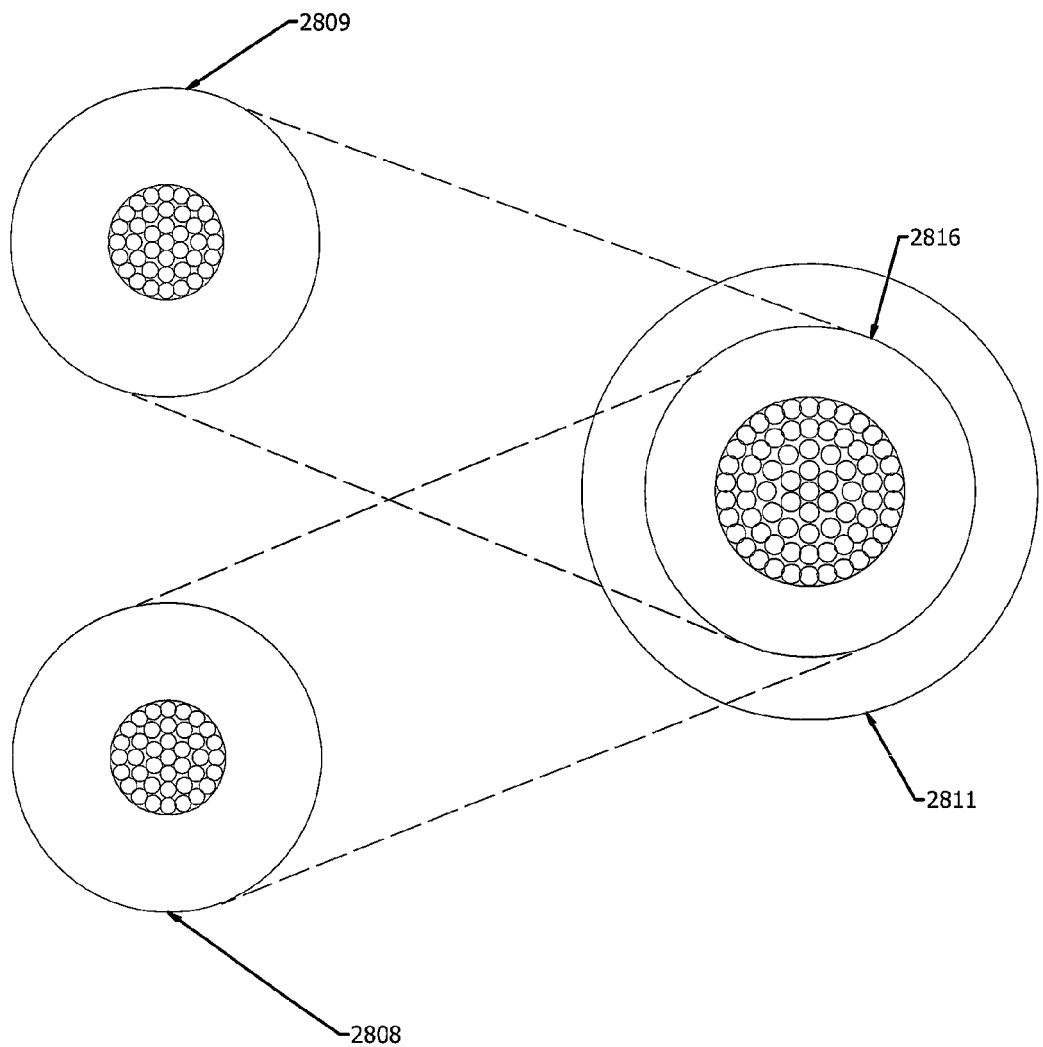

FIG. 29B depicts the corresponding front view of fiber line of port 2811 on the opposite side of the probe. In this case, the forward fluorescence and transmission fibers are randomly distributed together within a single line 2816 within the port 2811. The forward fluorescence and the transmission lights branch out to their respective ports 2809 and 2808, respectively.

The dialysis probe of the present invention in one embodiment can be used for determination of the cardiac output and blood volume of a patient and it is structured to meet the clinical requirements. The probe body (the fixture 2805) is made of aluminum and as discussed above includes fiber optics through which the indicator (i.e. Indicyanine green) that is carried by the blood is detected. The fixture body is made of anodized aluminum and it preferably has a dark color or painted with a dark color i.e. black to avoid any reflection of light within the system. The fixture further has an axially running channel 2806 in which the tubing carrying blood is installed. The channel is designed to fit the tubing in such a way to prevent inadvertent slipping of the tube out of the channel. The probe ports 2810 and 2811 come in intimate contact with the tubing.

The probe includes a main cable that is built into trifurcated cable. The probe further comprises a central fiber for laser input. The outer edge of the central fiber to the edge of the next ring of fibers (back fluorescence fibers) can be approximately 100 microns. The space may be achieved by placing a tube of approximately 100 micron wall thickness between the laser and the back fluorescence fibers.

In order to achieve intimate contact of the probe tip to the silastic tubing that is place in the fixture, the tip of the probe needs to sit just proud of the fixture cavity surface having approximately −0.5 mm-0.7 mm.

The transmission cable comprises of bifurcated cable having approximately 100 micron fiber bundled within an approximately 2 mm diameter. The bifurcation of the cable to two SMA connectors with a 50/50 split of number of fibers. The transmission and forward fluorescence tip will be placed in a ferrule not more than 3 mm in diameter. In order to achieve intimate contact of the probe tip to the silastic tubing that is placed in the fixture, the tip of the probe needs to sit just proud of the fixture cavity surface having approximately −0.5 mm to 0.7 mm protrusion.

The cardiac output and blood volume of the patient are determined using this probe assembly, wherein the determination is similar in process to what has been disclosed in the previous sections of this specification.

The present probe assembly configuration above is not limited to any size or spacing parameters above. The probe of the present invention may be modified to include more channels than what has been disclosed to detect other lights. Ordinary skilled practitioner would modify the present probe with a proper parameters and elements for a given application.

Cardiac Output Monitor Calibrator

The dialysis system may be tested by the calibrator of the present invention prior to for example the hemodialysis process. The accuracy of the cardiac output monitor system in hemodialysis application may be relied upon the accuracy and stability of the system gains and laser injection level. In order to insure that the system is initialized with the correct signal levels, the system hardware i.e. PMTs and other reading devices may be calibrated prior to the hemodialysis application.

Figure 30:
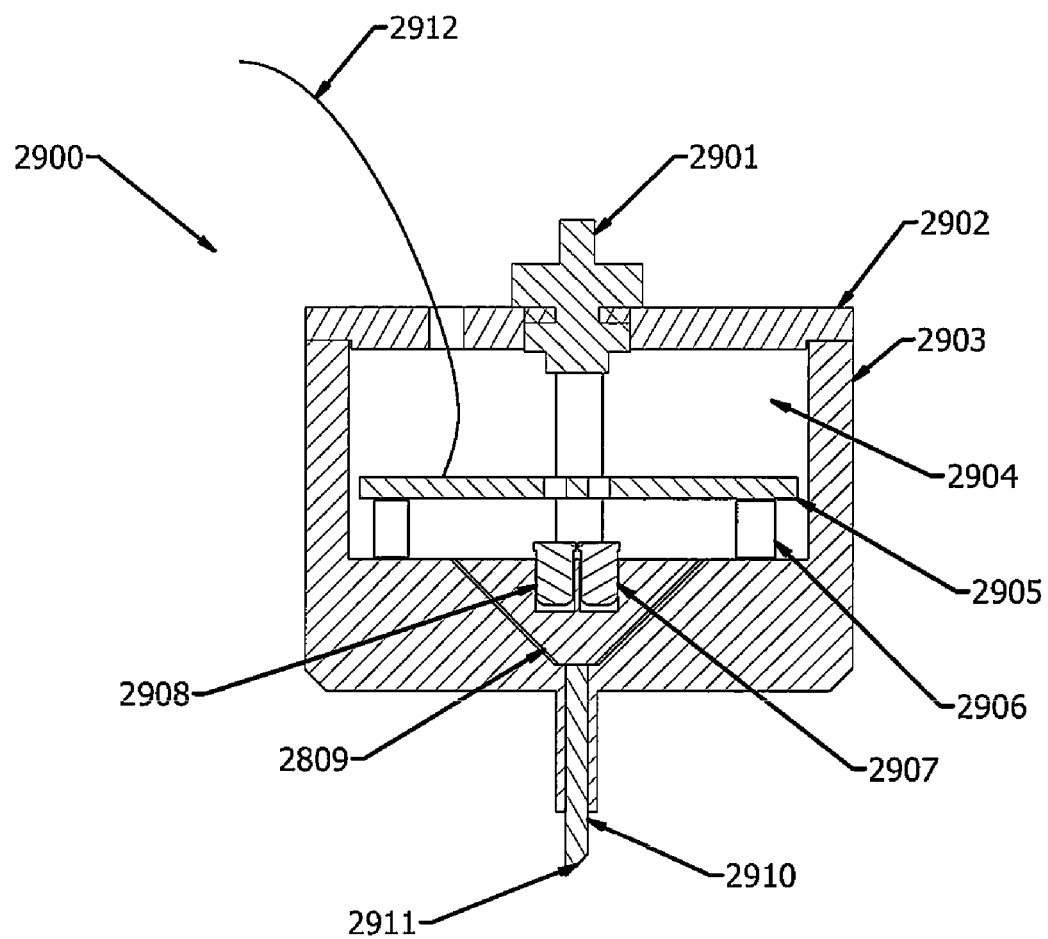
FIG. 30 depicts a cardiac output monitor calibrator.

The Calibrator 2900 of FIG. 30A comprises of 4 way switch 2901, top cover 2902, body 2903, cavity 2904, a circuit board (PCB) 2905, stand offs 2906, 830 nm LED 2907, 780 nm LED 2908, light collector 2909, and a light rod 2910.

The 4 way switch 2901 provides the user a plurality of the illumination choices. The switch 2901 includes an OFF, 780 nm low current, 780 nm high current, and 830 nm modes. The corresponding LEDs 2907 or 2908 will light up as selected through the switch by the user. The switch of the present calibrator is not limited to any number modalities. Ordinary practitioner will use the proper number of modalities for a given application.

The calibrator 2900 is a removable and an optical assembly device having the associated electronics incorporated within it. The device may simulate the optical inputs as seen by the fiber optics dialysis system or any other similar system. By supplying for example stimulus at 780 nm and 830 nm by LEDS 2908 and 2907, respectively, the device may simulate the laser illumination wavelengths and the fluorescence wavelength of the ICG dye, respectively.

The calibration includes testing the response of the system's components from the fiber optic probe receiving ends through intervening modules such as the photomultipliers (PMTS) to the processing module. In an exemplary embodiment, the results may be displayed on an oscilloscope, a computer monitor or any other compatible monitoring display device.

The calibrator comprises optics such as a plastic light guide 2910 that is tapered off at a 45-degree angle at its end 2911. The 780 nm and 830 nm lights are delivered by two LEDs, wherein the light is guided through the plastic rod. The optical output of the tapered side is approximately 10% of that of the uncut side. In operation, the calibrator is inserted into the cardiac output monitoring probe 2805 replacing the tubing 2812 of FIG. 28B and rotated until back fluorescence (BF) output is maximized when the 830 nm LED 2907 is excited. That position may be fixed for operation at 780 nm also. Although the normal ratios of transmission (T) and reflectance (R) are reversed, with R having the larger signal. Should it be necessary, the calibrator may be rotated 180 degrees to maximize the T stimulus.

The electronics may process a reference sine wave available from one of the lock-in amplifiers to stimulate the half wave rectified output of the diode driver. This waveform drives one of the two LEDs 2907 and 2908 with a fixed, and known current. The center-off switch 2901 allows each LED to be selected.

Figure 31A:
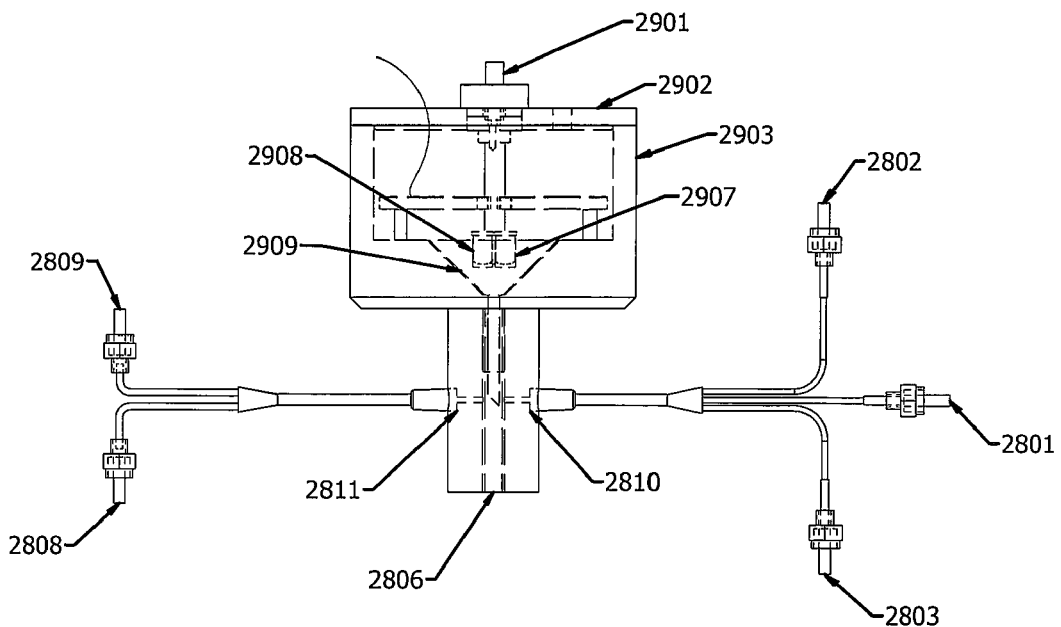
FIGS. 31A-B depict the front and top views of the calibrator of FIG. 30 when inserted into the dialysis probe assembly of FIG. 28A-C.
Figure 31B:
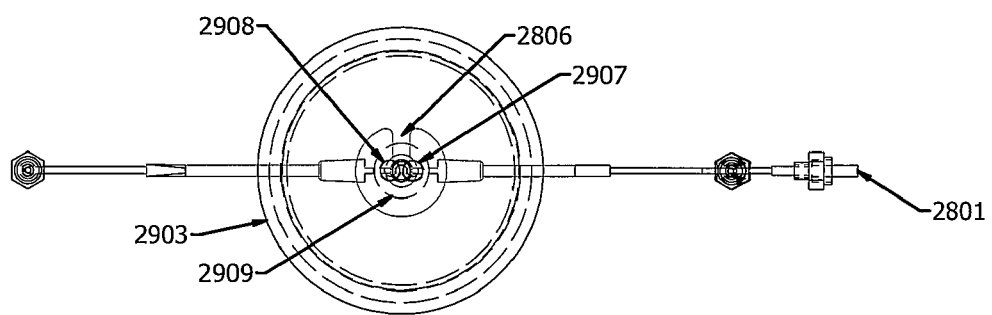
Figure 33A:
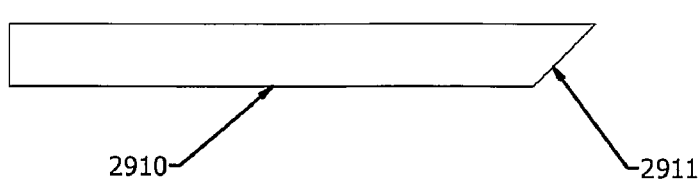
FIGS. 33A-C depict the side, front and 3d views of the light rod of the calibrator of FIG. 30.
Figure 33B:
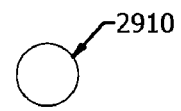
Figure 33C:
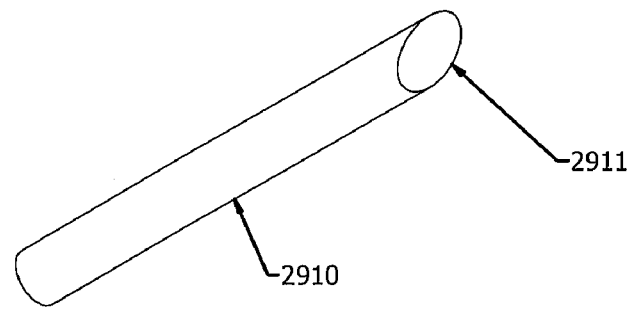

FIGS. 31A and 31B depict the side and top view of the calibrator 2900, respectively, when inserted into the probe assembly 2800 of FIG. 28A. As seen, the calibrator light rod 2901 replaces the blood tubing 2812. FIGS. 33A-C represents the light rod in side, front and 3D view, respectively, wherein the rod is tapered off at approximately 45 degrees. In the embodiment of FIG. 31A, the light generated by any of the LEDs will hit the tapered off surface 2911, wherein approximately 90% of the light will be directed toward the port 2810. Approximately only 10% of the generated light will be directed towards the 2811 port.

Figure 32A:
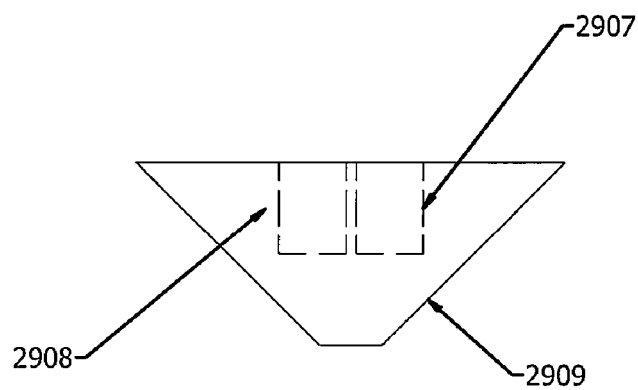
FIGS. 32A-C depict the side, top and 3d views, respectively, of the light collector of the calibrator of FIG. 30.
Figure 32B:
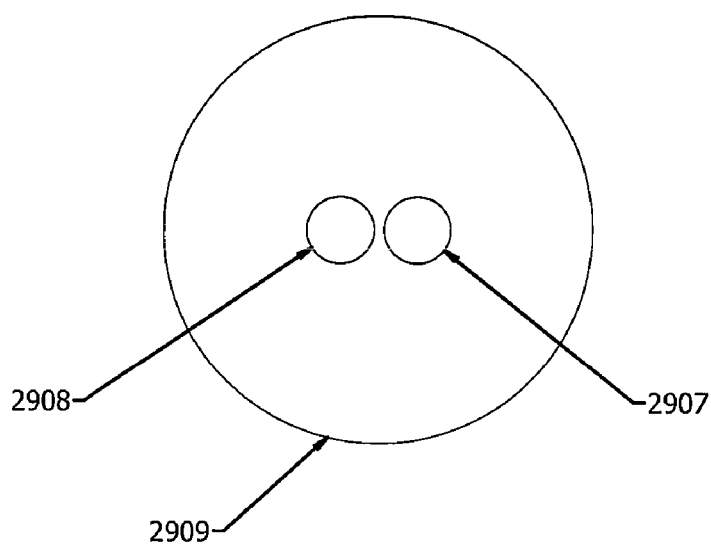
Figure 32C:
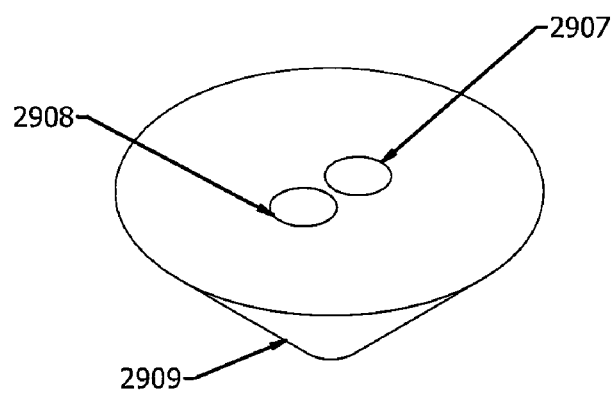

FIGS. 32A-C represent the light collector 2909 construction of the calibrator having the LEDs 2907 and 2908 integrated within it.

In the present dialysis probe calibration system the back fluorescence, forward fluorescence, reflection and transmission may be detected by their corresponding detectors of the system as in the actual dialysis application process. A user may be able to monitor the activity at each detecting ports and may validate the results of the output from each of individual ports.

The calibrator may provide the user with an indication that the cardiac output system is functioning according to manufacturer's specification. In the event that the calibrator indicates to the user that leads to investigation of the deviation from manufacturer settings, the user can follow proper steps to remediate the deviation. The calibration system may avoid the cardiac output monitoring (COM) system from being used if the calibrator does not deliver the proper results. By detecting errors early prior to COM process, incorrect diagnosis may be avoided.

The calibrator is inserted into the COM probe fixture and may use all or part of the existing COM system modules to run a diagnostic calibration process.

The calibrator body may be made of an opaque plastic and dark solid material i.e. black. The body cavity may be covered by the light tight top cover 2902 which is made from the same material as the body 2903. The LEDS 2907 and 29018 are wired to the PCB 2905 and seated in the light collector 2909. The light collector may be a conical optical part made of clear material, such as Plexiglas, and shaped in such way that it collects the dispersed light emitted by the LEDs down into the light rod 2910. It is a light efficiency device. The light collector 2909 may be tapered to 45 degrees in order to effectively collect the light and guide it down to the light rod.

The light rod 2910 is placed directly onto the collector. The light rod is made of the same material as the light collector. The 45-degree tapered beveled surface 2911 of the light rod provides a prism like surface that bends the light, in one embodiment by 90 degrees, reflected light will be directed into the fiber optic probe. The light leakage of about 10% as discussed above may be observed on the non-beveled side of the light rod. This split of light intensity provides for the necessary ratio of light intensity required for calibrating the channels across the probe fixture. The light collector may be painted white, except at its apex, so that the light is collected efficiently and having lower loss due to absorption by the black calibrator body. The light collector may also be coated with reflective material such as silver foil or coating.

Compensation for Tissue Perfusion by Doppler Flowmetry Technique

An alternative embodiment comprises compensating for a change in the fluorescence of an indicator circulating in the bloodstream of a tissue or organ that is caused by a variation of the blood content of the detection area (i.e. measurement site). This compensation is achieved by using Doppler flowmetry technique.

In this embodiment, the system for determining a physical parameter of the cardiovascular system of a subject comprises an illumination system configured to (a) excite an indicator present in the cardiovascular system at the detection area thereby causing the indicator to fluoresce and (b) to provide an electromagnetic radiation for a Doppler flowmeter measurement. This system further comprises a detection system configured to detect the indicator fluorescence intensity emerging from the detection area and to detect the intensity and the frequency distribution of the electromagnetic radiation reflected from the detection area. This system further comprises a computing system that is configured to compute a physical parameter of the cardiovascular system by using the indicator fluorescence measurement and compensate the cardiovascular system computation for the variation of the blood content of the detection area by using the Doppler flowmetry measurement.

The blood content of the skin or tissue at the detection area may change over time during the determination of the cardiovascular system parameter such as cardiac output and blood volume. The blood content of the detection area may change due to response to a disease or wound. The blood content may even change under normal physiologic conditions. Such changes modify the quantity of circulating indicator present in the tissue at the detection area, making it difficult to distinguish between the variations of the indicator concentration expected from the circulation of the indicator in the blood stream and the variations associated with changes in the blood content of the tissue.

As explained in detail above, an indicator is injected into the cardiovascular system, this indicator is excited by an electromagnetic radiation to fluoresce, and this fluorescence is detected using a detection system. This fluorescence information is used to determine a physical parameter of the cardiovascular system. The methods, systems, their related embodiments and combinations thereof, which are described above in detail, that use this indicator fluorescence information to determine a parameter of the cardiovascular system are all within the scope of this alternative embodiment of this invention. These fluorescence systems and methods are referred hereafter as "fluorescence technique" or "fluorescence measurements".

The compensation for the fluorescence measurements may be achieved by using the Doppler flowmetry technique. Briefly, in this technique, the measurement area is illuminated by an electromagnetic radiation. The moving blood cells cause a change in frequency of the reflected electromagnetic wave (so-called Doppler shift). The intensity and frequency distribution of the Doppler shift is directly related to the number and velocity of the blood cells in the sample volume. This information is used to determine the velocity and the cell density (i.e. number of cells per unit volume) of the blood at the detection area and thereby its perfusion. Any electromagnetic radiation that is suitable for determination of variation of the blood content of the detection area by Doppler shift is within the scope of this alternative embodiment. For example, ultrasonic as well as laser Doppler flowmetry techniques may be used to compensate a physical parameter of the detection area related with the cardiovascular system. Such Doppler systems and methods that may be used to compensate the fluorescence measurements to obtain a physical parameter of the cardiovascular parameter are referred hereafter as "Doppler flowmetry technique" or "Doppler flowmetry measurements".

During Doppler flowmetry measurements, variety of physical parameters such as the frequency of the reflected electromagnetic radiation, its frequency distribution and intensity of the reflected electromagnetic radiation at each frequency can be determined. These measured parameters may be used to compute other physical parameters related with the cardiovascular system at the detection area by using well-known computation techniques related with the Doppler flowmetry technique. The computed parameters may be for example velocity of blood flow, number of blood cells in the sample volume, and blood perfusion. The blood perfusion may be calculated in arbitrary units. The blood perfusion may also be calculated by calibrating the system of this alternative embodiment by using a motility standard comprising, for example, polystyrene particles in water. These measured parameters and calculated parameters may be used alone or in combination to compensate the fluorescence measurements to determine the physical parameter of the cardiovascular system. The physical parameters measured or computed by the Doppler flowmetry technique are referred hereafter as "Doppler flowmetry parameters".

As shown above in Example 2 that the fluorescence dilution cardiac output is highly correlated with aortic flow velocity determined by an ultrasonic Doppler flowmetry technique. It was also shown that the area under the indicator fluorescence dilution curve and the peak fluorescence intensity were linearly related to the laser Doppler perfusion signal intensity measured within a few minutes of the fluorescence recording and from the same location. (See, for example, Maarek J. M., Holschneider D. P., Rubenstein E. H., *Fluorescence Dilution Technique for Measurement of Cardiac Output and Circulating Blood Volume in Healthy Human Subjects*. Anesthesiology 2007; 106:491-8, the contents of which are incorporated herein by reference).

This linear correlation between the indicator fluorescence and the Doppler flowmetry measurements can be used to correct the cardiovascular system parameters determined by the fluorescence measurement as follows. For example, the perfusion of the detection area is determined by the Doppler flowmetry over time. Any variation in the perfusion level will indicate a change in the blood content of the detection area. Since the perfusion is linearly related with the blood content and also with the fluorescence measurements, the cardiovascular system parameters measured by the fluorescence technique can easily be corrected by using these linear relationships.

The Doppler flowmetry measurements may be carried out at any time. For example, the perfusion of the detection area is determined twice, first time before the ICG injection and second time after the ICG is metabolized by the patient's body. The variation of these two perfusion measurements is then used to correct the fluorescence measurements carried out after the ICG injection. In another example, the fluorescence and the Doppler flowmetry measurements are simultaneously carried out and the fluorescence measurements are continuously corrected for any change in the blood content of the same detection area. The timing of the Doppler flowmetry measurements is not restricted with the fluorescence measurements. They may be carried out independently of or simultaneously with the fluorescence measurements. Such Doppler flowmetry measurement timings and their variations are all within the scope of this alternative embodiment.

The illumination system provides the incident electromagnetic radiation for both the fluorescence and Doppler flowmetry measurements. In one approach, the illumination system may provide an incident electromagnetic radiation at one wavelength suitable for both the fluorescence and Doppler flowmetry measurements. For example, the illumination system may provide a laser beam at about 780 nm wavelength. This approach may simplify and/or decrease the cost of the illumination system construction. However, in another approach, the illumination system may also provide the incident electromagnetic radiation at more than one wavelength for both the fluorescence and Doppler flowmetry measurements. This approach may be used, for example, to avoid interferences caused by the reflected electromagnetic radiation during the fluorescence measurements. Such approaches and their combinations are thereby within the scope of this alternative embodiment.

As explained above in detail, in some embodiments of the fluorescence measurements, the incident electromagnetic radiation may be modulated at a specific frequency and a suitable demodulating system comprising, for example, a lock-in amplifier or a synchronous demodulator may be used to amplify the output of the detection system only at that frequency. This approach may increase the accuracy and sensitivity of the fluorescence measurements. However, the Doppler flowmetry technique may require a steady-state, which is unmodulated, electromagnetic radiation. Thus, if the incident electromagnetic radiation is modulated for the fluorescence measurements, the system may be modified to allow the Doppler flowmetry measurements. For example, the illumination system may comprise a plurality of electromagnetic radiation sources. In another example, the illumination system may comprise two lasers. One of these sources may be modulated and used for the fluorescence measurements and the other kept at a steady-state for the Doppler flowmetry measurements. Yet in another example, one electromagnetic radiation source may be used. During the fluorescence measurements, this source is modulated and during the Doppler flowmetry measurements, this source is kept at a steady-state. And the source is time-shared between these two measurements. Yet in another example, as explained above the fluorescence and Doppler flowmetry measurements may be carried out independently and/or by using sources that can provide electromagnetic radiation at plurality of wavelengths. All these approaches, their variations or similar approaches may be used to allow the fluorescence measurements to be carried out with a modulated electromagnetic radiation and they are all thereby within the scope of this alternative embodiment.

The illumination system may comprise at least one electromagnetic radiation source such as laser or laser diode. The illumination system may further comprise at least one optical fiber to guide the electromagnetic radiation to the detection area. In some embodiments, the illumination system may comprise an optical article such as mirror or a lens for guiding the electromagnetic radiation to the detection area. The illumination system may further comprise an optical article such as an optical filter for example to substantially isolate an electromagnetic radiation at a desired wavelength from noise.

The detection system of this alternative embodiment is configured to detect the indicator fluorescence intensity and to detect the intensity and the frequency distribution of the electromagnetic radiation reflected from the detection area. This detection may be achieved by any detector, such as photodetector. The detection system may comprise at least one photodetector. In one approach, the detection system may comprise only one detector suitable for both the fluorescence and Doppler flowmetry measurements. This approach may simplify and/or decrease the cost of the detection system construction. However, in another approach, the detection system may also comprise more than one detector. This approach may be used, for example, to avoid interferences caused by the indicator fluorescence and/or reflected electromagnetic radiation. Such approaches are thereby within the scope of this alternative embodiment.

The detection system may further comprise at least one optical fiber to guide fluoresced and reflected electromagnetic radiation from the detection area to the detection system, for example, to the detector. The detection system may further comprise an optical filter to filter out undesired wavelengths of the electromagnetic radiation. For example, a filter may be selected which corresponds to the peak wavelength range or around the peak wavelength range of the indicator emission. In some embodiments, the detection system may further comprise an optical article such as mirror or a lens for guiding the electromagnetic radiation from the detection area.

The illumination system, the detection system and/or at least one of the components forming these systems may be positioned proximately to at least one blood vessel of the cardiovascular system, for example, in the form of a probe. Respective positions of such probes in relation to each other may vary, for example, to maximize the intensity of the electromagnetic radiation they are guiding and to minimize undesired light interferences. In another example, the probe that directs the fluoresced light may be positioned to receive the fluorescence emitted from a tissue area very close to the area illuminated by the incident light to preserve linear relationship between the indicator fluorescence intensity and the blood content of the tissue at different indictor concentrations. In another example, the probe that directs the reflected light to the detection area may be positioned to receive the light reflected from the detection area and to direct it to the detection system. Yet in another example, respective positions of the incident, fluoresced and reflected light probes may be experimentally determined and these positions may be used in the construction of the system for determining the physical parameter of the cardiovascular system of a subject.

The devices and methods explained together with this alternative embodiment may be combined with any embodiment of devices and methods explained above for compensation of the physical parameters of the cardiovascular system determined by the fluorescence measurement technique. For example, the system of this alternative embodiment may be calibrated by techniques disclosed above in detail, including minimally invasive and noninvasive calibration techniques. Also, for example, the calculation techniques disclosed above in detail for determination of the physical parameters of the cardiovascular system such as the cardiac output and the blood volume may be incorporated to this alternative embodiment. This alternative embodiment may also be incorporated to the hemodialysis applications explained above in detail. Furthermore the detection area may be arterialized, as explained above. The illumination and/or the detection may be minimally invasive or noninvasive. Combinations of these previously explained embodiments may also be incorporated to this alternative embodiment and such combinations are thereby within the scope of this alternative embodiment.

The utility of the devices and methods of this alternative embodiment is further illustrated by the following examples, which are not intended to be limiting.

EXAMPLE 5

Figure 34:
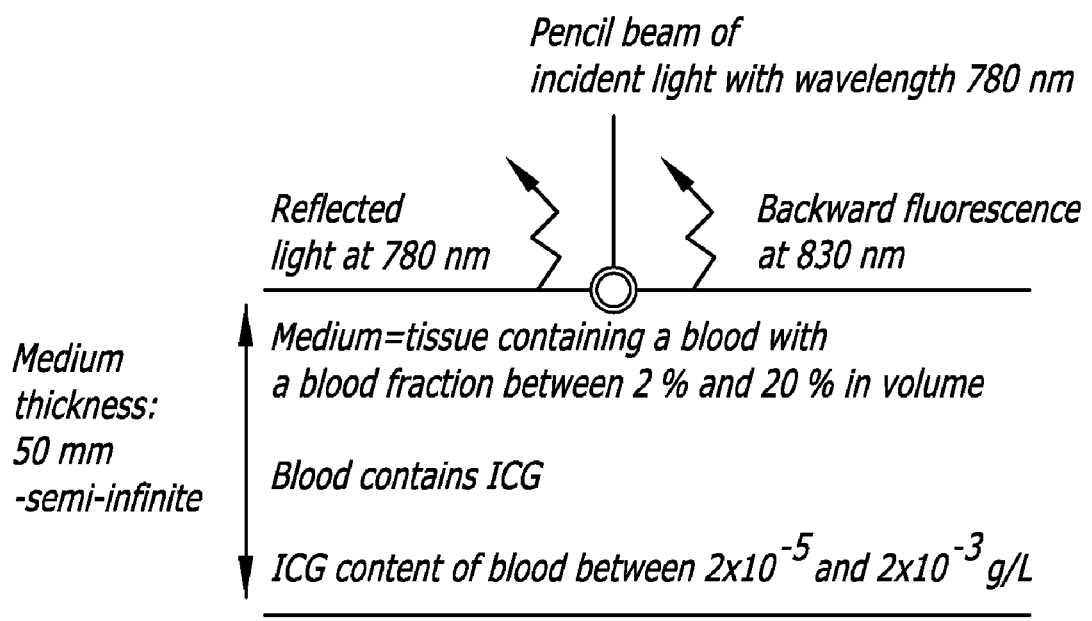
FIG. 34 shows a tissue model containing a variable fraction of blood and fluorescent dye.
Figure 35:
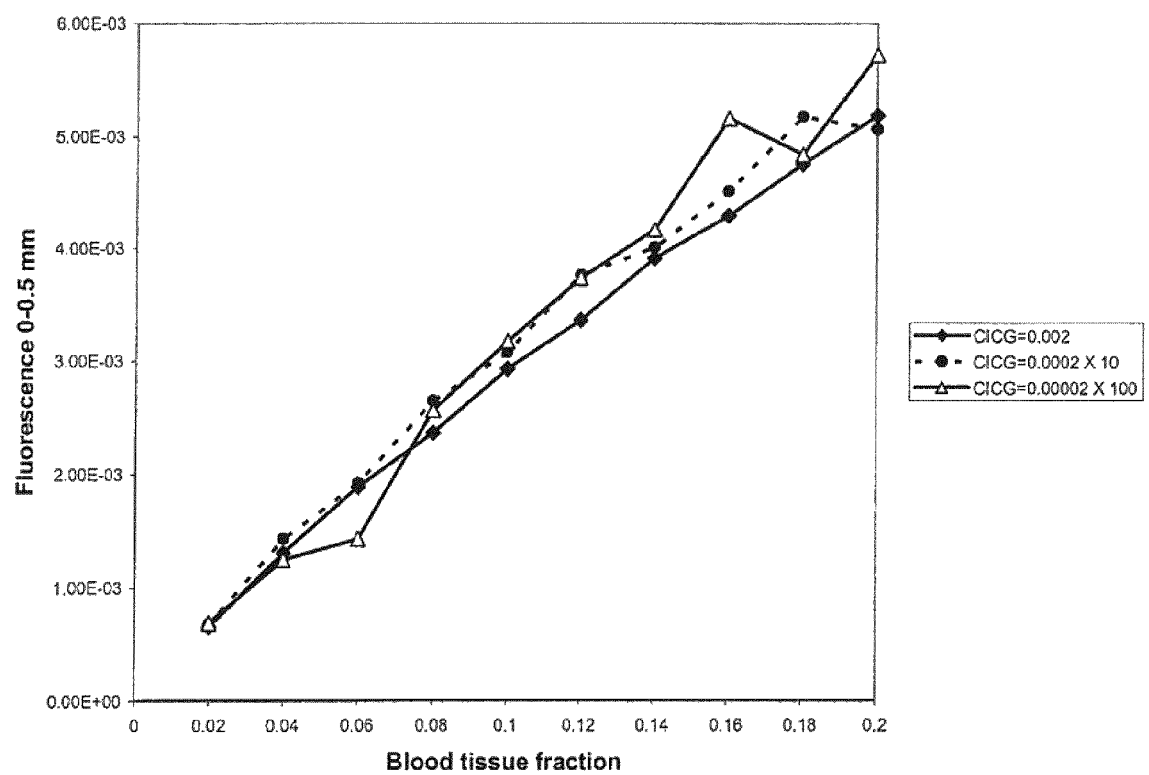
FIG. 35 is a graph showing the fluorescence signal measured at the surface of the tissue as ICG concentration was held constant and the blood content of the tissue model was varied.

Computer simulations of light transport in tissue may also aid determination or optimization of respective positions of illumination, fluorescence and Doppler probes. In this computer simulation example, the tissue model schematically shown in FIG. 34 was used and the variation of the fluorescence intensity at the tissue surface with blood content of the tissue (i.e. blood tissue fraction) was determined at three different blood ICG concentrations, 0.00002 mg/ml, 0.0002 mg/ml and 0.002 mg/ml. The fluorescence intensity was calculated at the surface point of the model near the illumination point (in the range of 0.0 mm to 0.5 mm from the illumination point). As shown in FIG. 35, the fluorescence intensity linearly increased with the blood content of the tissue when the ICG concentration in the blood was held constant, for example at 0.002 mg/ml. This linear relationship was not preserved when the fluorescence was calculated at several millimeters from the illumination point. Thus, it was concluded that it may be advantageous to measure the fluorescence intensity near the illumination point.

Also, as it was shown in FIG. 35, the fluorescence intensity linearly increased with the indicator concentration. In this figure, the fluorescence intensity calculated for the ICG concentrations of 0.00002 mg/ml and 0.0002 mg/ml was normalized to that calculated for the 0.002 mg/ml ICG concentration by multiplying the calculated intensities by 100 and 10 respectively. The fluorescence intensities for three different ICG concentrations lay on each other after the normalization at each blood tissue fraction, indicating that the fluorescence intensity linearly increases with the ICG concentration in the blood.

EXAMPLE 6

Figure 36:
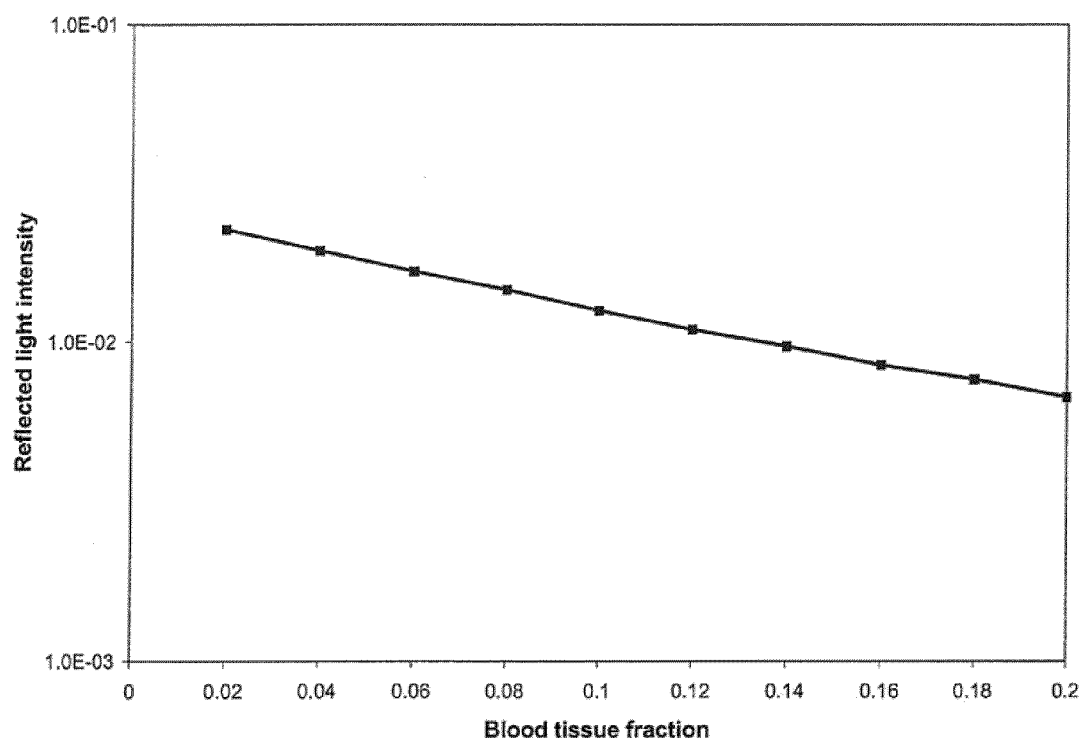
FIG. 36 is a graph showing the amount of excitation light reflected at the surface of the tissue as ICG concentration was held constant and the blood content of the tissue model was varied.

As shown in FIG. 36, it was also demonstrated that the intensity of the light reflected at the surface of the tissue and calculated at several millimeters distance (~4 mm) from the point of illumination decreased exponentially as the blood content of the tissue increased. In FIG. 36, reflected light intensity was calculated in an annulus extending from 3.5 to 4 mm centered around the illumination beam. On the semi-log plot, the reflected light intensity linearly decreased when the blood content increased (at the ICG concentration of 0 mg/ml). Thus, the reflected light intensity exponentially decreased with the increasing blood content of the tissue. The increase in the blood content augments the light absorption and the light scattering by the tissue, which diminishes the amount of reflected light from the tissue with increasing distance from the illumination point. Therefore, a measurement of the amount of light reflected at a few millimeters from the illumination point can be used to correct for variations in the content of blood in the tissue.

Therefore a combined measurement of the ICG fluorescence intensity obtained in close proximity to the illumination point and of the reflected light intensity obtained at the periphery of the area illuminated by the light source may be desirable. Such a combination of two signals allows correcting the fluorescence signal for changes in local blood tissue content and deriving the circulating blood ICG concentration independently from variations of the local blood perfusion.

EXAMPLE 7

In one embodiment, the cardiac output probe fibers may be shared between the fluorescence and Doppler measurements. In FIG. 29A, for example, the central laser excitation fiber 2813 is time shared between exciting the fluorescent dye and performing the Doppler measurement. The latter may be performed immediately before the injection of the dye. All or part of the outer band of fibers (2814) collects the Doppler-shifted return signal during Doppler measurements and then collects the reflected light signal from the tissue during the ICG's passage. In an alternative embodiment, a separate set of fibers (or individual optical fiber) collects the Doppler return signal.

EXAMPLE 8

Figure 37:
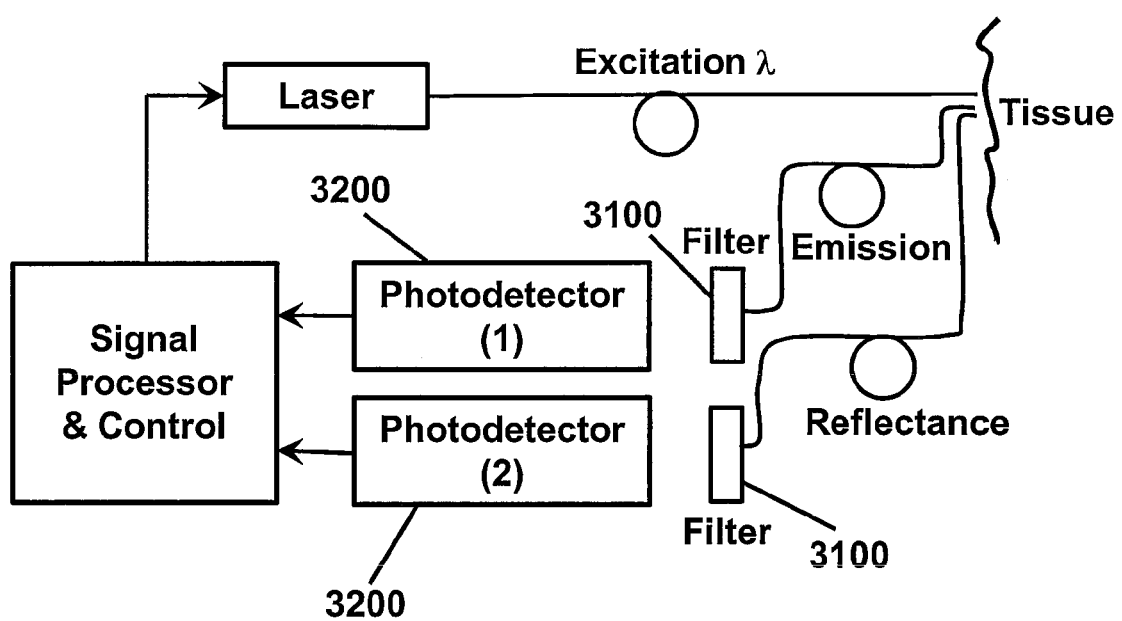
FIG. 37 is a schematic diagram showing an exemplary system that accounts for perfusion.

One embodiment of the combined fluorescence/Doppler signal processing unit is schematically depicted in FIG. 37. Each of the two bundles of fibers of FIG. 29A may be applied to a photodetector, which may be a photomultiplier tube, photodiode, or other device known to those skilled in the art. Optical band pass filters 3100 precedes each photodetector 3200 to restrict the signal to the appropriate wavelength region. The laser source is shared between the fluorescence and the Doppler measurements. The signal processor and the control unit comprises analog and/or digital signal processing electronics and software to modulate the laser diode, synchronously demodulate the back fluorescence, reflectance, and band limit the detected signals, form a signal proportional to the tissue perfusion using the Doppler return signal, and apply the correction factors that relate the fluorescence signal to ICG concentration and, hence, calculate cardiac output and blood volume.

The previous description of the disclosed embodiments is provided to enable any person skilled in the art to make or use the cardiac output monitor devices, methods and systems. Various modifications to these embodiments will be readily apparent to those skilled in the art, and the generic principles defined herein may be applied to other embodiments without departing from the scope of the devices, methods and systems described herein. Thus, the cardiac output devices, methods and systems are not intended to be limited to the embodiments shown herein but are to be accorded the widest scope consistent with the principles and novel features disclosed herein.

The invention claimed is:

1. A system for determining a physical parameter of the cardiovascular system of a subject comprising:
   a. an illumination system configured to provide an electromagnetic radiation to a detection area to excite an indicator administrated to the cardiovascular system to fluoresce, and to provide said electromagnetic radiation to said detection area for a Doppler flowmetry measurement;
   b. a detection system configured to detect the intensity of the indicator fluorescence emerging from the detection area, and to detect the intensity and the frequency distribution of electromagnetic radiation reflected from the detection area; and
   c. a computing system configured to compute a parameter of the cardiovascular system by using the indicator fluorescence intensity, to compute a Doppler flowmetry parameter of the detection area by using the reflected electromagnetic radiation intensity and its frequency distribution, and to compensate the cardiovascular system computation for a variation of the blood content of the detection area by using the computed Doppler flowmetry parameter.

2. The system of claim 1, wherein the illumination system is configured to provide an electromagnetic radiation with a wavelength within the range of 400 nm to 1,000 nm.

3. The system of claim 1, wherein the illumination system is configured to provide electromagnetic radiation at least one wavelength to cause the indicator to fluoresce and for the Doppler flowmetry measurement.

4. The system of claim 1, wherein the illumination system is configured to provide electromagnetic radiation at a plurality of wavelengths to cause the indicator to fluoresce and for the Doppler flowmetry measurement.

5. The system of claim 1, wherein the illumination system is configured to provide a modulated electromagnetic radiation during detection of the indictor fluorescence intensity.

6. The system of claim 5, wherein the illumination system is configured to modulate the electromagnetic radiation intensity at a selected frequency, and the detection system comprises at least one demodulating system for enhancing the detection of the indicator fluorescence only at the selected modulation frequency.

7. The system of claim 5, wherein the system is further configured to carry out the Doppler flowmetry measurements when the electromagnetic radiation provided by the illumination system is not modulated.

8. The system of claim 1, wherein the parameter of the cardiovascular system is the cardiac output of the subject and wherein the computing system is further configured to compute the cardiac output of the subject in absolute units of volume over time by:

a. converting the indicator fluorescence intensity detected over a period of time to a measured indicator concentration using a calibration curve and
b. computing the cardiac output of the subject in absolute units over the period of time based on the measured indicator concentration.

9. The system of claim 1, wherein the parameter of the cardiovascular system is the blood volume of the subject and wherein the computing system is further configured to compute the blood volume of the subject in absolute units of volume over time by:
a. converting the fluorescence intensity detected over a period of time to a measured indicator concentration using a calibration curve and
b. computing the blood volume by back extrapolating a slow phase of the indicator concentration curve to determine the blood volume.

10. A method of measuring a physical parameter of the cardiovascular system of a subject comprising:
a. administering to the cardiovascular system of a subject a detectable amount of at least one indicator;
b. providing an electromagnetic radiation to a detection area by using an illumination system to excite the indicator present at the detection area to fluoresce;
c. detecting the indicator fluorescence intensity emitted from the detection area by using a detection system;
d. detecting the intensity and the frequency distribution of the reflected electromagnetic radiation from the detection area for a Doppler flowmetry measurement by using said detection system,
e. computing at least one physical parameter of the cardiovascular system using the detected indicator fluorescence intensity, and
f. compensating the physical parameter of the cardiovascular system for variations of the blood content of the detection area by using the Doppler flowmetry measurement.

11. The method of claim 10, wherein the electromagnetic radiation is provided at a wavelength varying within the range of 400 nm to 1,000 nm.

12. The method of claim 10, wherein the electromagnetic radiation is provided at least one wavelength to cause the indicator to fluoresce and for the Doppler flowmetry measurement.

13. The method of claim 10, wherein the electromagnetic radiation is provided at a plurality of wavelengths to cause the indicator to fluoresce and for the Doppler flowmetry measurement.

14. The method of claim 10, wherein the indicator is capable of fluorescing at a wavelength varying within the range of 400 nm to 1,000 nm.

15. The method of claim 10, wherein the provided electromagnetic radiation is modulated during the detection of the indicator fluorescence intensity.

16. The method of claim 15, wherein the method further comprises carrying out the Doppler flowmetry measurement when the electromagnetic radiation is not modulated.

17. The method of claim 10, wherein the at least one physical parameter of the cardiovascular system is the cardiac output of the subject and the method further comprises converting the detected indicator fluorescence intensity to a measured indicator concentration using a calibration curve and determining the cardiac output of the subject in absolute units based on the measured indicator concentration.

18. The method of claim 10 further comprising removing a blood sample containing indicator from the subject, determining the indicator concentration in the removed blood sample, and computing the at least one physical parameter of the cardiovascular system using the determined indicator concentration.

19. The method of claim 10, wherein the physical parameter of the cardiovascular system is cardiac output and wherein the method further comprises detecting the indicator fluorescence intensity over a time period, forming an indicator fluorescence intensity curve for the time period, and wherein the computing of the cardiac output comprises at least one of curve fitting to a model equation or numerical integration.

20. The method of claim 10, wherein the physical parameter of the cardiovascular system is blood volume and wherein the method further comprises detecting the indicator fluorescence intensity over a time period, forming an indicator fluorescence intensity curve for the time period, converting the fluorescence intensity curve to the indicator concentration curve by using a calibration method and wherein the computing of the blood volume comprises back extrapolating a slow phase of the indictor concentration curve to determine the blood volume.

* * * * *